United States Patent
Schnable et al.

(10) Patent No.: US 9,523,099 B2
(45) Date of Patent: Dec. 20, 2016

(54) PLANT GENES INVOLVED IN NITRATE UPTAKE AND METABOLISM

(71) Applicant: Iowa State University Research Foundation, Inc., Ames, IA (US)

(72) Inventors: Patrick S. Schnable, Ames, IA (US); Sudhansu Dash, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 14/462,017

(22) Filed: Aug. 18, 2014

(65) Prior Publication Data

US 2014/0373198 A1   Dec. 18, 2014

Related U.S. Application Data

(62) Division of application No. 11/876,534, filed on Oct. 22, 2007, now abandoned.

(60) Provisional application No. 60/869,290, filed on Dec. 8, 2006.

(51) Int. Cl.
| | | |
|---|---|---|
| A01H 5/00 | (2006.01) | |
| A01H 1/00 | (2006.01) | |
| C12N 15/00 | (2006.01) | |
| C12N 15/82 | (2006.01) | |
| C07K 14/415 | (2006.01) | |
| C07H 21/04 | (2006.01) | |

(52) U.S. Cl.
CPC ......... *C12N 15/8261* (2013.01); *C07K 14/415* (2013.01); *C12N 15/8238* (2013.01)

(58) Field of Classification Search
None
See application file for complete search history.

(56) References Cited

U.S. PATENT DOCUMENTS

| | | | |
|---|---|---|---|
| 5,391,725 A | 2/1995 | Coruzzi et al. | |
| 5,608,144 A | 3/1997 | Baden et al. | |
| 5,633,441 A | 5/1997 | De Greef et al. | |
| 5,998,700 A | 12/1999 | Lightfoot et al. | |
| 6,084,153 A | 7/2000 | Good et al. | |
| 6,107,547 A | 8/2000 | Coruzzi et al. | |
| 6,342,581 B1 | 1/2002 | Rosen et al. | |
| 6,506,963 B1 | 1/2003 | De Both et al. | |
| 6,852,519 B2 | 2/2005 | Wei et al. | |
| 6,936,693 B2 | 8/2005 | Hresko et al. | |
| 6,939,701 B2 | 9/2005 | Yaver et al. | |
| 6,942,973 B2 | 9/2005 | Yaver et al. | |
| 7,038,030 B2 | 5/2006 | Litman et al. | |
| 7,193,033 B2 | 3/2007 | Mori et al. | |
| 7,195,901 B1 | 3/2007 | McKeon et al. | |
| 7,214,786 B2 | 5/2007 | Kovalic et al. | |
| 7,247,440 B2 | 7/2007 | Mori et al. | |
| 7,285,265 B2 | 10/2007 | Vogels et al. | |
| 7,348,142 B2 | 3/2008 | Wang | |
| 7,375,074 B2 | 5/2008 | Hirokazu et al. | |
| H2220 H | 7/2008 | Wang | |
| 7,396,979 B2 | 7/2008 | Alexandrov et al. | |
| 7,399,587 B2 | 7/2008 | Tenmizu et al. | |
| 7,427,399 B2 | 9/2008 | Jakobovits et al. | |
| 7,429,382 B2 | 9/2008 | Albone et al. | |
| 7,435,168 B2 | 10/2008 | Fatland-Bloom et al. | |
| 7,439,067 B2 | 10/2008 | Lasure et al. | |
| 7,442,533 B2 | 10/2008 | Williams et al. | |
| 7,473,526 B2 | 1/2009 | Wang | |
| 7,507,875 B2 | 3/2009 | Bloksberg et al. | |
| 7,511,190 B2 | 3/2009 | Creelman et al. | |
| 7,514,597 B2 | 4/2009 | Nakamura et al. | |
| 7,521,230 B2 | 4/2009 | Ikezu | |
| 7,525,016 B1 | 4/2009 | Peters et al. | |
| 7,538,204 B2 | 5/2009 | Ramli et al. | |
| 7,569,389 B2 | 8/2009 | Feldmann et al. | |
| 7,611,705 B2 | 11/2009 | Chang | |
| 7,659,446 B2 | 2/2010 | Sherman et al. | |
| 7,700,852 B2 | 4/2010 | Demmer et al. | |
| 7,709,611 B2 | 5/2010 | Li et al. | |
| 7,745,391 B2 | 6/2010 | Mintz et al. | |
| 7,750,207 B2 | 7/2010 | Wu et al. | |

(Continued)

FOREIGN PATENT DOCUMENTS

| | | |
|---|---|---|
| WO | WO 2006/030445 A2 | 3/2006 |
| WO | WO 2008/051608 A2 | 5/2008 |

OTHER PUBLICATIONS

Verdoy et al., "Transgenic Medicago truncatula Plants That Accumulate Proline Display Nitrogen-Fixing Activity With Enhanced Tolerance to Osmotic Stress," Plant Cell Environ 29(10):1913-1923 (e-pub Jul. 2006).

(Continued)

*Primary Examiner* — Phuong Bui

(74) *Attorney, Agent, or Firm* — LeClairRyan, a Professional Corporation

(57) ABSTRACT

The present invention relates nucleic acid molecules that are modulated (e.g., upregulated) by nitrogen in corn, to proteins or polypeptides encoded by these nucleic acid molecules, and promoters of these nucleic acid molecules. The present invention relates to a nucleic acid construct having a nucleic acid molecule that is modulated by nitrogen in corn, as well as to expression systems, host cells, plants, and plant seeds having the nucleic acid construct. The present invention also relates to a method of expressing the nucleic acid molecule that is modulated by nitrogen in a plant by growing a transgenic plant or a plant grown from a transgenic seed transformed with the construct. The present invention further relates to an isolated DNA promoter that can be used to direct nitrogen-regulated expression of an isolated nucleic acid in plants.

29 Claims, No Drawings

(56) References Cited

U.S. PATENT DOCUMENTS

| | | | |
|---|---|---|---|
| 7,750,209 B2 | 7/2010 | Tanaka et al. | |
| 7,786,272 B2 | 8/2010 | Goddard et al. | |
| 7,790,958 B2 | 9/2010 | Boukharov et al. | |
| 7,834,146 B2 | 11/2010 | Kovalic et al. | |
| 7,838,278 B2 | 11/2010 | Fatland-Bloom et al. | |
| 7,855,321 B2 | 12/2010 | Renz et al. | |
| 7,863,001 B2 | 1/2011 | Dai et al. | |
| 7,867,749 B2 | 1/2011 | Williams et al. | |
| 7,868,149 B2 | 1/2011 | Boukharov et al. | |
| 7,892,730 B2 | 2/2011 | Morris et al. | |
| 7,910,800 B2 | 3/2011 | Karchi et al. | |
| 7,956,242 B2 | 6/2011 | Zhang et al. | |
| 7,960,612 B2 | 6/2011 | Zhang et al. | |
| 7,968,689 B2 | 6/2011 | Rosen et al. | |
| 7,985,571 B1 | 7/2011 | Ryan | |
| 7,989,676 B2 | 8/2011 | Troukhan et al. | |
| 8,014,957 B2 | 9/2011 | Radich et al. | |
| 8,030,290 B2 | 10/2011 | Rossi et al. | |
| 8,030,546 B2 | 10/2011 | Reuber et al. | |
| 8,063,186 B2 | 11/2011 | Goddard et al. | |
| 8,106,174 B2 | 1/2012 | Kovalic et al. | |
| 8,110,725 B2 | 2/2012 | Riechmann et al. | |
| 2001/0000266 A1 | 4/2001 | Schmidt et al. | |
| 2001/0003848 A1 | 6/2001 | Frommer et al. | |
| 2002/0069430 A1 | 6/2002 | Kisaka et al. | |
| 2003/0022305 A1 | 1/2003 | Coruzzi et al. | |
| 2004/0031072 A1 | 2/2004 | La Rosa et al. | |
| 2004/0034888 A1 | 2/2004 | Liu et al. | |
| 2004/0123343 A1 | 6/2004 | La Rosa et al. | |
| 2004/0214272 A1 | 10/2004 | La Rosa et al. | |
| 2005/0044585 A1 | 2/2005 | Good et al. | |
| 2005/0158323 A1 | 7/2005 | Evans et al. | |
| 2006/0048240 A1 | 3/2006 | Alexandrov et al. | |
| 2006/0107345 A1 | 5/2006 | Alexandrov et al. | |
| 2006/0123505 A1 | 6/2006 | Kikuchi et al. | |
| 2006/0150283 A1 | 7/2006 | Alexandrov et al. | |
| 2007/0016974 A1 | 1/2007 | Byrum et al. | |
| 2007/0020621 A1 | 1/2007 | Boukharov et al. | |
| 2007/0061916 A1 | 3/2007 | Kovalic et al. | |
| 2007/0067865 A1 | 3/2007 | Kovalic et al. | |
| 2007/0143875 A1 | 6/2007 | Conner et al. | |
| 2007/0150978 A1 | 6/2007 | Byrum | |
| 2007/0224595 A1 | 9/2007 | Andersen et al. | |
| 2007/0277269 A1 | 11/2007 | Alexandrov et al. | |
| 2008/0114160 A1 | 5/2008 | Boukharov et al. | |
| 2008/0206837 A1 | 8/2008 | Vogels et al. | |
| 2008/0227955 A1 | 9/2008 | Hresko et al. | |
| 2009/0081210 A1 | 3/2009 | Evans et al. | |
| 2009/0087878 A9 | 4/2009 | La Rosa et al. | |
| 2009/0093620 A1 | 4/2009 | Kovalic et al. | |
| 2009/0094717 A1 | 4/2009 | Troukhan et al. | |
| 2009/0123986 A1 | 5/2009 | Williams et al. | |
| 2009/0144848 A1 | 6/2009 | Kovalic et al. | |
| 2009/0208564 A1 | 8/2009 | Li et al. | |
| 2009/0229008 A1 | 9/2009 | Bloksberg et al. | |
| 2009/0238772 A1 | 9/2009 | Vaishnaw et al. | |
| 2010/0011463 A1 | 1/2010 | Wiig | |
| 2010/0017910 A1 | 1/2010 | Ascenzi | |
| 2010/0037352 A1 | 2/2010 | Alexandrov et al. | |
| 2010/0037355 A1 | 2/2010 | Alexandrov et al. | |
| 2010/0058489 A1 | 3/2010 | Ikezu | |
| 2010/0083407 A1 | 4/2010 | Feldmann et al. | |
| 2010/0162433 A1 | 6/2010 | McLaren et al. | |
| 2010/0168205 A1 | 7/2010 | Meyers et al. | |
| 2010/0286378 A1 | 11/2010 | Li et al. | |
| 2011/0008322 A1 | 1/2011 | Zauderer et al. | |
| 2011/0105347 A1 | 5/2011 | Wu et al. | |
| 2011/0126316 A1 | 5/2011 | Yu et al. | |
| 2011/0138499 A1 | 6/2011 | Zhang et al. | |
| 2011/0145946 A1 | 6/2011 | Vinocur et al. | |
| 2011/0158904 A1 | 6/2011 | Albone et al. | |
| 2011/0167514 A1 | 7/2011 | Brover et al. | |
| 2011/0177228 A1 | 7/2011 | Alexandrov et al. | |
| 2011/0179501 A1 | 7/2011 | Croce et al. | |
| 2011/0179519 A1 | 7/2011 | Coruzzi et al. | |
| 2011/0179531 A1 | 7/2011 | Kovalic et al. | |
| 2011/0184045 A1 | 7/2011 | Hartmann | |
| 2011/0201667 A1 | 8/2011 | Geisbert et al. | |
| 2011/0209246 A1 | 8/2011 | Kovalic et al. | |
| 2011/0214205 A1 | 9/2011 | Dietrich et al. | |
| 2011/0214206 A1 | 9/2011 | La Rosa et al. | |
| 2011/0231959 A1 | 9/2011 | Kovalic et al. | |
| 2012/0017292 A1 | 1/2012 | Kovalic et al. | |
| 2012/0017338 A1 | 1/2012 | Wu et al. | |
| 2012/0023611 A1 | 1/2012 | Cao et al. | |
| 2012/0144520 A1 | 6/2012 | McLaren et al. | |
| 2015/0096077 A1 | 4/2015 | McLaren et al. | |

OTHER PUBLICATIONS

Yanagisawa, Shuichi, "Improved Nitrogen Assimilation Using Transcription Factors," available at http://www.isb.vt.edu/articles/sep0401.htm, 5 pages (Sep. 2004).
GenBank Accession No. AJ461376 (May 21, 2002).
GenBank Accession No. BM350754 (Jan. 16, 2002).
GenBank Accession No. BM351356 (Jan. 16, 2002).
GenBank Accession No. CC605134 (Jun. 18, 2003).
GenBank Accession No. CC671403 (Jun. 19, 2003).
GenBank Accession No. CC671410 (Jun. 19, 2003).
GenBank Accession No. CT854843 (Nov. 1, 2006).
GenBank Accession No. CT859984 (Nov. 1, 2006).
GenBank Accession No. CW395167 (Nov. 1, 2004).
GenBank Accession No. CW447049 (Nov. 2, 2004).
GenBank Accession No. CX111468 (Jun. 3, 2005).
GenBank Accession No. BG840928 (May 29, 2001).
GenBank Accession No. BG840889 (May 29, 2001).
GenBank Accession No. BG841093 (May 29, 2001).
GenBank Accession No. BG842208 (May 29, 2001).
GenBank Accession No. BG842452 (May 29, 2001).
GenBank Accession No. BG873755 (May 29, 2001).
GenBank Accession No. BG873856 (May 29, 2001).
GenBank Accession No. BG874013 (May 29, 2001).
GenBank Accession No. BM072886 (Nov. 13, 2001).
GenBank Accession No. BM073122 (Nov. 13, 2001).
GenBank Accession No. BM073865 (Nov. 13, 2001).
GenBank Accession No. BM073866 (Nov. 13, 2001).
GenBank Accession No. BM079064 (Nov. 14, 2001).
GenBank Accession No. BM333948 (Jan. 16, 2002).
GenBank Accession No. BM350368 (Jan. 16, 2002).
Yanagisawa et al., "Metabolic Engineering With Dof1 Transcription Factor in Plants: Improved Nitrogen Assimilation and Growth Under Low-Nitrogen Conditions," *Proc. Nat'l. Acad. Sci. U.S.A.* 101(20):7833-7838 (2004).
Martin et al., "Two Cytosolic Glutamine Synthetase Isoforms of Maize Are Specifically Involved in the Control of Grain Production," *Plant Cell* 18:3252-3274 (2006).
Osanai and Tanaka, "Keeping in Touch with PII: PII-Interacting Proteins in Unicellular Cyanobacteria," *Plant Cell Physiol.* 48(7):908-914 (2007).
Hsieh et al., "A PII-Like Protein in Arabidopsis: Putative Role in Nitrogen Sensing," *Proc. Nat'l. Acad. Sci. U.S.A.* 95:13965-13970 (1998).
Miller, M., Oral Presentation, "Global Transcript Profiles in Nitrate-Induced Roots of Maize Seedlings," Iowa State University Department of Biochemistry, Biophysics & Molecular Biology, Ames, Iowa (Dec. 8, 2006).
International Search Report and Written Opinion for PCT/US2007/082123 (Oct. 15, 2008).
Declaration of James McLaren (signed Dec. 2, 2009).
Forde, "Local and Long-Range Signaling Pathways Regulating Plant Responses to Nitrate," *Annu. Rev. Plant Biol.* 53:203-24 (2002).
Hirel et al., "Towards a Better Understanding of the Genetic and Physiological Basis for Nitrogen Use Efficiency in Maize," *Plant Physiol.* 125:1258-70 (2001).
Loudet et al., "Quantitative Trait Loci Analysis of Nitrogen Use Efficiency in Arabidopsis," *Plant Physiol.* 131:345-58 (2003).

(56) References Cited

OTHER PUBLICATIONS

Miflin et al., "The Role of Glutamine Synthetase and Glutamate Dehydrogenase in Nitrogen Assimilation and Possibilities for Improvement in the Nitrogen Utilization of Crops," *J. Exper. Bot.* 53(370):979-87 (2002).
Orsel et al., "Nitrate Transport in Plants: Which Gene and Which Control?" *J. Exper. Bot.* 53(370):825-33 (2002).
Quaggiotti et al., "Expression of a Putative High-Affinity $NO_3^-$ Transporter and of an $H^+$-ATPase in Relation to Whole Plant Nitrate Transport Physiology in Two Maize Genotypes Differently Responsive to Low Nitrogen Availability," *J. Exper. Bot.* 54(384):1023-31 (2003).
Thum et al., "Genome-Wide Investigation of Light and Carbon Signaling Interactions in *Arabidopsis*," *Genome Biol.* 5(2):R10.1-R10.20 (2004).
Wang et al., "Microarray Analysis of the Nitrate Response in Arabidopsis Roots and Shoots Reveals Over 1,000 Rapidly Responding Genes and New Linkages to Glucose, Trehalose-6-Phosphate, Iron, and Sulfate Metabolism," *Plant Physiol.* 132:556-67 (2003).
Wang et al., "Genomic Analysis of the Nitrate Response Using a Nitrate Reductase-Null Mutant of Arabidopsis," *Plant Physiol.* 132:2512-22 (2004).
Wullschleger et al., "Emerging Use of Gene Expression Microarrays in Plant Physiology," *Comp. Funct. Genom.* 4:216-24 (2003).
Liu et al., N_Geneseq_200812 Database, Accession No. ADX49734, US 2004/0034888, Feb. 19, 2004.
Liu et al., A_Geneseq_200812 Database, Accession No. ADY08501, US 2004/0034888, Feb. 19, 2004.

PLANT GENES INVOLVED IN NITRATE UPTAKE AND METABOLISM

This application is a divisional application of U.S. patent application Ser. No. 11/876,534, filed Oct. 22, 2007, which claims the benefit of U.S. Provisional Patent Application Ser. No. 60/869,290, filed Dec. 8, 2006, each of which is hereby incorporated by reference in its entirety.

FIELD OF THE INVENTION

The present invention relates to plant genes involved in nitrate uptake and metabolism.

BACKGROUND OF THE INVENTION

Nitrogen plays an important role in various plant functions, including metabolism, resource allocation, growth, and development (Crawford, N. M., "Nitrate: Nutrient and Signal for Plant Growth," *Plant Cell* 7:859-868 (1995); Marschner, M., *Mineral Nutrition of Higher Plants, 2d ed.*, Academic Press Ltd.: London (1995); and Stitt et al., "The Molecular Physiological Basis for the Interaction Between Elevated Carbon Dioxide and Nutrients," *Plant Cell Environ.* 22:583-622 (1999)). Further, nitrogen is a major component of proteins and nucleic acids, as well as various secondary metabolites found in plants (Marschner, M., *Mineral Nutrition of Higher Plants, 2d ed.*, Academic Press Ltd.: London (1995)). Therefore, nitrogen is one of the most important inorganic nutrients of plants. Inorganic nitrogen is added to many crop plants in the form of nitrogenous fertilizers (see Frink et al., "Nitrogen Fertilizer: Retrospect and Prospect," *Proc. Natl. Acad. Sci. USA* 96:1175-1180 (1999)). Nitrogen is principally added to the soil in the form of ammonia ($NH_4^+$) and nitrate ($NO_3^-$). However, estimates of nitrogen uptake efficiency have shown that between 50 and 70 percent of the applied nitrogen is lost from the plant-soil system (Peoples et al., "Minimizing Gaseous Losses of Nitrogen," In *Nitrogen Fertilizer in the Environment*, Bacon, P. E., ed., Marcel Dekker, pp. 565-606 (1995)).

The application of inorganic nutrient fertilizers is one of the major expenses incurred by producers of high-yielding crop plants (see Good et al., "Can Less Yield More? Is Reducing Nutrient Input Into the Environment Compatible with Maintaining Crop Production?" *Trends in Plant Science* 9(12):597-605 (2004)). Further, reports have indicated that nitrogen-based fertilizers may be associated with environmental damage (see Vitousek et al., "Human Alternation of the Global Nitrogen Cycle: Causes and Consequences," *Ecol. Appl.* 7:737-750 (1997)). Therefore, one important way of decreasing the amount of inorganic nitrogen that is applied to plant crops is to develop ways to improve nitrate use efficiency ("NUE") in plants.

Traditional plant breeding and marker-assisted selection are techniques that have been investigated for developing and identifying plants with increased NUE (see Good et al., "Can Less Yield More? Is Reducing Nutrient Input Into the Environment Compatible with Maintaining Crop Production?" *Trends in Plant Science* 9(12):597-605 (2004)). However, these approaches are often time-consuming and labor-intensive. An alternative approach is to use genetic engineering techniques to develop transgenic crop plants that have enhanced NUE. This approach requires the identification of genes that enhance NUE. Efforts have been reported regarding identifying genes that are regulated by nitrogen levels in *Arabidopsis* (Scheible et al., "Genome-Wide Reprogramming of Primary and Secondary Metabolism, Protein Synthesis, Cellular Growth Processes, and the Regulatory Infrastructure of *Arabidopsis* in Response to Nitrogen," *Plant Physiol.* 136:2483-2499 (2004)). However, there is a need to identify genes that are involved in nitrate uptake and metabolism in economically important crop plants such as corn.

The present invention is directed to overcoming these and other deficiencies in the art.

SUMMARY OF THE INVENTION

The present invention relates to nucleic acid molecules from corn (maize) that are modulated by nitrogen (e.g., that up-regulated by nitrogen). The present invention also relates to isolated proteins or polypeptides encoded by the nucleic acid molecules. The present invention further relates to promoters of the nucleic acid molecules of the present invention.

The present invention further relates to a nucleic acid construct having a nucleic acid molecule of the present invention (i.e., a nucleic acid molecule that is modulated, e.g., up-regulated, by nitrogen in corn). The construct also includes a 5' DNA promoter sequence and a 3' terminator sequence. The nucleic acid molecule, the DNA promoter sequence, and the terminator sequence are operatively coupled to permit transcription of the nucleic acid molecule.

The present invention also relates to an expression system, host cells, plant cells, plants, and plant seeds having a nucleic acid construct that includes a nucleic acid molecule that is modulated by nitrogen in corn.

Another aspect of the present invention is a method of expressing a nucleic acid molecule that is modulated by nitrogen in a plant. This method involves providing a transgenic plant or plant seed transformed with a nucleic acid construct having a nucleic acid molecule that is modulated by nitrogen in corn, a 5' DNA promoter sequence, and a 3' terminator sequence. The method involves growing the transgenic plant or a transgenic plant grown from the transgenic plant seed under conditions effective to express the nucleic acid molecule in the transgenic plant or the plant grown from the transgenic plant seed.

Another aspect of the present invention relates to an isolated DNA promoter from corn suitable for inducing nitrogen-regulated expression of a protein encoded by an isolated DNA molecule operably associated with the DNA promoter. The present invention further relates to a nucleic acid construct including the isolated DNA promoter, as well as expression vectors, host cells, plants, and plant seeds containing the nucleic acid construct. The present invention also relates to a method of directing nitrogen-regulated expression of an isolated nucleic acid in plants. This method involves transforming a plant cell with the nucleic acid construct described in this paragraph and regenerating a plant from the transformed plant cell. By this method, expression of the nucleic acid molecule, under control of the DNA promoter, occurs in the plant and is upregulated by nitrogen.

Nitrate use efficiency affects both grower profitability and the ecological sustainability of intensive corn production. The present invention is effective in providing a means to improve the NUE by enhancing the nitrogen uptake of crop plants such as corn. In particular, the nucleic acid constructs of the present invention can be used to develop corn germplasm using marker-assisted selection and/or transgenic approaches. Thus, the present invention is useful in increasing the nitrate absorption and usage efficiency by crop plants and thus reduce the use of nitrate supplements. The nucleic acid constructs of the present invention include nucleic acid molecules corresponding to genes of corn plants and, hence, have the most direct bearing on nitrate metabolism in corn. Therefore, such genes may be more directly relevant to corn improvement than genes from non-crop plants such as *Arabidopsis*.

DETAILED DESCRIPTION OF THE INVENTION

The present invention relates to nucleic acid molecules (e.g., genes) from corn (maize) (e.g., from B73 seedlings) that are modulated (e.g., up-regulated) by nitrogen (e.g., in the form of nitrate, calcium nitrate, etc.). These genes and their promoters are natural targets for use in corn improvement. These genes can be used to improve corn germplasm with the use of marker-assisted selection and/or transgenic approaches. The present invention provides nucleotide sequences of the full-length cDNA clones of such genes. The present invention also provides the amino acid sequences of the isolated proteins or polypeptides encoded by these genes, as well as their putative promoters (upstream of transcription start site of the genes).

A suitable nucleic acid molecule of the present invention is a gene that is up-regulated by nitrogen and contained in a full-length cDNA clone having the nucleotide sequence of SEQ ID NO:1, as follows:

CGACTGGAGCACGAGGACACTGACATGGACGGAAGGAGTAGAAAATATTG

CCTGCTCCGACGACCTTGAATATTCACTGGCCATTTAATTTCTACTTACA

AGCCTGAATGAGCTAGAGATCCATCTGCTTCTGTACGTGCTCGTCAGGTA

CGCTCGTAAAAAGAAAAGAAAAAAAAAGAAGAGATCGAGATCGATCTGTT

GACGACGCCCCCGTCGCCGAT<u>ATG</u>GGCGACCTCTCTGTCGGCCACAGCCG

CCGCTGGTGCGGCCGTTTCGCGGCCGTCCTTTGCCTGTGCGCGGCCTTCT

GCAAGCCAGATGAACTCCCGATGGATCCACTGCCGAACTTGCCGCCGACG

AGGTCGCTGCAGTGCTTCGAGGACGAACAGGTGTACAGCTGCTGCGAGGG

CGCGTACAGGCTAAACCCATCGGGAATCATCGCCGTTCCCGTCGGCGCGG

TGGACTACTACTGCGGCGGCGCGTGCGTGGTGGAGACGGAGGACGTGCTC

AACTGCGTGGCCAGCGCCCTGGACGGCTTCGCCTTCTACAACGGGGCCTC

CGTGGAGGACGTGCGCTACGCACTCAGGCGGGGCTGCAGCCACACCGCCA

GAAGAGGCGACTTCAACGATTTGGAGCCGCATCTGGGCGACTACCCTGAC

ATCTATGGCGACGATGATGAGCACAGCTTTGGCAGCAAGGTTGTTGCAGC

TCCTCTGAGGTTGCTCGCGTTTCTTGGCGGTGCGGGGCTGTTCTTCCTGG

GCCCTTGA (Underlined=GeneRacer Oligo sequence; Bold/Underlined=start codon; coding sequence in bold) (Sequence of 5' RACE product CW13E07-Full_Length cloned into pCR4-TOPO) (derived from MEST13-E07, GB_ACC# BG840928)

The predicted protein or polypeptide encoded by the full-length cDNA clone of SEQ ID NO:1 has an amino acid sequence of SEQ ID NO:2, as follows:

MGDLSVGHSRRWCGRFAAVLCLCAAFCKPDELPMDPLPNLPPTRSLQCFE

DEQVYSCCEGAYRLNPSGIIAVPVGAVDYYCGGACVVETEDVLNCVASAL

DGFAFYNGASVEDVRYALRRGCSHTARRGDFNDLEPHLGDYPDIYGDDDE

HSFGSKVVAAPLRLLAFLGGAGLFFLGP

A putative promoter (upstream of the transcription site of the gene) for the gene of the full-length cDNA clone of SEQ ID NO:1 has a nucleotide sequence of SEQ ID NO:3, as follows:

ccgcaagagggagtctttaccgagtgtcacctaatacgcttggcgaagga cctggtaaaagggcccacagggagcttttttgctaagtgtctgtacagtgg acactcggcaaagagtgagcctttgccgagtgtcactccgtcaccgttac ctggtgtcgtgacgacggcttttctttgtcgagtaccgagtgacactcga caaaacctttgccgagcgtccgataaaaagtattcggcaaagaagccgtt gccgtctttgccgagtgttttccagactttgccgagtgtttcagacactc ggcaaagaacctgattccgatagtgaaggtcttacaccccgatccacccc aattcgtgcgtattggagcaagtacccaaacaaaaccgtactgggaataa ttacctccgttcgctgcagtttgcagaacagcagttcaatgctacaggac gacgcagctgcagcgaacatgcatgcatttgaactcactccgttcactga tggacaagaggcatctgggtgactaataaaagaacgacacacacggacag cttctagaagtattggtagcgcatgaacaacaatgccgctgttagcttgt actgaggcacgaaacatgaatctgacctactactgacttctactataata atagtatatagtatggccaggccaggccaactccggcgaaaacgggagta cgcatgcagatggagcggcacattagtaggctgtttggtttgaagaatgg gctagtctatcatcttctcactctccacttttttgtttggtttgtggaat gaaatgagttgattcatcatcacctcattccttatagttagttagttagt actaatatgaggaatatggtcatcccaccaaatttgaggaatggatccac gatgtaccaccacatttgcatgaagtgattcctcaaaccaaacaccccc aaatgtaaaccgagtcatgcctccgatcccaaccttcgtgtttcccacca aacacacgcgtacagaggccaagcacacgcacaaaagcaagcctcgatcg tagcccgtgcctaaccctgccgatgccgtaataaacttgtgtgctccacg caaccatgaaatgaacctagaaatcgcagggcgggatgcgagtgaaaag gagcgggcaggtcaggtaggtttgaactctctcctataataatcctagct agcacacttgcccagattatattgcctgctccgacgaccttgaatattca ctggccatttaatttctacttacaagcctgaatgagctagagatccatct gcttctgtacgtgctcgtcaggtacgctcgtaaaagaaagaaaaaaaa agaagagatcgagatcgatctgttgacgacgcccccgtcgccgatatggg cgacctctctgtcggccacagccgccgctggtgcggccgtttcgcggccg tcctttgcctgtgcgcggccttctgcaagccaggtgcgtgctcaccgtca acacacgcaccattattccaccctcccaaggagcacagtacaacgcacgt acatatacctctcctcaatcgatatatagttacgtcttacgtactatcta gttaatctatcacgttgatgtctaatatagactccgcatggcatatgcat gcagatgaactcccgatggatccactgccgaacttgccgccgacgaggtc gctgcagtgcttcgaggacgaacaggtaagctaacaagcaagagcgtgtt tggtttcatgctaggacagagttgcataccacgtagctatcataagccta ccacacgtagctatcacagcctgtcgatttcgttcggtcgcctgacggta aacatcgctgcccgagaggcgagctcttttttgacaagcctcgacgaacca aataagccaagtcctactgtacgagggcgatcgaggcgccgaggcctgtg tgatgtgatgccgtgtcgtggtcacccaccagctgctgtgtacattgg tccccgtgccgcgcgtcgtaaccgcatgcggcatgccgctgcatgcaggt gtacagctgctgcgagggcgcgtacaggctaaacccatcgggaatcatcg ccgttcccgtcggcgcggtggactactactgcggcggcgcgtgcgtggtg gagacggaggacgtgctcaactgcgtggccagcgccctggacggcttcgc cttctacaacggggcctccgtggaggacgtgcgctacgcactcaggcggg gctgcagccacaccgccagaagaggtccccaagtttctcgcctactagct catctctctctacgtaccagccaagctagatcgactaccagtctccgcag cagtgcattcggaacgaccgctgacaaactgacaggctcgtgttcctgtc agcgcaggcgacttcaacgatttggagccgcatctgggcgactaccctga catctatggcgacgatgatgaacacagctttggcagcaaggttgttgcag ctcctctgaggttgctcgcgtttcttggcggtgcggggctgttcttcctg ggcccttgaacgaagatataaaagaactagcgatgtgatccgcgtaaata tatactccgtatatagcatgacatgagtatctagtttgtcttatatggta aaccatactaaattttcttgtatggcattaaaaaaaattaagactttatt tagttatttgactagttgttctctctggatcctctaatcagttcgaactc tataagcttttttattccactcctatctagaggtcgcataatatgctaag gtgagatcttgatgtctttcgttttttaactcgataaagttgttgtgag tctctcttataaaattattttaatgctaatattagattttagtcagaga tatgcagttgaccgttttgcactaaaatattttgaatttactatagtat tagttgtctactaatcacagctaaaaccgttttattttagttttttta taacagaaaaatatctctggaaacgaaaacggcaacacagtagttcaaa aatatcgaagacaataatttaacatgaaaatatatatgtaatgatcgga atctaaaaaacaatcactaaatataaacatatagtaacatgtactctcaa ttgacctgaaaaagcacataacctatagatccacaaagtaacgaagatt gaagcatgaaaaatagaccatcatacattaaagggttgtgcttatttagc tctagaataacctccttaagagcaacttcatttgcaacaacattgtctag agttaaagagaatattttcttctctgtaaaccatttcaataagcatgaac tgggtctaagagacaaattcttaccgttgtgccgacccagaacatgatcg aaatttgtaattcgcttctgtatttgtgaatcatcatctacccaatgtac catgatacacatgtacctttattctgatttgatatccacatctccatgg tagcactgaagtgacaattaagggttttaaaaaatttatacaacacatca tttttatgcaaaagagatccattacttcttttctaacaatgacatgtgac tttatagaaaatataggctttaaaggtttaatgaaatccataaagtattc atgttcaagaatgttaaatgggtactcatgaatgataatagtagtataaa acttcctcaaactaattgactcgtcatatttatatggttggacaatatat agatatacctaccttatgatctttttctgatttgagctcctgctatctta gtaaaaccttatgataacgcttctaatgcaaccaaaactaagttgttcct ctatggcttttagcactacctttgtaagtcctattttttgtagctcagaaa cttttcatttggcccaaatttgctccagagatttgcaattcccctccacta caacaacatacaaatcaaaatactgccaaacatctaaagtatacttattt gctactttatggggtgctcatcaacattagattcact (>MAGI4_8075 MAGI4.contigs_w_singleton.fas 4037 bp)

A suitable nucleic acid molecule of the present invention is a gene that is up-regulated by nitrogen and contained in a full-length cDNA clone having the nucleotide sequence of SEQ ID NO:4, as follows:

<u>GGACACTGACATGGACTGAAGGAGTAGAAAATACAGAACCCTGCAACTGC</u>

AAGCTAAGGAGAGTGTGATCACCAACAGCTAGTGCTAGTCCCCCTTCCTT

CCATCCATCC<u>ATG</u>GCATGCGTCAGCACCTTCCAGAGCTGCCCCATTGCCA

GAAGAGCAAAGATCAACACCAGGTCCAGGGGCAGCAGCAGTAGCGTGGCG

AAGGGGTCACCACCACCAGCCTTCCAGTTCCAGTGCAGGGCGTCGACTTT

CGCGGCGGACACCAGCCTCCGGCTCGAGCTGGACGAGAACCCCGAGGCGA

TCATCTCGGGGGCGTGGCCCGGGAACTGCTCCCTCCTCAGCTACGACGAC

CTCCGCGCCTACCTCGAGTCGCAGGAGACGGCGGCCCAGGCAGACGATCA

GCGCGGCGTGGCGCTCCTGAGCGAGACCATGTCCACACCCGTGCTGGTGG

CCACAGCAGACCAGACCCTGGAGGACGTCGAGTGCCACTTCGAGGCCGTG

TCGGGGCTTCCGGTCGTCGACAGCGGCCTCAGATGCGTCGGGGTGATCGT

CAAGAACGACCGGGCAAGAGCCTCTCATGGGTCCAAGACGAAGATATCGG

AAGTGATGACATCTCCAGCTATCACACTATCGTCTGACAAAACCGTGATG

GATGCTGCTGTTCTCATGCTCAAGAAGAAGATCCACAGATTACCAGTTGT

AAACCAGGACGAAAAAGTAATAGGTATAGTTACCCGCGCTGATGTTCTTC

GCGTGTTGGAAGGCATGTTGAAGATTTAGGAGCGCAGATACCCATGCTCG

GAAGCCACAGCCTCTTGTAAATATGTAGATGTGCCCGGGCATGGTGTTTC

TGAGTAGCAGCAAAGAGATCTACCATGTATAGGAGTTTCTCCTTGTAAAT

AATAGTAGCACGCCAGGAGACTCCATCCCAGG (Underlined=GeneRacer Oligo sequence; Bold/Underlined=start codon; coding sequence in bold) (Sequence of 5' RACE product CW13A08-Full_Length cloned into pCR4-TOPO) (derived from MEST13-A08, GB_ACC# BG840889)

The predicted protein or polypeptide encoded by the full-length cDNA clone of SEQ ID NO:4 has an amino acid sequence of SEQ ID NO:5, as follows:

MACVSTFQSCPIARRAKINTRSRGSSSSVAKGSPPPAFQFQCRASTFAAD

TSLRLELDENPEAIISGAWPGNCSLLSYDDLRAYLESQETAAQADDQRGV

ALLSETMSTPVLVATADQTLEDVECHFEAVSGLPVVDSGLRCVGVIVKND

RARASHGSKTKISEVMTSPAITLSSDKTVMDAAVLMLKKKIHRLPVVNQD

EKVIGIVTRADVLRVLEGMLKI

A putative promoter (upstream of the transcription site of the gene) for the gene of the full-length cDNA clone of SEQ ID NO:4 has a nucleotide sequence of SEQ ID NO:6, as follows:

caacgtggagtaggcaagcgttggtcttggccgaaccacgggataaacca ctgtgtcaactctgtgattgatctcttgtggtattgtgttttgttgagac tcttttctagccacttggcatttagtgtgctaacacttaacaagtttttg tggctataagtttaagttttacaggatcacctattcacccccccccctc taggtgctctcaagttgacaggtgtctccatggtgcctaattgagccgtt cttttacgctatccattcgattggtttggtgggtatgtgtggtctggctc ttgcgatgtttgcccgctggaaacgaaacaatcgtgcatacgtgcgcatg caattaacggtggtgttttggcctgtcttgcagcagcgggtgcagcatt ggcttggcataagcacgcaaccaaacaaagactaccttttggtcaatgca tgcgaagaatctgtacgagcgggcgtagacaaccaatgatgcgatataaa atttaaggattgaatcatattagaatcgagctttatttctattcattttc gaactaattttttaagtatcctaacttattgtgaagaaacgtaaatattt agatcccgatccattaccacctctactcatacgtgaaaccaaacacgcgg aatatccttctggttcaaatatgcagaagtcaatgagcaggacttctgct tgtttgttcagtctctcaggcagggttacaggaggcaatacaagatgttc tccaacgattccctgaatcgttcacccctctctcagtcctatgattcac tcactcacccctcccctcttctccgtatgacaggaaatcccctagagg gggagagctctaagctcccctccactaattaatcatatttactgtgaaa ttacctatttgtagtgtaattaatagttagcaatgtgtattacgtattat aaatattgtaccaatatttaaaactcaaaaaactaatgtataaaaatcaa atagtgcacttaaagtattaagggcagagctgaataggggggattgttgga gaagtgaagaaatagggggaagaatagttgagaagggtatttaaatatg aatagaaagtatgaatggagggaatgtttggagagagctcaagaacaagg gacactgagctgcctacaacacgtggcccttttttgtccctcttcttttttt ttctttcgcatctgctggctacaagaggacacgcccttctattcgccgta tagagcagtgtctgtgaagtaaaagagaactatcctccaaggcttatttt gagtgtattactcctggattcttgaatcttagctggtatggtatggtaag gagttacgttgtccaggagattccaacttacggatccacactgaaaagtt tgtattacccatttgttaggccccgtttcaatctcacgggataaacttta gcttcctgctaaactttagctatgtgaattgaagtgctaaagtttagttt taattaccaccattagctttcctgtttagattacaaatggctaaaagtag ctaaaaaagctgctaaagtttatctcgcaagattggaacagggcctata tggtcactttagagaggcatggaggtttaatagactatgacattcgtacg tggtcacctcaacaaactttattgtttgaccgaaccatagattgaattgt gtgacattgttctttgctcgtattattattaatagaaagtaaccttcttg ggtgcggcccatacggtcctgagcgcactaaatgaggcctcattggccgc ggcccattcgatcctcaacgcactggataaagccagcgtggcgtggctaa accacttcgtttggcatgggcctgtcggtgcacttgcccaaaccatgagc ttgtaccaaaactcgctagtggtagtggtattagtagtgaagaacttctg caacttcaaactcaccgattctctcgcggtcagtttggaagctaaaatat cggtggaaattagagagaatttgataagctaaaatctctttattatttaa aattgaataataaataaatttttaactcctccaatcttctccgttttatg tctcccaaactcagtgtaccagatcatattccttttcattaaaaaaaaggt gaacaaagacgccaccttatccactgccacgtgacagggggccaggggaa tctcggcggccagtggcggcacgccacgccggccggtcgccccgtcgct gtacaagatacccatgattggagcggggcaggtgcagagcagcaacgcca cggctgcatgagatcaagaagctgccttcacttcgcccactgcagcatgc cgtgtcgccgtcagagttgggcgcatatccagataaaaaaacttgcctg cttgcactgcagatgcgttgttttgctaacagcaagcaggcaagtcagc agcctaaccttctttgatatttacagagaagatgaaaaggagaactggag agcagtagtggcagtcacttcactggtcaagcattcctatccacctcggc ccacctccacctccctgacagtcattttgttatataaaacccatcaagct cccctgcaaggagatacagaaccctgcaactgcaagctaaggagagtgtg atcaccaacagctagtgctagtcccccttccttccatccatccatggcat gcgtcagcaccttccagagctgccccattgccagaagagcaaagatcaac accaggtccaggggcagcagcagtagcgtggcgaaggggtcaccaccacc agccttccagttccagtgcagggcgtcgactttcgcggcggacaccagcc tccggctcgagctggacgagaaccccgaggcgatcatctcggggggcgtgg cccgggaactgctccctcctcagctacgacgacctccgcgcctacctcga gtcgcaggagacggcggcccaggcagacgatcaggtacacttcgatctcg cggcttcttcagttcttgttaccattgtttacatctcctccagctcttgc taacccggcctggacgggtctcctcctctgtggatatatacagcgcggcg tggcgctcctgagcgagaccatgtccacacccgtgctggtggccacagca gaccagaccctggaggacgtcgagtgccacttcgaggccgtgtcggggct tccggtcgtcgacagcggcctcagatgcgtcggggtgatcgtcaagaacg accgggcaagagcctctcatggggtcagcacctcgctcctctccctccac ctctttctttctcatggggccagggccatgcatgcgcatcaagctgctag tttctcatagacaggcaaataagaacgacgtacgtccgttcagtttaccg gtctgtttctacttgtgacagtccaagacgaagatatcggaagtgatgac atctccagctatcacactatcgtctgacaaaaccgtgatgggtaatctttt

```
tttgcatcgcttttcttttcttttcttttcttttctgttcatgtgtgatt tttaacaagttgaatctaacagtgcatgcctaacgtctacagatgctgct gttctcatgctcaagaagaagatccacagattaccagttgtaaaccagga cgaaaaagtaataggtacggtgagtgagtgtcagaatgctcacaagccag cagagattaaaaaaaaaaactgcatgccatacacttaattagtattatcc ttaattatcattgacaacacagagattatatgttgcaagggctaatgggg ttctaaacactgtcaacaggtatagttacccgcgctgatgttcttcgcgt gttggaaggcatgttgaagatttaggagcgcagatacccatgctcggaag ccacagcctcttgtaaatatgtagatgtgcccgggcatggtgtttctgag tagcagcaaagagatctaccatgtataggagttctcc
```

(>MAGI4_31359 MAGI4.contigs_w_singleton.fas 3987 bp)

A suitable nucleic acid molecule of the present invention is a gene that is up-regulated by nitrogen and contained in a full-length cDNA clone having the nucleotide sequence of SEQ ID NO:7, as follows:

```
CGACTGGAGCACGAGGACACTGACATGGACTGGAGTAGAAACCCTTCTCG

CTCGGTTGCTCGGGAGCTTTCCCCTTCCTGTTCCTGAAGCTTCCGACATC

CGACCGCCTCCTCCTCCTCGTTCTACTCGCCGCCCCTTCTAGAATCATCC

AGAGGCGTGCCGGTGAAGCGCGAGAGCGGTGAGGCATGGCGATGCAGACG

GGGGTCGCGACCTCCAAGGTCCTCATCCTCGTCGGTGCAGGGATGACGGG

CTCGATCCTGCTGCGGAATGGCCGCTTATCTGATGTGTTGGGAGAACTCC

AGGAGATTATGAAGGGTGTAAATCAAGGAACTTCTTCGGGTCCCTATGAC

ATTGCACTTATTCAAGCTCAGATTCGGAATTTAGCGCAAGAAGTCAGAGA

TTTGACATTGTCAAAGCCCATTACCATACTGAATGGCAAATCTGACTCGG

GAGGCAGTTTATCATCCTACATACTGCCAGCAGCAGCAGTTGGAGCAATG

GGTTATTGCTACATGTGGTGGAAGGGGTTGTCTCTCTCAGATGTCATGTT

TGTCACAAAACACAACATGGCAAATGCTGTTCAGAGCATGTCAAAGCAGT

TGGAGCAAGTTTCATCAGCACTAGCTGCAACAAAAAGACATCTAACTCAA

CGGCTTGAGAATTTGGATGGCAAAATGGATGAACAAGTAGAGGTCTCCAA

AGCTATTAGAAATGAGGTCAATGATGTTAAAGATGACCTGTCTCAAATTG

GATTTGATGTCGAATCAATTCAGAAAATGGTTGCTGGATTGGAGGGAAAG

ATCGAGTTACTTGAGAACAAACAGGACGTGGCTAATACTGGTATCTGGTA

TCTCTGCCAAGTAGCAGGCGGTTTAAAAGATGGAATAAACACCAGGTTTT

TCCAGGAAACCAGTGAGAAGCTGAAGCTCTCACATTCAGCTCAACCTGAA

AACAAGCCAGTGAAGGGGCTTGAATTTTTTTCGGAAAGCACCATGGAACA

GAAAGTAGCTGACTCCAAACCAATTGCGGTGACAGTCGACGCTGAGAAGC

CTGAGAAACCGCTGCTGTAATGGGCACCACAGTGCACAGGTCTATCAGG

TTCTCATATCGGAAGGCAGGCCTTGCTTTGTGATCAAATCCTCTCCGCTT

GAGATGCACGTGGCCTTCCTGGTTG
```

(Underlinded=GeneRacer Oligo sequence; Bold/Underlined=start codon; coding sequence in bold) (Sequence of 5' RACE product CW15E10-Full_Length cloned into pCR4-TOPO) (derived from MEST15-E10, GB_ACC# BG841093)

The predicted protein or polypeptide encoded by the full-length cDNA clone of SEQ ID NO:7 has an amino acid sequence of SEQ ID NO:8, as follows:

```
MAMQTGVATSKVLILVGAGMTGSILLRNGRLSDVLGELQEIMKGVNQGTS

SGPYDIALIQAQIRNLAQEVRDLTLSKPITILNGKSDSGGSLSSYILPAA

AVGAMGYCYMWWKGLSLSDVMFVTKHNMANAVQSMSKQLEQVSSALAATK

RHLTQRLENLDGKMDEQVEVSKAIRNEVNDVKDDLSQIGFDVESIQKMVA

GLEGKIELLENKQDVANTGIWYLCQVAGGLKDGINTRFFQETSEKLKLSH

SAQPENKPVKGLEFFSESTMEQKVADSKPIAVTVDAEKPEKTAAVMGTTV

HRSIRFSYRKAGLAL
```

A putative promoter (upstream of the transcription site of the gene) for the gene of the full-length cDNA clone of SEQ ID NO:7 has a nucleotide sequence of SEQ ID NO:9, as follows:

```
taactctacaagctaagaatcaacatgtatgcaattccataataatcggg catcatctatcactcattgctaacttcagcactgaacatgatttcaagag tttttagcagaactactatgcgggtgatctcctttcagatgtagatggtt tagaagtgtacataagcttgcaggggcttaaggaactgtttatttaatct tctgtgagcacgaacatccatagaagaactatctgaactgaagctaaaga tttgcatgaaatggtaatttgtacacattaagtgcatcatgcaaacagaa cgagtacacagtgaaacgatacagacctcccgagtcagatttgccattca gtatggtaatgggctttgacaatgtcaaatctctgacttcttgcgctaaa ttccgaatctaatatcaagcacgagcatgcaaagttaagtagaaatgaat aattttaccgagatggaaagaagcaagagaaacttctaagcagatgctga cactgagatagtgagatgtaagatgtattccatatgaggaagagcatacc tgagcttgaataagtgcaatgtcatagggacccgaagaagttccttgatt tacacccttcataatctcctagaaacacaaaaggtacatcattgccttaa ataaacatttactaggaagtttcagagcataccatcaaaatctgtatgat atgtatcaggaatcactaactagtgaagcataagttatggtacgcaaaac ttccgagtgccaattgggcgttgatgtaattttatcacatggtgttaatc acatccacatagacagaatcaacgcttctagtacccatcgccaagtc attcaaaaaatatcaggtatcagctatctgacaacgctcaactatccaaa ccgtatgaaagtgcgtgtaatcaaaatgaacatatttttttcggggttgg gtgtgggggggtataccgacctggagttctcccaacacatcagataagcgg ccattccgcagcaggatcgagcccgtcatccctgcgaggacaccatttca ccacgtaaggtgtcgaaacaacagccgattggggaaaatagcatcaaatc cgagagagatttgatggggcgagaggtcgatggcggtgatgagaagagg acctgcaccgacgaggatgaggaccttggaggtcgcgaccccgtctgca tcgccatgcctcaccgctctcgcgcttcaccggcacgcctctggatgatt ctagaagggcggcgagtagaacgaggaggaggaggcggtcggatgtcgg
```

-continued aagcttcaggaacaggaaggggaaagctcccgagcaaccgagcgagaagg gtgcctggacccgggacccgggacctgagaatttcgtgtgtcacaaacaaa cagggtgaaccagttgtgaaatgggaccacgtgtcagtgaagaggtgagt agtagtatttgtgagttgtgactcgagaaatgccgctgcgggctgcggcc tagccacagccacgtcagcaatgtcgaaagtcgaaaccaaccccactcca cgtctccccaggagaagcgaccattcaaagccgccgggagctcggcgtc accgccgcgagctcgacacctcgacacctcgtgccgccgcagcgcttgct ttcgtcccccttacgccactcccacttggccacttcagccaccatctccc tgaagctagtggctaacctcctcaccgccatgggcacccctctcctcatc ccccttctcgtcaccctccagctgttcactacctcctccccgcggtcgc gtcgtcacacatctccgccatcatctcgcagtcgggcctcgacttcgcca aggacctgctcgtatcccatgccgttgcgaccctcacgcccatgaacgtg ccggacatcgagaggaccatgagcataccctcgtgggcaccgtccgcat ggccgcatccgggattgtgctccacggcctcgccgtcaccaactccaccg tcgctgtggggacgcgggtgttgtcgtggccgcctcgttggccagcgcg aacctcaccatggagtggaactactcgtatgacgcctggattgtgaccat atccgacagcgggaatgcttcggtccaggtataaatgaggggaacatata ctgtgcagtcatattagtgcaaccgtgcaattaagcaatgatgcatcgat ccaatcaaaatccaactatgattgctattttaggtggaacatggttagat gcaaaacagtcctgtttggttgatattcgatattccatcagttatgttcc ccaaggcgtggcttgctgattggtggctgttaattgaatcataagatact gcccgttttttaatatactgagtaggagatatacgcatctttatgcta ttaagtatagactgatcgcgcgacacttgaattttggaatatctattttc tgtcagatgtcagaagtagaatcaattatcttagaagtgggtgctaattc acacctattactatatttaaaatgggattaatataaacactctattttc tcgaaagcgcaagagagctgcgcgaaaatatattaagaagaagtaaaagg tccaaaaggaccccaagatacagataaggccgacctacggcggccaataa caagcataaatgaaaccatccatgacaaaaacactgctaccagaacagca ctacatctatctagctaacaggtagacctgggatagggcagtaagcaag gacagcttctttgcaccagccataacccaaagatcaatctccaaaccaac acttctaatagcaacagcaacactaggactcttattgtcaaaaacgtagc cattgcgatgtttccaaagggtccaaacaccaagaatgacaagagaatta agaccatttcttgcaatcccaggagtcttggtgatcaagtcttgccacca atccataaaaacctcttcacaggactgatgggccaagtgttgtagattta caagaagaagcagcttgaaccaaaattctctagcaaaaacgcagcccagc agcatatgatttaaggtttcctgatcctgatcacataatggacatctctc cggatgatccatacctcttctttgcaacctatcagctgtccacaccttct tgtgagcgaccaaccacatgaaaaatttagatttcggaggagcccaagtc ttccaaattatatgaaaaggctcaaactcaattgacccaataaagaaacc cctataagcttccttggaagaatattttccattggcagcaaggcgaaaga aatgcttgtcttcaacatgaggtcttagctgaaccaaatctaataaatcc cacaagaggagatactcgttgatacacccactgaa (>MAGI4_20155 MAGI4.contigs_w_singleton.fas 3385 bp)

A suitable nucleic acid molecule of the present invention is a gene that is up-regulated by nitrogen and contained in a full-length cDNA clone having the nucleotide sequence of SEQ ID NO:10, as follows:

<u>CGACTGGAGCACGAGGACACTGACATGGACTGAAGGAGTAGAAAAACTCC CAAATCCTTCGTTTCGTCGTCTCCACACGCAATAGCATCCGAGCAAAGAA GCCAAAGAGCAACTGGGAGCGAGGACGGGAGGCAACAAGCGGCGGCGGC<u>A TGG</u></u>ACCGGAACCTGAGCGGGTTTCTGATCGGGTGCCTGGGCGCCGCCGTG ACGCTGCTGGCGTACCAGCAGACGGTGGTGACCAGCACGCAGAGCGTCGC GGCGGGCTTCGTCGTCATCCTCTTCGCCCTCTTCGTCAAGGAAGGATTCA TTTCCCTCTGAATCTCTGGTGCGCGTCAGCCAGCCATGCATGAGGAGGCG TCATCGCTCCGCTGCCTGTATTTCTGCTCGCTAGTTCAGTCCCGCAGCTG CCGCTGTGCTCGTCAGGTTC (Underlined=GeneRacer Oligo sequence; Bold/Underlined=start codon; coding sequence in bold) (Sequence of 5' RACE product CW28B08-Full_Length cloned into pCR4-TOPO) (derived from MEST28-B08, GB_ACC# BG842208)

The predicted protein or polypeptide encoded by the full-length cDNA clone of SEQ ID NO:10 has an amino acid sequence of SEQ ID NO:11, as follows:

MDRNLSGFLIGCLGAAVTLLAYQQTVVTSTQSVAAGFVVILFALFVKEGF ISL

A putative promoter (upstream of the transcription site of the gene) for the gene of the full-length cDNA clone of SEQ ID NO:10 has a nucleotide sequence of SEQ ID NO:12, as follows:

gatacgactctcgctggtatataaaatctgtttcgtagataaacatgaaa ccagaattttgatcaccatatacttgtttcagaagcaaattggggacac catatacttgttgccttcaaacgaccgtacaataagttcagactgaccat ctgaatgtcacaagagctagtttagagcagcaagaaattgtcaagtgacc tagacatcccgaaccgacgcttcccagacttagcccgaccttccgggtcc ttcataagctgactccgtggcccctcaccagaccaacgcgcagccgttg accttgcggcttttatccccatccggccatccccaacccaactcccaaa tccttcgtttcgtcgtctccacacgcaatagcatccgagcaaagaagcca aagagcaactgggagcgaggacgggaggcaacaagcggcggcggcatgga ccggaacctgagcgggtttctgatcgggtgcctgggcgccgccgtgacgc tgctggcgtaccagcagacggtggtgaccagcacgcagagcgtcgcggcg ggcttcgtcgtcatcctcttcgccctcttcgtcaaggaaggattcatttc cctctgaatctctggtgcgcgtcagccagccatgcatgaggaggcgtcat cgctccgctgcctgtatttctgctcgctagttcagtcccgcagctgccgc tgtgctcgtcaggttcttggaaaaatactgtaatagcgtagtgactttta tgtacgacacggatggttgttgctggctgaagggtctactctgtcgaaat cgatgtatcttagtttatgctacttgaagaacagcagactgcagatcagc agagttcttgccttcttacgctaattaataattattggtacacgaatcct gattgtgttgagccttcttgccgttgctccttccctactaacatctcggc ttgccaattcacctatgtatgtttgctttgtatattagtgcaggtattaa tggccgcctgtaagtgagtttgttctcccttgttgaactaataaaattgg catgaattcaccccaaaaagattgatgctgtttctcactagttttcagcc tcagacgactatagatgtccaaacagtgcggaccgtccatttgaaacttg acccgtcacgattttagtccggtccaagcatggcaagcagggttggtaa cggcacgacctgtttagcgtgccgggtttgggcagctacagaggcccgcg tgttttggtccgatccgacacgagcaatgggccgacacagcggcggccca ttttcatatggcatatggtgccagcggccacacgccccccaaccaggc cacacacccgaaccctatctctaatcccctcaccccctcgggccctccgt ccccatctctagcgattcggcgccgtcgttctcgcccgttgcatcccgtc ggctcttgacctcgacggcggacgactctccatcgctgtcgtatgtggtg ctccgacctgcttggacttggagttcctccgtcctccctcgtcactccct ccgtctgcgactggggactccctaaccctaaccccctccggtctccggatt cggtggttctagctcctcagctgtgcaaggttcgttttatctcgtctaatc ccctccagatttggtgtctagctgatgtctggtgctcgtctgtggtgtct ggttgccgttgccggtggtcgtcacctgttgctcct (>MAGI4_8905 MAGI4.contigs_w_singleton.fas 1736 bp)

A suitable nucleic acid molecule of the present invention is a gene that is up-regulated by nitrogen and contained in a full-length cDNA clone having the nucleotide sequence of SEQ ID NO:13, as follows:

<u>CGACTGGAGCACGAGGACACTGACATGGACTGAAGGAGAGAAA</u>TCTTGGA

TCTGGTGGTGGGTTCATCCTTGGCCCACTTCTTCTTGAGCTTGGGTGCAT

ACCGCAGGTGGCAAGTGCAACAGCAACATTCGTATGATGTTCTCCTCCT

CCCTCTCTGTGGTGGAGTTTTACTTCCTGCACAGATTCCCCCTGCCTTTT

GCTGGCTACCTCATCTTCATTTCCATATTGGCTGGATTCTGGGGCCAGTG

TTTGGTTAGGAAGATCGTGCATGTGCTCAAGAGAGCATCGCTTATTGTCT

TCATCCTCTCCTCTGTTATCTTCGTCAGTGCTCTTACGATGGGTGTCGTT

GGAACCCAGAAGAGCATTTCGATGATCAACAATCACGAATATATGGGGTT

CCTCAACTTCTGCGAGTAACTAAACACCATCAGACTGTCGATCCGTCCG

GGAGAATCCAGGCCAATGCCTAATTGACCTCATCTCCCTCAAAATCTAGA

AGAATAAAGTCGCCGAGTATGTGCACAAGTTAGCTCCTCGCCAACATGTG

CGCATTTAGACCGACAGAGTCGCTGTAGTGAATTCAGCTCGTGTTAGCTC

CTGGCTAACGAGCTGACCATACGGCTTTAGTTTTGTGAAGTGGGCGCGAT

TTCGTCATGTCATGCATGTGTTAGCTCCTGGCTAACCTGCAAATGCGTGT

GTTGGTGCAGGTTTTTGTCACGTCTGCGTCAGCTCCTGGCTGACCAGCAG

TTGTTTGTCGTTCATTCTCTGCGTCAGCTCCTGGCTGACC (Underlined=GeneRacer Oligo sequence; Bold/Underlined=start codon; coding sequence in bold) (Sequence of 5' RACE product CW31A10-Full_Length cloned into pCR4-TOPO) (derived from MEST31-A10, GB_ACC# BG842452)

The predicted protein or polypeptide encoded by the full-length cDNA clone of SEQ ID NO:13 has an amino acid sequence of SEQ ID NO:14, as follows:

MMFSSSLSVVEFYFLHRFPLPFAGYLIFISILAGFWGQCLVRKIVHVLKR

ASLIVFILSSVIFVSALTMGVVGTQKSISMINNHEYMGFLNFCE

A putative promoter (upstream of the transcription site of the gene) for the gene of the full-length cDNA clone of SEQ ID NO:13 has a nucleotide sequence of SEQ ID NO:15, as follows:

cttgggcggtagagcttttattagcttttcaaaaagttcaaggtcatca aggtcagagtttaaatctaaaagctatgcctaaaatataaaatgggtcat actgagcacccatacatatgatgatcttgtccagtaccacatctgataca cacagagcattacggtgacccatgttccatatcttaaggtaacgaaggtt tgtcctaagttaaagttttgaaactttgacaacaatatctacaaaaataa ttattttttacttaaagaaattatatattgtgctagatgttttaataata aatataatagttttattttttatttagtcaatgtttatgaatattttgtta ttaatgataaaagtttcaaaattttgacttagtataaactttcgtgatct taagatagggaagagagggagtgagtaggtatcaattgcacccaggtaat gatcattttcaacggtcaaattactaaaaatagccgttaccaaaaactca acagtgtacatgatgtggagcgatccggggggagacacccacttacgttc aatgaaaatgctagtccacgaaggagacggaagcccaccctggcctctct ttgaggcgaagccacgttccggccaatcgtctcacagcctctatgcaggc tggaatgtcacccatgctgcacctcacctcaaccatcgtaaatcttaagg accattcttcttaattaactcatttgcaagggtttgtagcgccgctttac cttagtacatgtgttacagtaaacaaacaattgccagtgctttatatgat ttcgatccatcatattttaggtccaaaacagcatcttcactcaaagagac agattaaagctgtttggactgctttagctataataaaaatactgtagaaa aaacagaagtcggtggaagccgcagcgaacatgttctgattttcacggaa atacggcttgaaacgcactcggcttgcacaaacagaatgggaattgactg atatttacaatgttccatgcaacaaatatttgcagttttgcagcctagcc tggtgctagcgcaagaatgaacaacaaataactgctggtcagccaggagc tgacgcagagaatgaacgacaaacaactgctggtcagccaggagctgacg cagacgtgacaaaaacctgcaccaacacacgcatttgcaggttagccagg agctaacacatgcatgacatgacgaaatcgcgcccacttcacaaaactaa agccgtatggtcagctcgttagccaggagctaacacgagctgaattcact -continued

```
acagcgactctgtcggtctaaatgcgcacatgttggcgaggagctaactt
gtgcacatactcggcgactttattcttctagattttgagggagatgaggt
caattaggcattggcctggattctcccggacggatcgacagtctgatggt
gtttgagttactcgcagaagttgaggaacccatatattcgtgattgttg
atcatcgaaatgctcttctgggttccaacgacacctgaaactcaccgaaa
caagaggccattaggagagaagttaaaaatcaaactagattgatttagac
gaaacaagtaaaagagctaatataatgctacatccgttctcgaatatttg
tcgtccgttagttcattttttaaaatgaactaaaacgtgacaaataaaaa
agaacggagaatggagtgagtattccttaagattattttctcaaggatg
catgctataattgcaaaatcaatttaagcaacaccggtacgtttagttca
atttaagcaacaccggtacgtttagttcaattcaacttggagcggtatca
ggttagcaatttgccaagtttaaagctaagtagcaagtcaatgagttatc
aataggttcatacccatcgtaagagcactgacgaagataacagaggagag
gatgaagacaataagcgatgctctcttgagcacatgcacgatcttcctaa
ccaaacactggcccagaatccagccaatatggaaatgaagatgaggtag
ccagctgcagatagagaaacagtgcaagttattaactcgttaccatataa
caatcacacttatgaaaacgtctacattttgaggaattggaatctaacta
atagagtaggttatttctttagaacgtgacatttcataa
```

(>MAGI4_154269 MAGI4.contigs_w_singleton.fas 2189 bp)

A suitable nucleic acid molecule of the present invention is a gene that is up-regulated by nitrogen and contained in a full-length cDNA clone having the nucleotide sequence of SEQ ID NO:16, as follows:

```
CGACTGGAGCACGAGGACACTGACATGGACTGAAGGAGTAGAAAAAAGTG
CTCCCGGAAGACTCCAAGCTGCAGCTACCGGCCTTCCTCTCCCCATTCC
AATTCCGAGAACAGGGGCGGCGGAGTCAACCAGGTACGATGTGCTCGGTA
GCGAGGCTGGCGTTTGTGCTTGCACTGGCCATAGCCGCCTCGTCAATTGA
GGTTGCGGAGAGCAGAGATTTTAATATCTTTGCTCAGGGCAGCTTGCCTG
ATGCAACCAAGGGATCGTCTGGTCTAGCTGCAACCAGTGGAAAGTTGTGT
CAGTTATGCGAGCAGTACTCATCCGAGGCGCTCCTCTATCTCACACAAAA
CGAGACCCAGACTGAGATTCTTAGCATTCTACACCATGAATGTGCCAGCC
TTGCCCCTCTCAAACAGCAGTGCATCACGCTGGTTGACTACTACGTACCC
CTTTTCTTCTTGGAGGTCTCCATGGTTACCCCTGAGAAGTTCTGCGAGTC
GATGCATCTCTGCAAGAAGGGGATGAAGATTAGCCTACCCACCCGGGAGG
GTACTTGTGGTTTGTGCCACCATGTTGTTGTTGAAATTCTTATCATGCTT
AAAGACCCCAACATGCAGCTGGAAGTAATCGACCTACTCACCAAAACATG
CAGCAAGGCGCAGAACTATGAACAGTAGTGCAAGCGGCTGGTCCTCAAGT
ATATTCCACTTATTCTGGTGAAGGGCCAGAAATTCCTTGAGACAACGGAT
GTCTGCTCTGTGATACATGCATGCAAAGCAGGCACACAAGCATCAATGGA
AGCCATGCCTCTGTCTGCCATGTTGTGAAGGTGATGCGA
```

(Underlined=GeneRacer Oligo sequence; Bold/Underlined=start codon; coding sequence in bold) (Sequence of 5' RACE product CW42B12-Full_Length cloned into pCR4-TOPO) (derived from MEST42-B12, GB_ACC# BG873755)

The predicted protein or polypeptide encoded by the full-length cDNA clone of SEQ ID NO:16 has an amino acid sequence of SEQ ID NO:17, as follows:

```
MCSVARLAFVLALAIAASSIEVAESRDFNIFAQGSLPDATKGSSGLAATS
GKLCQLCEQYSSEALLYLTQNETQTEILSILHHECASLAPLKQQCITLVD
YYVPLFFLEVSMVTPEKFCESMHLCKKGMKISLPTREGTCGLCHHVVVEI
LIMLKDPNMQLEVIDLLTKTCSKAQNYEQ
```

A putative promoter (upstream of the transcription site of the gene) for the gene of the full-length cDNA clone of SEQ ID NO:16 has a nucleotide sequence of SEQ ID NO:18, as follows:

```
gcactcatagcacatctgaggttccctttcttgaacttagctcacctact
gttcatagttctgcgccttgctgcatgttttggtgagtaggtcgattact
tccagctgcaagcttgcagcaaacaaagaaaggcattacagtatgtacag
agtacagagcagtacaacacagaagaatgttggtgacagatagtgaaaat
atggttattacctgcatgttgggtctttaagcatgataagaatttcaac
aacaacatggtggcacaaaccacaagtaccctcccgggtgggtaggctaa
tcttcatcccttcttgcagagatgcatcgactcgcagaacttctcaggg
gtaaccatggagacctccaagaagaaaagggtacgtagtagtcaaccag
cgtgatgcactgcagcagggtgaatcatcaacacaacatttaacacagct
gaaaacgtggtaccaatggaaggatcacaagttacctatacctgctgttt
gagaggggcaaggctggcacattcatggtgtagaatgctaagaatctcag
tctgggtctcgttttgtgtgagatagaggagcgcctcggatgagtactgc
tcgcataactgacacaactttccactggttgcagctagaccagacgatcc
cttggttgcatcaggcaagctgccctgagctgaattgaagacagaagaaa
ggattggccagaaatgcaaaacttcagaaaaacttgagttcctgtgagga
atagcagctaagctgaagctacgccctctacattgagtagaactgatggc
ttagacgtaattgctttctttaacatgtcaccggactaaatgaagatacg
aacttgtcaaacaaagaaggaatttagataaactaattgaaactatcacg
agatctccatcgaaaagaaactatcactagacctgataattcactgctat
ggatcaacattcaacaaagaataaagagagtaaggagcaaaaatcagtag
attgaaagcttaccaaagatattaaaatctctgctctccgcaacctcaat
tgacgaggcggctatggccagtgcaagcacaaacgccagcctcgctaccg
agcacatcgtacctgcttaccactaccagttggtcagttgacaggaacaa
aactactgcttgaagaaaactatcgcagtgaaatcagctgtggctgatgg
acgcagaaaagctggcttgctcaaagcttctccataaagccaaaaggtaa
ccaaaaaaaaagagaaaggaaatgtatcctagggccctctctctacgtc
atgtaacggatcagtagaagtttcagattcattcagcccgacgtaactga
agaattcagttcgcttcaagatgtagccatcagattcacgtatttggagt
caagccaagatagtaccaattggtccgcatccacattccaggcaacagat
```

```
tcacgagattcagctcgctccacgccagcagagctgctactattctggca ccactccaaatacgcctttgcagcagattagcaaagcattttacgctcgc ttttgcgctttattttgcccctcgtttccttttccaggtagcttccggttc cgaagaatcggaggtccttggattcagggacaaggggtcgaactgggcag caaatcaagaaccgaggggagacggtagtacagagagcccaggagaagct aacatatgaatggggaattaaagacgcatctcacctggttgactccgccg cccctgttctcggaattggaatgggagagaggaaggccggtatctgcatc ttggactcttccgggagcactttgttttcttaaagcttcgtgttacatta agaagatgcatgagcatgtagaacagtgtgtggccgtgtgtgagaa cctgagatattttgcttctttggtggccaagatgtgttagaaaggcata atcttttctta
```

(>MAGI4_114997 MAGI4.contigs_w_singleton.fas 1961 bp)

A suitable nucleic acid molecule of the present invention is a gene that is up-regulated by nitrogen and contained in a full-length cDNA clone having the nucleotide sequence of SEQ ID NO:19, as follows:

```
CGACTGGAGCACGAGGACACTGACATGGACTGAAGGAGTAGAAATATAGC

CAGAACTCTTGCATCCTGGTGATGGTAAACTGCCGTGCCAGTATAAACGC

GAAGGCAGGTCACACATACTCACAAGTCCGTCCCATCTCAGGTCATCCAT

CCATCCATCCCTGCAGCAATGGCGTCTGCAGTGACCAGCAGCGACAAGGA

GCAGGCCGTCCCTACCATCGACGCTGACGAAGCGCACGCGCTGCTGAGCT

CCGGCCATGGCTACGTGGATGTCAGGATGCGGGGGGACTTCCACAAGGCG

CATGCGCCCGGTGCTCGGAACGTTCCCTACTACCTGTCCGTCACGCCGCA

AGGGAAGGAGAAGAACCCACACTTTGTAGAGGAAGTGGCTGCCTTCTGTG

GGAAGGATGATGTCTTCATTGTGGGTTGCAACACGGGGAACAGATCCAGG

TTCGCGACGGCAGACCTTCTGAACGCGGGGTTCAAGAACGTGAGGAACCT

GCAAGGTGGTTACCGCTCCTTTCAGCAGCGAGCTCAACAGCAGTAGACAT

CACGTCCTGAAGGTATGCCAGGGATGCTGCAGTTGAACG
```

(Underlined=GeneRacer Oligo sequence; Bold/Underlined=start codon; coding sequence in bold) (Sequence of 5' RACE product CW43D12-Full_Length cloned into pCR4-TOPO) (derived from MEST43-D12, GB_ACC# BG873856)

The predicted protein or polypeptide encoded by the full-length cDNA clone of SEQ ID NO:19 has an amino acid sequence of SEQ ID NO:20, as follows:

```
MASAVTSSDKEQAVPTIDADEAHALLSSGHGYVDVRMRGDFHKAHAPGAR

NVPYYLSVTPQGKEKNPHFVEEVAAFCGKDDVFIVGCNTGNRSRFATADL

LNAGFKNVRNLQGGYRSFQQRAQQQ
```

A putative promoter (upstream of the transcription site of the gene) for the gene of the full-length cDNA clone of SEQ ID NO:19 has a nucleotide sequence of SEQ ID NO:21, as follows:

```
cgcactaagaaggcagggaattgtgtggcaaatataggtacatgctacac gtgtgatatttcccgatttgtcaatctgggacatgaagttaacatcgcaa attataatgttacaggaaccaggtatggtgctagcttgcgtaagcaaatc aagaagatggaggtatctcagcattccaagtacttttgcgagttctgtgg gaaggtacatttctgttagttaccctgtttctgcatccaagttttctaat ctttgatctattgaactgcgagctgtctttatgttgtactcgttatcatc accactgctgttatgaaatgtaggctgcagtcagattgattttgagcaca tgaaatcaattagtttttcgatatatctgtttgtcacaagcacatgaaatc aattagtcttcgatatatctgtttgtcacatttgaatgatttataagatg tctgggcatgtccatcaatgtgtttctaagatacatttgaagacagacag catttgttccgaatccaacctttgctgtgctgtgtttccagtttgctgtg aagaggaaagcagttggaatttgggggtgcaaggactgtgggaaggtgaa ggctggtggtgcttacaccatgaagtaagtaattcttcgcctgtccgaaa accacaatttgttagccacggctaaattctgttaatgtgtttgcagcact gctagtgcggtcaccgtcaggagcacgatccgccgcctgagggagcagac tgaagcatgatatagctctttatattattggggtttcctgtagttgctct tgtcaggcatgttgtgggggccttatctagtggaaatgtggaatcactgt actggctgttttgccgagacaatgctccttatatttggtttatgctctag gatctcaaagttgtgttaagatttgcccttggttaccgttctgaatctga caagtgatatttcatcctatgccatcttgacgtcgaatttggttgtggtt ttctatgcgcttggctgtgtcaatggtttgctattctgttcttgaaattc tacagatactgctgcgtctctgctggttgagtctggtttagatagcaacc agtccttattattggtcttttcaagttcaagtcaactaaaatgcgacaaat aaaaaaagaatggagggagtatataactgttcaagtcaaccaatcctta ttacgcctgcacttgtgtccaaaaagaaatgccccggagctattattggt ctgttgccagataagcagtgacgacgcagcatcgaaggtcagagacgact tttttgcgagaacgagcatcaagctgacggaatggagcattattccgata aaaaaaaggtatagccagaactcttgcatcctggtgatggtaaactgccg tgccagtataaacgcgaaggcaggtcacacatactcacaagtccgtccca tctcaggtcatccatccatccatccctgcagcaatggcgtctgcagtgac cagcaggtaaacatagcttctgagtgcatctgatgttgcttacagtaaca ttacatgcatagagcagaagatcggatgcatctggattaaccagagtcag tcttgtcttggtgtgcactgcagcgacaaggagcaggccgtccctaccat cgacgctgacgaagcgcacgcgctgctgagctccggccatggctacgtgg atgtcaggtgcgtagagctcagccagtcagggacgcgcctatgcgtgtgc tggagcttccagacgaactgacgctgacggggacgaggtggttctccttc gtgcaggatgcgggggggacttccacaaggcgcatgcgcccggtgctcgga acgttccctactacctgtccgtcacgccgcaaggtcagtttcttgctcgc tggcgttggcgctggcactggcattggggttattgatttgagctgcctct gtccccgtgtagggaaggagaagaacccacactttgtagaggaagtggct gccttctgtgggaaggatgatgtcttcattgtggtagctattcactcata
```

-continued taaataaataaataaatgtactagtactctataaatagatagatacgcct gtaatcaaggagttgtcgtgtagggttgcaacacggggaacagatccagg ttcgcgacggcagaccttctgaacgcggtaaacacagcccatccgagctt tagcatcaatccagttagctgtatgtgtgtgtgtgtgtgtgtgtgtttaa ctgagggtcacactagtctgctcgcat (>MAGI4_143540 MAGI4.contigs_w_singleton.fas 2277 bp)

A suitable nucleic acid molecule of the present invention is a gene that is up-regulated by nitrogen and contained in a full-length cDNA clone having the nucleotide sequence of SEQ ID NO:22, as follows

AAGATAGCTGCAAAACAAGCGAGTTACTTACAACCAAACAGAAGGGTAGA

AACCACCTGAAGCC<u>ATG</u>TGCATTGCTGCATGGATTTGGCAGGCTCACCCT

GTGCACCAACTCCTCCTGCTTCTCAACAGAGATGAGTTCCACAGCAGGCC

TACAAAAGCAGTAGGATGGTGGGGTGAAGGCTCAAAGAAGATCCTTGGTG

GCAGGGATGTGCTTGGTGGAGGAACATGGATGGGGTGCACCAAGGATGGA

AGGCTTGCCTTCCTGACCAATGTGCTTGAACCAGATGCCATGCCCGGTGC

ACGGACTAGGGGAGATCTGCCTCTCAAATTCCTGCAGAGCAACAAGAGCC

CACTCGAAGTTGCAACTGAAGTGGCAGAAGAAGCTGATGAATACAATGGC

TTCAACCTCATACTAGCTGATCTAACAACAAATATCATGGTTTATGTGTC

AAACCGGCCTAAGGGTCAGCCTGCAACAATTCAACTCGTGTCACCAGGAC

TCCATGTGCTGTCCAATGCAAGGCTAGATAGCCCTTGGCAGAAGGCAATT

CTCCTCGGTAAAAACTTCAGGGAGCTTCTTAGGGAGCATGGTGCTGATGA

GGTTGAAGTGAAGGATATAGTTGAGAGGCTAATGACTGACACCACAAAGG

CTGACAAAGATAGACTGCCAAACACTGGTTGTGATCCCAACTGGGAGCAT

GGTCTGAGCTCCATCTTCATTGAGGTGCAAACTGACCAAGGGCCCTATGG

GACACGGAGCACAGCCGTTTTATCAGTGAACTATGATGGCGAAGCTAGCT

TGTACGAGAAGTATCTTGAGAGTGGTATATGGAAGGATCACACAGTGAGT

TACCAGATAGAGTAG<u>TAG</u>TAGGCATTGCACAGGAAAAGTTGGCGACCTCA (Underlined=start and stop codons; coding sequence in bold) (Sequence of 5' RACE product AM45C08-1T3 Full_Length cloned into pCR4-TOPO)

The predicted protein or polypeptide encoded by the full-length cDNA clone of SEQ ID NO:22 has an amino acid sequence of SEQ ID NO:23, as follows:

MCIAAWIWQAHPVHQLLLLLNRDEFHSRPTKAVGWWGEGSKKILGGRDVL

GGGTWMGCTKDGRLAFLTNVLEPDAMPGARTRGDLPLKFLQSNKSPLEVA

TEVAEEADEYNGFNLILADLTTNIMVYVSNRPKGQPATIQLVSPGLHVLS

NARLDSPWQKAILLGKNFRELLREHGADEVEVKDIVERLMTDTTKADKDR

LPNTGCDPNWEHGLSSIFIEVQTDQGPYGTRSTAVLSVNYDGEASLYEKY

LESGIWKDHTVSYQIE (The above sequences are presented after trimming GeneRacer Oligo sequence. Cloned in pCR4-TOPO wctor at the "TOPO Cloning site".)

A suitable nucleic acid molecule of the present invention is a gene that is up-regulated by nitrogen and contained in a full-length cDNA clone having the nucleotide sequence of SEQ ID NO:24, as follows:

<u>CGACTGGAGCACGAGGACACTGACATGGACTGAAGGAGTAGAAAA</u>TCAGC

CGCAGTCGCGTCGCGTCGCGTCGCGTCCAGTCCAATCCTCGGAGCCTCAC

ACGGGCGGACGAGCGGGAGCTTCTCCCAATCTCCCCTGCCCTGCCCTGCC

CTGCCGCCGCGCTTAGCTTCGCATCTTCCCCTCCTCCTCCTCCTTCC

TCGGCCAAGCGAGGAGCGAGGCGCGGGCGCGAGCGCGTCGTTGAG<u>ATG</u>GA

TTCGGAGGCGGTGCAGCACGGCCTTCTCCCTCTGTCTGCCTGTCCTCCTA

CCGCCAACAGCTGCGCGCATTACAGCCGTGGGTGCAGCGTCGTGGCGCCC

TGCTGCGGCCAGGCCTTCGGCTGCCGCCATTGCCACAACGACGCCAAGAA

CTCGCTGGAGGTCGACCCGCGCGACCGGCACGAGATCCCCCGCCACGAAA

TAAAGAAGGTGATCTGTTCTCTCTGCTCCAAGGAACAGGACGTGCAACAG

AACTGCTCCAGCTGTGGGGCCTGCATGGGCAAGTACTTCTGTAAAGTATG

CAAGTTCTTCGATGATGATGCCTCAAAGGGCCAGTACCACTGTGACGGAT

GTGGAATATGTAGAACCGGCGGCGTGGAGAACTTTTTCCACTGTGATAAA

TGTGGGTGTTGCTACAGCAATGTCTTGAAGGATTCCCACCACTGCGTCGA

AAGAGCAATGCATCACAACTGCCCCGTCTGCTTTGAGTATCTGTTCGACT

CCACGAAGGACATCAGCGTGCTGCAATGTGGGCATACCATCCATTTGGAG

TGCATGAACGAGATGAGAGCACACCATCACTTCTCATGCCCAGTGTGCTC

GAGGTCCGCCTGCGACATGTCGGCCACATGGCGGAAGCTCGACGAGGAGG

TCGCGGCCACGCCGATGCCTGACATCTACCAGAAGCACATGGTGTGGATC

CTGTGCAACGACTGCAGCGCGACCTCGAGCGTGCGGTTCCACGTGCTGGG

GCACAAGTGCCCCGCGTGCAGCTCGTACAACACCCGGGAGACGAGGGCTG

CGTGCCCCAGGATCTGAGGCGAACCAGAGGCCATGTCACAAAATGCCAGG

GAGATGCCGTCCAACGACCATCTGTCTGCAGGACGTTGCTGCGCTTAAGG

TTAAAGGCTAGCGCGAGACCAGGCCTGGTAGTCCAGTCTTGAGTTTGGTG

CTGGAGCATTTGTAATGTTCCGGTAAAATGTAATGCGTCCATGAGTGCTG

TCCAGGCAGTAAGCACACCTGTGGATCGGGGCCGGCGCAAGGTCCCTAGG

CAAGCTGCAGGATTAGTGGGGCTATTCATGTTTAGGGCGCGAATGCAACG

A (Underlined=GeneRacer Oligo sequence; Bold/Underlined=start codon; coding sequence in bold) (Sequence of 5' RACE product CW55C10-Full_Length cloned into pCR4-TOPO) (derived from MEST55-C10, GB_ACC# BM072886)

The predicted protein or polypeptide encoded by the full-length cDNA clone of SEQ ID NO:24 has an amino acid sequence of SEQ ID NO:25, as follows:

MDSEAVQHGLLPLSACPPTANSCAHYSRGCSVVAPCCGQAFGCRHCHNDA

KNSLEVDPRDRHEIPRHEIKKVICSLCSKEQDVQQNCSSCGACMGKYFCK

VCKFFDDDASKGQYHCDGCGICRTGGVENFFHCDKCGCCYSNVLKDSHHC

VERAMHHNCPVCFEYLFDSTKDISVLQCGHTIHLECMNEMRAHHHFSCPV

CSRSACDMSATWRKLDEEVAATPMPDIYQKHMVWILCNDCSATSSVRFHV

LGHKCPACSSYNTRETRAACPRI

A putative promoter (upstream of the transcription site of the gene) for the gene of the full-length cDNA clone of SEQ ID NO:24 has a nucleotide sequence of SEQ ID NO:26, as follows:

ccttacaggttatcacttaccgcctccgttttcgaatatttatcgttcgc tagttaatcttaatttaaacttaaatgaggcaaataaacgtttaaactat tctcttgatcgtgtgtctgattgtcttgttgtttaaaatgcctcctagat cgatcgtcgtagtgcaggttgttttagacaaagttgaactgcgatcagac cgagaccggacaaccattgagcagttattttcctattcatcgtggactaa ctggaagatattttctgagctccaaaaaatatccaaaggaagggagaacg tgaaggacgaggtcggaccggacacgcctcccctcgctaatcattgaggc ggaggcggcggaggcgattttgggaacactcgcaggtagattttgcgtga acttggacgagggtcattttcgctttggatgaatccacgaggtggtgtca ctgcacgcgcacggggccctcaaaccgtttgaaaaccaaaccgaaggcaa caaaacgagactctcatctcatctgactctacggccagctcaagtgatct gctgctggtggccgacctggcggcgtgatctcgctcccgtgcccgtctcc tccatccgacgcgtacatggcccgccatcctcatccatccgcctccaga ggaccagtccagaccaataataaaagggaaggtcgacgacgggctcgctc caatccggcgaaccgcgtcccgtcagcctgtcatccgtgggcgcgcgg ctgtcgacctgcgcatcagcttctatgattagccaggagcaataatttat tactcctatttgccaggcgacgttcgtccaattcgacccggcaggcagca ggcagcagctgtgctcctgtgggtgggtgggtcatgggtgaccacatgca tcgatggagccagggccgccgtgtgcgcagccaactctacctatccccgc ccccgggatgggcgatggcaactatcctatcgcaacaatatcctggggtg ggggctataaaacggagcggcccgcgtggggcgcgcctccatcagccgca gtcgcgtcgcgtcgcgtcgcgtccagtccaatcctcggagcctcacacgg gcggacgagcgggagcttctcccaatctccctgccctgccctgccctgc cgccgcgcttagcttcgcatcttcccctcctcctcctcctccttcctcgg ccaagcgaggagcgaggcgcgggcgcgagcgcgtcgttgagatggattcg gaggcggtgcagcacgggtaagcaagcaaagcaatccatggatcgatcca ggacacaggaggagctaggaagaggaacaatctcatgatctcattcatc tgacacagccttctccctctgtctgcctgtcctcctaccgccaacagctg cgcgcattacagccgtgggtgcagcgtcgtggcgcctgctgcggccagg ccttcggctgccgccattgccacaacgacgccaaggttcggtggtttccc tccttccgttttcgcttcggctccggttcagcagatgttctgaaacaacc ctgtcccgtgccccggcagaactcgctggaggtcgacccgcgcgaccggc acgagatccccgccacgaaataaagaaggtcagcgttccctccctctgc tcaaagagcaatctcctgcctgtttcaaccattgcctatctcgtgttcgt ctttgttattaccgtgagcaaagaaaggaagaaacaaacaagagcgccgc cttctctcttctccttctccatgtaatggagcatttgttccgccgcgtag tcgagtgcaagcagcggttttcctcttttggaaacccaccccccacgcacg gttccgttccaatctcgcccttccaattgaccaacacaaacctttcctaa gatttcttgtcctccttacccttctacagacaagtacgaaacgcaatcgc acaaggttatactactactagcttttagtgttctagcgaccttagatttt ttttttggttaggcatccctgattttctcacacttaaaagcttcttca gataaggccatatcagctcagctcagtgctctgggagccgttctgcactt cacttgcgtgtcactaaaaacttgactgctttccgcgatgtgctccgcac caagtggccggcactgcgtggtccacaggattttcaagagaaagccggg gtcacgggtgccacttgaagccaaggacaggcgtctgggattggagaata tatgagaaagggataccgtcagaggcacatctcaccgtcaaactgaacag ggtctaactgcttccagctgatttgattgagtttgagtgctgcatagttg aggacctggatatagtgacgtgtcctgacaggtgtctttggacctattag cagtgaatctgacgtcgatcggctaaagcaatcatgttcgattcttatcc ttttttttttgagagtatatgcctgattcgataaacgttcctatcctgtt tcctgatgatgcatatatgttgtttcgattcatatagaatcataccatcc atctattttgtttaaaaaaaaaatttctgggtggccatgggcacagcatg cctgttcttaagataacgattccagtaactgttcccttctgtcactgaac tcatatgaatcgagacttaactggagctgttgcgcaggtgatctgttctc tctgctccaaggaacaggacgtaagttgtctaccaaaacgtactcctaca acagttttttcaggagcacgcatcttttggctgtactactactgctaactg catggaaactgctcattcccatcggcaggtgcaacagaactgctccagct gtggggcctgcatgggcaagtacttctgtaaagtatgcaagttcttcgat gatgatgtaagcgtactcgaatcccagacgatgaacaaagaaactgaact cgatgcgttgtttactgcgtttctttttttccccttcttcttcacgtaca tactgtactgctcttggtccaggtctcaaagggccagtaccactgtgacg gatgtggaatatgtaggtaagcaccaccacgctgatggctacgtctaaag acttgacgcgcagaagtgtaaaacttctgtcagccgttcaaaactgataa attcgggttcctcgtcttcttgttgtttatgcagaaccggcggcgtggag aacttttccactgtgataaatgtggtgagtttctgcgcggacttctttc tgctaagattctgtaaccatgctatgcagcaaagatttcactcgcgccct tattggtgtccttgttgccgtccgacagggtgttgctacagcaatgtctt gaaggattcccaccactgcgtcgaaagagcaatgcatcacaactgcccg tctgctttgaggtgagagacctccgtttcaacggaacattcactctgaat gttccaatctcttgatattgagaaggtttccctctgtttttttttcacagt atctgttcgactccacgaaggacatcagcgtgctgcaatgtgggcatacc atccatttggagtgcatgaacgagatgagagcacaccatcagtaagcata tataccgttctcttcggagctgagaaacggtgccacctcacaacatcctc ttttagtcgcagtgaccttacagtctcagccctgtttggtcttggcagc ttctcatgcccagtgtgctcgaggtccgcctgcgacatgtcggccacatg -continued gcggaagctcgacgaggaggtcgcggccacgccgatgcctgacatctacc
agaagcacatggtaagaagccgaccgcccactcgttcgtcgtcccgttac
atcttttccacagccatggctcgctgtttgacgagctctgaacctgtccg
gggtgccgattgctggaactgaacggcaaatgaacgctgtggtgtgagtg
caggtgtggatcctgtgcaacgactgcagcgcgacctcgagcgtgcggtt
ccacgtgctggggcacaagtgcccgcgtgcagctcgtacaacacccggg
agacgagggctgcgtgcccaggatctgaggcgaaccagaggccatgtca
caaaatgccagggagatgccgtccaacgatcatctgtctgcaggacgttg
ctgcgcttaaggttaaaggctagcgcgagaccaggcctggtagtccagtc
ttgagtttggtgctggagcatttgtaatgttccggtaaaatgtaatgcgt
ccatgagtgctgtccaggcagtaagcacacctgtggatcggggccggcgc
aaggtccctaggcaagctgcaggattagtggggctattcatgtttagggc
gcgaatgcaacgaaattacccgtgggccgtgggctcggtatgtaacagaa
ccgattatttctattacaataataacatgcagttctattgggccgagcct
aatcaggcaccacgaatgtgaataattgcacatggcgcatatatggcggg
cagtagatacatataaaatggagaaaatccgtttattgccatcaaaactt
atactgatcactacaataccatctaaaatgatgtgctcccttcaaaacca
ttggtttatattttctatcctttcattgccattgccgttacataatggcg
catgtggcatatatgggcggcgtatgtaggttcaggatggtcacacgaca
tatgacgagactacagagacatggtcaagagaagttcagtggattgtgac
attctgatctaagacttcttaaaattggagttaataagatcgataatact
cgtaccaataatgcacatcttgcttttagaagcctgttttgaaataacc
ccaggattaagcatgtttggcccaaagaaattttttgtgatggtggtcgac
cgagaagttttcttgactgcatgccagtgaggacaaaaaaacacatatga
aagaatcgtgttggtctgtgagaatagatcaggaagttttctcgactgcg
cgaccatggatggtggggtgtttcatcaaggatccgctttaaacacata
cctttttgccttggtgatggataaggacataccggacataaaggggataa
cccttggtgtgtgttttttttgcagacaatgtaatgctagttgatgaaagt
cgggcatgagtaaatggaaaactagagttgtggcaagaaactttataatc
aaaaggttttagacttagtagaactaaaatagaatatattggatgcgatt
tcagcactacatatgaggaatgagatcttagtttagaaggtctaggaagg
acaccttagatatttagtatcagcctatagagagaccgggatattaatg
aagatgctagccataaaatcaaagtagagtcagtgaagtggagtcaagca
tctggcattttatatgacaaagtgggaattgcaaaagctaaaagaaagt
tttaggacaacgattagaccttctatattatatggaacataattttagcc
tacaaaaagatgatatgtttagcagataaatgttgcggtaatacatatgt
tacgttggatttgtgaacatacaaaaagggatcgagtttagaatgatgat
atacatgatagactaggggtagcaccagtcgatcgatatggtttgaatat
atccaacggagacctatagaggtgtcaatatgtcttaggacctgtttgaa
agcatccagttttttaagaaattggtttatagaaattaaagtggttccaaa
catacaagtttatgccccagtttatataaactggattatcaatttcttaa -continued aaaccaagaagctagtctttgctagctaaaaccaacttttgcttgtttaa
ttacataatgcccttgttggttgcatggaatttacatctattgtcgtcgc
ttttaagatagaggaagggtatgttagtaattgtgtatcaaaaaatagaa
aatttgtttcttagaactaagttccaaacaccctcacctaactttttttat
aaactagtttctataaactggagatagaaattggttttttaataaaccggt
atgctttcaaacaataccttaggattctaagatgtgataccaatgagaaa
aggaagaggaagactgaagttggtatgggaggtgataataaaatgagtct
tgaaaaaatgagatatatctaaagatttagccttgaatagaaatgcatga
aataactatccatatgtttgaaccttgactttgagttttgttgaattttt
taactctagcctacgccaatttgtttgggactaaaaggttatgttgttgt
tattgccgctataaatggtgttcaacactttcttcaagattatgatatt
tgttttctacaccaacaatattactgttggggtctccttctctgccgaag
gtcctcaggatgaagaaactgtctttggttcatcttggtaagatacgtca
aaaggaccgaatgccgaagctgtgacagacatgcagggaatatagcagag
cttcgataagagttaaagcttcggcttaagatgattatgaaggtcataca
agaaaccaagccaccaatgaaaagacctgtttatccttaaaatttgtatt
agaacaatgtatagatatcagggtcataaatgtacttttgcttgggcggc
gtcccgtgcctataaatagatgaactgtaccccgtactgttgacacttt
cattgaaagtcattctcgcactctctccttcaagcaagacgaaggtacta
atgtaatataatgtttgtaatggttcattagaatgttatccaaactatgt
cattactttgatatagaaataaagtgaattcataagataataccacatt
gtgatattatctccatgagaaatgaagatccgctcttcttcaccttcgcc
caaaaaccattatctttgagagaagataattgaaaggaaattgggttaac
catttcctataactaattttggtgggtgatgatcaacacaaacccatgga
ctaactagtttgtctagaattcatggattacaggtgcataaggttcaaca
caaaccaagaaagaaatccggttagggacacaattaaaaatggagcaaag
acttga (>MAGI4_73717 MAGI4.contigs_w_singleton.fas 7106 bp)

A suitable nucleic acid molecule of the present invention is a gene that is up-regulated by nitrogen and contained in a full-length cDNA clone having the nucleotide sequence of SEQ ID NO:27, as follows:

<u>CGACTGGAGCACGAGGACACTGACATGGACTGAAGGAGTAGAAAGCTGCT</u>

<u>ATTTTCTTCTTACATTGTCCACTGCGCTAGCTAGCTCGCATCTACCTGGA</u>

<u>AAGCTGAAAGCTAGCCAGAGCGCTAGCTAGCTTCGTTCCTCGTCGCCGCG</u>

<u>CGCCGGCCAG</u>ATGACTGCTCACCAGACTTGCTGCGATGATGCCGTTGCCG

CCGGCACTGCACCGGCTGCCAGGAGGAGGCGCCTCAAATTGACGAGGCCG

TCGGCCTCGCTCTTGATGGCGAGGAAGCTAAGGAAGAAGGCTGCCGGCAG

CAAACGCCCAAGGGCGGCAGCGTCGAGGAAGCGCGCGATGGCGATCAGGA

GGAAGATGGAAGCGCTGAGGCTGCTCGTGCCACTCTGCGGCCGAGACAAC

-continued

```
GGCTCGGTGACCGGTGGGGCGGTCGAACGACTGGACGAGCTCCTCATGCA

CGCCGCCGGGTACATCCTGCGCCTCCAGATGCAGGTCAGAGTGATGCAGC

TTATGGTCCATGCACTAAATGACCGGCCCGAGGATTAATCTTCTTCCCAA

GACCATGTGATCTTCCTTCTTTAATTTCTTCTTCATCTTCTTCGCGTGCC

TGTGTTGCACGAGGCAGCTGTGCGTCGGTGTCTGGGTGCAAATCA
```

(Underlined=GeneRacer Oligo sequence; Bold/Underlined=start codon; coding sequence in bold) (Sequence of 5' RACE product CW61A10-Full_Length cloned into pCR4-TOPO) (derived from MEST61-A10, GB_ACC# BM073122):

The predicted protein or polypeptide encoded by the full-length cDNA clone of SEQ ID NO:27 has an amino acid sequence of SEQ ID NO:28, as follows:

```
MTAHQTCCDDAVAAGTAPAARRRRLKLTRPSASLLMARKLRKKAAGSKRP

RAAASRKRAMAIRRKMEALRLLVPLCGRDNGSVTGGAVERLDELLMHAAG

YILRLQMQVRVMQLMVHALNDRPED
```

A putative promoter (upstream of the transcription site of the gene) for the gene of the full-length cDNA clone of SEQ ID NO:27 has a nucleotide sequence of SEQ ID NO:29, as follows:

```
taaatctgacctccaaaatgtctctaatgaaagtgtctgcgagaaacagt attgctcgaccgaggaagaaaggtatttataacacacccatcacaaatgg ttggcttaattaaccgcaagtgcagaatagatttgcactgttggttcact taataaaactgcaagtgaaaatatacttttttctactatcggttttgttaa gtgaacctaccgattttgcactggtgattatttaagccaacctcatgtga taatatgaatgatttgcacgtggttttattaagcgaactaacaatgtaaa tgtgtttccaatggtggttttttaagtcgggaccgtcattttactttaact ggcgcgcaccgtgctgttttatacttgactgatgaaccttcgtggtgagt ggaagcggtgtggagcgagggctagctcatgcggccagccggcgacattt ctcttgttccgatccccggccggccaaccactcaattaagtaggtgatc gattggcatgcatgcatggatgcatatcagcaaatgcatatcatatgcct cgctagctggctagtatatatagtggatgtggatcggatcatgtgacggc cgggcggtggctgcattgcattggccctgcatatatgcacggtgacacaa caacggggcccaaataaggacacgtcgaaggtgcgcgcccccagtggcgt ccgacagcgcgttttgacgaggaaaagagggtgcgggcacgcgcgcacgc atatgctcgcggcatgcagcctcagtggccgatgacgagtggcgtgtggt gtggccggcggccggccgggtgcctgcgtggtgcatgttgcttgcc atgcctgcgtgaaatgagccgtcagcgagcgagctgagggcgggcatgtg gctgcatgtggccactagtttggagaacatgcggcatatgccccggacct tcctgggcgctcaagcaaacaccgctctcgtgctcgctcttgggaaat cgcagatgcatgctacccaacgtgacctggatctcttttacgtacgcaca ccctagcgtgctgctctcctgtgtccccgcctcctgctagctgttcacaa tatccacgcgatttaacaaacagatatgtgtgcatgctactgcttgtttt
```

```
cctattcaatatagtaatctgctttatttagagtaccgtacctgtgccgt cagtgcccccaacccaacgtaactacgcacgcacatggcatctaatcta tataagcatcagaccttgctcccttaatctcgcgctgctattttcttctt acattgtccactgcgctagctagctcgcatctacctggaaagctgaaagc tagccagagcgctagctagcttcgttcctcgtcgccgcgcgccggccaga tgactgctcaccagacttgctgcgatgatgccgttgccgccggcactgca ccggctgccaggaggaggcgcctcaaattgacgaggccgtcggcctcgct cttgatggcgaggaagctaaggaagaaggctgccggcagcaaacgcccaa gggcggcagcgtcgaggaagcgcgcgatggcgatcaggaggaagatggaa gcgctgaggctgctcgtgccactctgcggccgagacaacggctcggtgac cggtggggcggtcgaacgactggacgagctcctcatgcacgccgcccgggt acatcctgcgcctccagatgcaggtcagagtgatgcagcttatggtccat gcactaaatgaccggcccgaggattaatcttcttcccaagaccatgtgat cttccttctttaatttcttcttcatcttcttcgcgtgcctgtgttgcacg aggcagctgtgcgtcggtgtctgggtgcaaatcattggctgagtgtgtta ttggtgatattatttgttcgtatatacagaatatatactcatgcatgcat actgtatgagatgatagagtaaatctagacatatatagttcaaggaaacc tacagccaacagttgtatgcatgtgagggggggttccttgtctgtatgtac gcaattgtctattgtgtgacggttgaaattgaaatttcgtcaatcatcat ttcttcgtctagataacgtgtgtacaaacggcgagtgtttaaatgaacta gagctaataattagtggctaaaattagctggagacatccaaacaccctaa ctaataatttaactattagttattttttagtaaattagtcaatacttagct agctatttgttagctagctaattctactagcattttttagctaactagct attagctctagtacattcaaacacccttttagggactaattttttagtctc tccatttttatttcattttagtcactaaattaccaaatacgaaaattaaag ctctattttagtttccggtatttgacaatttag
```

(>MAGI4_145622 MAGI4.contigs_w_singleton.fas 2433 bp)

A suitable nucleic acid molecule of the present invention is a gene that is up-regulated by nitrogen and contained in a full-length cDNA clone having the nucleotide sequence of SEQ ID NO:30, as follows:

```
GGACACTGACATGGACTGAAGGAGTAGAAAATCCATCCATTCCCCTCGCC

AAGCCGCCACGGCCTGACTTTCCCTCCCGCACACCCGCGACCATACAGGC

AAGTCAGGCATACACCAACAACGCTCGTCGTGCACCTCGCGCCTCAGGTC

ACCCCACCAAATTCCTCTTGATACGCCGAATTTCTTTTGCTAATTCTGCT

ACCTCCTGTCGCTAAGCCACCATATTCAGTCTAACCCCTGCTCTGAGCTC

ACCTGATTGGCGGCTCCGTTCGGCCTCTGGGCCTGGGTGTACCGACTACC

GAGGGCTCTTTCGAAATGTCAATTGGGTCGAGTTTGGTGGGCTACGTGAA

GCATGGATTTCCCGGCTGGAAGCGGGAGGCGGCAGCAGCATCCGGGGCCG

GAGCACCTGTCGCCGATGACGCCGCTCCCGCTGGCGCGGTAGGGGTCGGT
```

```
CTACTCGCTCACGTTCGACGAGTTCCAGAGCTCGCTCGGTGGGGCCACCA

AGGACTTCGGATCCATGAACATGGACGAGCTCCTCCGCAACATCTGGTCG

GCGGAGGAGACACACAGCGTCACAGCTGCGGACCATGCCGCGCGGGCGCC

GTACGTCCAGTGCCAGGGCTCGCTCACCCTCCCCTGCACGCTCAGCCAGA

AGACCGTCGACGAGGTCTAGCGTGACCTCGTGTGCAACGGTGGAGGACCC

TCCGACGAGGCTGTGGCGCCGCCCCACCGGCCCAACGGCAGCCGACGCTC

GGGGAGATCATGCTGGAGGAGTTCCTCGTCCGCGCCGGCGTGGTGAGGGA

GGACATGATGGCGGCGGCGCCCGTACCACCAGCGCCGGGTTGCCCACCAC

CTCATCTGCAACCGCCAATGCTGTTTCCACATGGCAATGTGTTTGCTCCC

TTAGTGCCTCCGCTCCAATTCGGGAATGGGTTTGTGTCGGGGGCTCTCAG

TCAGCAGCAGGGAGGTGTTCTTGAGGCCCCGGCGGTATCGCCGCGGCCGG

TGACGGCAAGCGGGTTCGGGAAGATGGAAGGAGACGACTTGTCGCATCTG

TCGCCATCACCGGTGTCGTACGTTTTTTTGTGCTGGTTTGAGGGGAAGGA

AGCCACCAGCTGTGGACAAGGTGGTTGAGAGGAGGCAACGCC
```

(Underlined=GeneRacer Oligo sequence; Bold/Underlined=start codon; coding sequence in bold) (Sequence of 5' RACE product CW76H12-Full_Length cloned into pCR4-TOPO) (derived from MEST76-H12, GB_ACC# BM073865)

A predicted protein or polypeptide encoded by the full-length cDNA clone of SEQ ID NO:30 has an amino acid sequence of SEQ ID NO:31, as follows:

```
MDEFPGWKREAAAASGAGAPVADDAAPAGAVGVGLLAHVRRVPELARWGH

QGLRIHEHGRAPPQHLVGGGDTQRHSCGPCRAGAVRPVPGLAHPPLHAQP

EDRRRGLA
```

Another predicted protein or polypeptide encoded by the full-length cDNA clone of SEQ ID NO:30 has an amino acid sequence of SEQ ID NO:32, as follows:

```
MLEEFLVRAGVVREDMMAAAPVPPAPGCPPPHLQPPMLFPHGNVFAPLVP

PLQFGNGFVSGALSQQQGGVLEAPAVSPRPVTASGFGKMEGDDLSHLSPS

PVSYVFLCWFEGKEATSCGQGG
```

A putative promoter (upstream of the transcription site of the gene) for the gene of the full-length cDNA clone of SEQ ID NO:30 has a nucleotide sequence of SEQ ID NO:33, as follows:

```
tagaatagccagcatcgacaaattacttacaaatagaaacattacctgtt tcctcccacgcgacctcgcggccaactcccggttcttgatcatccggcgt tgcctcctctcaaccaccttctccacagctggtggcttccttcccctcaa accagcacaaaaaaacgtacgacaccggtgatggcgacagatgcgacaag tcgtctccttccatcttcccgaacccgcttgccgtcaccggccgcggcga taccgccggggcctcaagaacacctccctgctgctgactgagagccccg acacaaacccattcccgaattggagcggaggcactaagggagcaaacaca ttgccatgtggaaacagcattggcggttgcagatgaggtggtgggcaacc cggcgctggtggtacgggcgccgccgccatcatgtcctccctcaccacgc cggcgcggacgaggaactcctccagcatgatctccccgagcgtcggctgc cgttgggccggtggggcggcgccacagcctcgtcggagggtcctccaccg ttgcacacgaggtcacgctagacctcgtcgacggtcttctggctgagcgt gcaggggagggtgagcgagccctggcactggacgtacggcgcccgcgcgg catggtccgcagctgtgacgctgtgtgtctcctccgccgaccagatgttg cggaggagctcgtccatgttcatggatccgaagtccttggtggcccacc gagcgagctctggaactcgtcgaacgtgagcgagtagaccgacccctacc gcgccagcgggagcggcgtcatcggcgacaggtgctccggccccggatgc tgctgccgcctcccgcttccagccgggaaattcatccatgcttcacgtag cccaccaaactcgacccaattgacatttcgaaagagccctcggtagtcgg tacacccaggcccagaggccgaacggagccgccaatcaggtgagctcaga gcaggggttagactgaatatggtggcttagcgacaggaggtagcagaatt agcaaaagaaattcggcgtatcaagaggaatttggtggggtgacctgagg cgcgaggtgcacgacgagcgttgttggtgtatgcctgacttgcctgtatg gtcgcgggtgtgcgggagggaaagtcaggccgtggcggcttggcgagggg aatggatggatatgtgtcgccaccaaggagtcgtgtgggggagtttaaaa cgtcgccaggctcgaggtcgcacatggtgttgggtttgggtgcgtgctgg gtcataaaagctgaaagggaattaggcttacacctatttcctaaatgatt ttggtggttgaattgtccaacacaaa
```

(>MAGI4_7232 MAGI4.contigs_w_singleton.fas 1376 bp)

A suitable nucleic acid molecule of the present invention is a gene that is up-regulated by nitrogen and contained in a full-length cDNA clone having the nucleotide sequence of SEQ ID NO:34, as follows:

```
ATTCCCGTCTTACCTAGCGCTAGGGTTAGTACGCGTCCACGGCGACGACC

TCTGCGCGGAGTGTGCTCCGATTGGCTGGCCTCCTCGATCCTCCTTCCCG

CGAACGCACGCGCGCGCGAGGGAGAGGTTGAGACTTGAGAGATAGACGAA

AGACGAAACAAGGGAAGGAGACGCCGTGCTCGCCTATTGGCCGCCGCCTC

CGCTCCTTCGCGCCCAATGGCTTCTGCAGCATATCAATATCATGCAGCAT

AGCAGTACTCAGACCCTTACTACGCAGGCGTTGTTGCTCCCTATGGAAGT

CAAGATGTGTGTCCGAGGAGCCTGTCTATGTGAACGCCAAGCAGTACCGC

GGCATTCTAAGACGGCGGCAGTCACGTGCCAAGGCCGAGCTTGAGAGAAA

GCGCTGGTCAAGCAAGAAAGCCGTATCTTCACGAGTCCCCGTCATCAGCA

CGCGATGACGAGGAGGGCGAGAGGGAACGGTGGACGCTTCCTAAACACGA

AGAAGAGTGACCGTGTCCCTCCTGATGACTTGATACAGCTACGACGACAC

AACGAGGCTTGAAGAGGTAGCGGTCTGGCTGGCATCCTAGAGCAGCGGTT

TCTGTCCACAGGCACGTGCATCTGAGACCGGATCCGTAGCTCCACTCCAC

AGCATATGCGCAGCCCATCCATCTCGTGCACACTTG
```

(Underlined=start and stop codons; coding sequence in bold) (Sequence of 5' RACE product AM77A01-5T3 Full_Length cloned into pCR4-TOPO)

The predicted protein or polypeptide encoded by the full-length cDNA clone of SEQ ID NO:34 has an amino acid sequence of SEQ ID NO:35, as follows:

MQHSSTQTLTTQALLLPMEVKMCVRGACLCERQAVPRHSKTAAVTCQGRA (The above sequences are presented after trimming GeneRacer Oligo sequence. Cloned in pCR4-TOPO vector at the "TOPO Cloning site".)

A suitable nucleic acid molecule of the present invention is a gene that is up-regulated by nitrogen and contained in a full-length cDNA clone having the nucleotide sequence of SEQ ID NO:36, as follows:

CGACTGGAGCACGAGGACACTGACATGGACTGAAGGAGAGAAAAAAACC

CAAATCAAATTTCGCCTTCGTCGTCGTCTTATCGTCTCAGATTTGACTCC

ATGTCGGCGGCGCTCGCGGTGACGGACGAGGTGGCCCTGCCGATCCGGGC

GGTGGGGGATCTAGCGGCCGCCGCCGAGGTCTCGCGGGAGGAGGTCGCCG

TCATCACCCAGTGCGCGGCGCTCGGTGGGAAGTTGCCTTTTGAAGATGCA

TCAGTTGGTGCGGTTCTTGCAGTCATTAAAAACGTGGAAAGCTTGAGGGA

GCAATTGGTTGCTGAAATCAGGCGGGTGCTGAAAGCTGGTGGAAGAGTAT

TGGTGCAGAGCCCTGCACCCTCATCCAGTCAGAAGCCGAACACTGATATT

GAGCGCAAGTTACTGATGGGTGGATTTGCTGAAGTGCAATCTTCTGCTGC

AAGCTCGCAGGATAGCGTGCAATCTGTTACAGTTAAGGCAAAGAAGGCTA

GCTGGAGCATGGGCTCTTCTTTTCCCCTTAAGAAAACAACAAAAGCCCTT

CCCAAGATTCAAATTGACGACGACTCTGATCTGATTGATGAAGACAGTCT

CTTGACTGAGGAGGACCTGAAGAAACCACAACTTCCAGTTGTTGGGGACT

GTGAGGTGGGGGCAGCAAAGAAAGCATGCAAGAACTGTACTTGTGGCAGG

GCTGAGGCCGAGGAGAAGGTTGGGAAGCTGGAGCTCACTGCGGAGCAGAT

CAATAACCCTCAGTCAGCTTGTGGCAGTTGTGGGTTGGGTGATGCCTTCC

GCTGTGGAACCTGTCCCTACAGAGGTCTTCCACCATTCAAGCCTGGCGAG

AAGGTTTCCTTGTCTGGCAACTTCCTTGCTGCTGACATATGATGGCATCG

CCAACATCGGCAAAACAAGGA (Underlined=GeneRacer Oligo sequence; Bold/Underlined=start codon; coding sequence in bold) (Sequence of 5' RACE product CW88H03-Full_Length cloned into pCR4-TOPO) (Derived from MEST88-H03, GB_ACC# BM079064)

The predicted protein or polypeptide encoded by the full-length cDNA clone of SEQ ID NO:36 has an amino acid sequence of SEQ ID NO:37, as follows:

MSAALAVTDEVALPIRAVGDLAAAAEVSREEVAVITQCAALGGKLPFEDA

SVGAVLAVIKNVESLREQLVAEIRRVLKAGGRVLVQSPAPSSSQKPNTDI

ERKLLMGGFAEVQSSAASSQDSVQSVTVKAKKASWSMGSSFPLKKTTKAL

PKIQIDDDSDLIDEDSLLTEEDLKKPQLPVVGDCEVGAAKKACKNCTCGR

AEAEEKVGKLELTAEQINNPQSACGSCGLGDAFRCGTCPYRGLPPFKPGE

KVSLSGNFLAADI]

A putative promoter (upstream of the transcription site of the gene) for the gene of the full-length cDNA clone of SEQ ID NO:36 has a nucleotide sequence of SEQ ID NO:38, as follows:

gctgtaccagttgaggtactccttgacgtcctcgtacatggtgggcgcca gcgggtgccagatgccggagtcgaggtagagcacggggtcgtcgtacttg atgccggcgccccctaagcaccggcaagtaggatccggcgatcatcttgag gaagttctggaggttgtccgccgagccgccgagccagaactggaggctga ggatgtacagccaggcgtcctgcgccttgtcggagggcaggtacttgagc accttgggcagcgtgcgcacgagcttgagcatgctgtcggcgaagttgct ggagttggacttgctgcgcttgaagagctggaagaaggggctcttggact gccccagctgcgacatgctgaaggagccgagcttgttgaggcgcatgacc tcgggcatggaggggaagacaaggacggcgtccatgcggtcgcgctcctt ctcggccgcggccttgaccttgagcgccagctcctcgacgaagatgaggg agccgatgaagacgttgacgtcggcgaggtcggcgcggaaggtagcccac gacctcgaacgacgcggcgggcgcgggtcagcgttgagctgctgcacgg cggccgtgacggacgactggtactgcgcctccagcacgacgtagacgacc ttgacccgaggcaggccccgcgggtcggccggcaccacgcgccgcacctc gggcttggtctgcgtgaacaagccgttgccgccggcgaccgcgcaccgga tggcgccggcgcgccgcggctgctggcgacggctgctcaggaggaacgag tgcagcggcacgggcgccgccaggagctgcttctgcgccgcggcggcgaa tggggtggacactagcgacgacgacatggcgcctgctcacaggacggagc cggcgggcggagaaacgcgcgcctggacactgacgcgacgctcgagcgca gtaagtaaaaaaaaatctacactagactactagagtaaggcgcctgttct tggctcgtggctggacaattgttcttggcggccgccgtccctcggaaaca gagcagggaaaggagaagaagcgagcaggggagcgcgggaggcgggaaaa tgtataggttgtccgtgtccacgtccttcgtctcaattaagaagaggcat ccaggctcacaaaatcaatctgaaaacacatgcactgatgcacacttgtg tttgtgtagaggcgcttatatatcatccaaaagacaagtcactcacacgc aaattcgcattggctaacagaagctatttggaatgcagttcagtcgacta acaacgtaggtaccccccgtctccttgttttgccgatgttggcgatgccat catatgtcagcagcaaggaagttgccagacaaggaaacctgccaatcgga gaagcagcagcagtgaacgttcaagatccagagtacaatcgacagacata ttttgatctcctcgagaattctatcaggggaggagacgagtagaactgtt ttaccttctcgccaggcttgaatggtggaagacctctgtagggacaggtt ccacagcggaaggcatcacccaacccacactgcaaagaaaaatcaaggat catttacagatatcaccagacgtgataggtaacctagtccgagtgaacgt atgaaatttcacgaggggggcacaagtgccacctgtaagcaatacttacac tgccacaagctgactgaggggttattgatctgctccgcagtgagctccagc ttcccaaccttctcctcggcctcagccctgccacaagtacagttcttgca tgctttcttcttgctgccccccacctcacagtccccaactggtgaaaacatca gtgaaaacatcacttaactgtttaggatccaaacctaaactggctattgc -continued

```
ttacggagttgaactaagttgacgggttttgttgctctaccaactggaag
ttgtggtttcttcaggtcctcctcagtcaagagactgtcttcatcaatca
gatcagagtcgtcgtcaatttgaatcttgggaagggcttttgttgttttc
ttaaggggaaaagaagagcccatgctccagctagccttctttgccttaac
ctacaagtggttcaaattagcacaaaaactaaagcctgcacagcaaaact
aacatactataacacatgatcttagaccactcactgtaacagattgcacg
ctatcctgcgagcttgcagcagaagattgcacttcagcaaatccacccat
cagtaacttgcgctcaatatcagtgttcggctaacggagacaatcataaa
aaaattaagaactttaaatcgacattgcaagagaaacgagacaacaaaga
cagattctgataagttaataccttctgactggatgagggtgcagggctct
gcaccaatactcttccaccagctttcagcacccgcctgatttcagcaacc
aattgctccctcaagctttccacgttttaatgactgcaagaaccgcacc
aactgatgcatcttcaaaaggcaacttcccacctgatgcatggcagaaca
atagtttggtcacggttttgtgataacacacacacacacacacacacaca
cacacacacacacacacacacgggcatagcactagcaaagcataa
cacaaattaaaaatcgaacattattgtttaatagaggctcccaaaatcag
gaatgctagcacttggcttattcataaacacacacatccataatcaggaa
gcatacattactgaaccattaaatttaataataaaaattcagatgttgaa
tccatggctgaaattttctgttccttttgaaagtataatcctaactttca
tctccggctgacctggtaatatcttctagctccttttaccttatattttt
ttcagttgcttgagaaatagcggtaggaaaattgacacatgtcattcgta
aatccatgggacttagagcaactccaagagcttcctaagaaattgttccc
caaaacatcatatagggggctgctgaaaaaaatccactaagagcaactcc
aaatgagtgctagaaaattccccaaaaaatgattattggggatatgtta
aaaaattttaggggtgaattatcatgtatactccaacgattccgttaaac
aaatgcgactcaatctcagccacagtctgagtcttacagacacacaaa
acctaacatgccggtggcagccacattatcacacaccggaacaaataact
ttgaggcaaaaacacattatgcaagcagagaaacaccagaacagactccc
agctgttgaagtgcaaatgtgttttctatatttgagttacttgctggtaa
atcccgatcgggaatgtaataatcggggagttgcattagcacttttgcag
caagctaagccaactggttgggaatgtcaagcattcttgagcaggagtac
tagtcaagttaacaggcttcagatcccatccaatcattgtcacatttgaa
tataacttgagcgggtagaaaaaatatcataacaaaggcatcatggactg
aatcctaaacatcataacgaaggcatcatggactgaatagcgatcatcat
aacaacggcaggaaacagactcccaactgaatcatggttaacatggactg
aattgtggtggcactgcatgcagtgcgagatgcatcatatccaggtcaat
tcaggttagcaaatgcaaggccacaggagttgccgccagggaggaggctc
taggcgaggtcacgggagttgcggtggaagttgctgcggattggggaaga
cctttgctcgccaatatttgagggagagtggagctcggatgcgggacgct
gataatttgggggaaggaaaggggaactattgggtggagaattttttgtt
```

-continued

```
tttcaccccaaaacatgttttgggtggttttagcgttcttctggagat
gctcttaagcaactagcacatgagacatggcatagatatcaagaactgca
aggagaggttcaagttcaaatctgaagaagtctgcaagggcatgtccaca
gattcagcggttttggagttgggaaataacttcagctttcttttctttt
gttgttgagacgttcttttcttttctttttttttgttgttgttgaggc
gtcagctcgacgttttcattctacacattagaaagtggcagtagcgcaag
agataccacagggccaaaactactagtggtactgaaagttttcattcgaa
gaatcagtaagtggcactatcacaggaagaaacattgcaaggccaaactt
ggcgtccactgactgcgcttcaatattacttgagcaacttgctagcctcc
cgatcccggaaggatggtttgataaactaattctctaattgaagtgggaa
cccttaagaaccaaacgtccactactccaaatttgattgcaaaagaaaaa
agaatctagcccattccgcggaatcacgccagaaggctcgctaattgaag
catgcaagcaaggcagcaaagagaacagcacgcatcgacgggttcctgca
tccacaagcacgaacttggcaacttgccatggtcgcctcgagggaaagaa
atagaagaaaaatggaaagagggcaagacggggcgaaaccagctaagc
tcaccgagcgccgcgcactgggtgatgacggcgacctcctcccgcgagac
ctcggcggcggccgctagatcccccaccgcccggatcggcagggccacct
cgtccgtcaccgcgagcgccgccgacatggagtcaaatctgcacacgagc
acacgcgagaaccagaagagactcggtgaaaggagtatccccgaagaga
aaaggaattagggttaatcgagggagggttttatctgcacgccccggat
tcatcacgcgactgctacctgagacgataagacgacgacgaaggcgaaat
ttgatttgggttttgcctggcctcctctcctctcgaagcttcacaacacg
ccgagttatttgatattgtaacaatctcgtcgcgcggcttcaccagttat
tactccgtagttatacttcgctagtttagtatt
```

(>MAGI4_101388 MAGI4.contigs_w_singleton.fas 5083 bp)

A suitable nucleic acid molecule that is modulated (e.g., up-regulated) by nitrogen is the non-symbiotic hemoglobin gene (MEST129-009.T3Seq) from corn having the nucleotide sequence of SEQ ID NO:39, as follows:

```
catccatccatccatccatttccaatcccaatcccaatcccaccagtgtc
cagtgctcggggaaccgacacagctcctcagcagagtagccagcacgaca
agcccgatcagcagacagcaggcatggcactcgcggaggccgacgacggc
gcggtggtcttcggcgaggagcaggaggcgctggtgctcaagtcgtgggc
cgtcatgaagaaggacgccgccaacctgggcctccgcttctttctcaagg
tcttcgagatcgcgccgtcggcgaagcagatgttctcgttcctgcgcgac
tccgacgtgccgctggagaagaacccaagctcaagacgcacgccatgtc
cgtcttcgtcatgacctgcgaggcggcggcgcagcttcgcaaggccggga
aggtcaccgtgagggagaccacgctcaagaggctgggcgccacgcacttg
aggtacggcgtcgcagatggacacttcgaggtgacggggttcgcgctgct
tgagacgatcaaggaggcgctccccgctgacatgtggagcctcgagatga
agaaagcctgggccgaggcctacagccagctggtggcggccatcaagcgg
```

-continued
```
gagatgaagcccgatgcctagtagtggcgattgcgaccagtgtttaaccc atgacgcagcgccgtcacagatgtcccgtgtggtcttgcgctttagcaat ttctctctggagggagcgtgtattgttatcttgtgatcgagagcctgtgt gctgcctttgcttcttgtgattatatagctactgaataaagatgtagcgt tcttcaaaaaaaaaaaaa
```

The predicted protein or polypeptide encoded by the full-length cDNA clone of SEQ ID NO:39 has an amino acid sequence of SEQ ID NO:40, as follows:

```
MALAEADDGAVVFGEEQEALVLKSWAVMKKDAANLGLRFFLKVFEIAPSA

KQMFSFLRDSDVPLEKNPKLKTHAMSVFVMTCEAAAQLRKAGKVTVRETT

LKRLGATHLRYGVADGHFEVTGFALLETIKEALPADMWSLEMKKAWAEAY

SQLVAAIKREMKPDA
```

A suitable nucleic acid molecule of the present invention is a gene that is up-regulated by nitrogen and contained in a full-length cDNA clone having the nucleotide sequence of SEQ ID NO:42, as follows:

```
TCGACTGGAGCACGAGGACACTGACATGGACTGAAGGAGTAGAAAATCAC

CTAGCTAGAAAGGAGAGCACCGAGCGCTGCACCACTACTGCTGATATGAG

CACCTGAACCTTCTGGGCAACCACATCCGGTCCCTGCCCCTGATCATCCG

CAGCAGCCATGGCGCAGCAGCAGGAGAAGAAGCAGCAGCAGAGGGGGAAG

CTGCAGAGGGTGCTAAGGGAGCAGAAGGCTCGGCTCTACATCATCCGCCG

ATGCGTCGTCATGCTCCTCTGCTGGAGTGACTGATCCATCTCAAGCATGC

ATGATAAACCTGTGCTCTTTTTTTTTCCTTCTGTTTTTTCCCCTCTTTTT

CCCATCCTTTTCACCTTGCCACTTTGGTGGGCGA
```

(Underlined=GeneRacer Oligo sequence; Bold/Underlined=start and stop codons; coding sequence in bold) (Sequence of 5' RACE product MEST213-C11-Full_Length cloned into pCR4-TOPO)

The predicted protein or polypeptide encoded by the full-length cDNA clone of SEQ ID NO:42 has an amino acid sequence of SEQ ID NO:43, as follows:

```
        MAQQQEKKQQQRGKLQRVLREQKARLYIIRRCVVMLLCWSD
```

(The above sequence is presented after trimming Cloned in pCR4-TOPO vector at the "TOPO Cloning site".)

A suitable nucleic acid molecule of the present invention is a gene that is up-regulated by nitrogen and contained in a full-length cDNA clone having the nucleotide sequence of SEQ ID NO:44, as follows:

```
CGACTGGAGCACGAGGACACTGACATGGACTGAAGGAGTAGAAAAACTAA

CACTTCACGTGCCCCCATCCTTTTCCGCCTCAAGTCAAGTGTTCACGGTC

CATCCTCTCGAGAGTCTAGGCCCTTCTCCCGAAGCCGCAGACGCAGAAAA

CGGCTCTGCATATGGAGGCGAAGAAGAAGCCGTCGGCCCCCGCCGCCGTC

GGAGCCGCGCCGCCGCCGCCGGGTAACGGGTACTTCAGCACCGTCTTCTC

CGCGCCGACTGCGGGAAGCGCAAGTGACGCAAAGCATGCGGACTTGTACA

CGATGCTGAACAAGCAGAGCTCCAGAGGGCAGAATGGCAGAGATGGCAAA

TCCCACAGCCGCCCTACTTACAAGGATGGCAAACATGCTCATCCAAATGA

GCCATCAGAATCTCCTTACTTTGGCTCATCCGTGCATTACGGTGGTCGGG

AGTTCTACAGCAGCGTTTTACGGAAGCAACCAGCCAATGAACCCCATACG

GATTACAAGGGGGACAACCCGGATGGCTCTGCTACCAGAGGTGATTGGTG

GCAAGGTTCACTTTATTACTGAATAATCTGCTGGGACCTCTCCCTTTTGT

GAACAAGGAATAAAAGGGGTAGAGCTGAGAATGGTTTGTTGTAGTGTTGG

AAGTGTTGACGCGAGCCGTCAAGCATCGATCAATAGTAATAGTTGTAATA

GTTGAAAGCTGCGTCGTGACTACAAGCATCCTGTTGGTGGAGGCAGTATT

TTAGATCCATCATCACGCCTGGACAGATGTGGGTGTCC
```

(Underlined=GeneRacer Oligo sequence; Bold/Underlined=start codon; coding sequence in bold) (Sequence of 5' RACE product CW264H08-Full_Length cloned into pCR4-TOPO) (derived from MEST264-H08, GB_ACC# BM350368)

The predicted protein or polypeptide encoded by the full-length cDNA clone of SEQ ID NO:44 has an amino acid sequence of SEQ ID NO:45, as follows:

```
MEAKKKPSAPAAVGAAPPPPGNGYFSTVFSAPTAGSASDAKHADLYTMLN

KQSSRGQNGRDGKSHSRPTYKDGKHAHPNEPSESPYFGSSVHYGGREFYS

SVLRKQPANEPHTDYKGDNPDGSATRGDWWQGSLYY
```

A putative promoter (upstream of the transcription site of the gene) for the gene of the full-length cDNA clone of SEQ ID NO:44 has a nucleotide sequence of SEQ ID NO:46, as follows:

```
aaagcttacacttcataagagattcatagttttatcttacagccatcgtt gtcaacctcaactaccatgcaatccgtttgggattcaactagcaagtaag gggatgtttgtttgggtttataatctgtctggattatataatctaacaac ttttgaactaacacttagttcaagaattgttggattatataatctaggca gattataatcccaaacaaacacttcctaagtcttgtacaggctatagaga ttattttccagaatggaggagggataatgacaagacctaaaagaaagtt atgtttatggaaaacaaaaaaatggagccaggataatgacacaaaagaaa ggtatgttttctggaataaaaaaaattaaatatatattttgaacttccta agactggaacatgatacctaagctggacagatgatcaaggacagttttac ccctggagacagaaaaacttataagacttagcttctacatcatatcctg ttttgtatgtctcataattaggttccttgtattaagacgaccaacctatc atttgttatacaaaattcgaacgactgctgaagtctcgaagtatatagtc taggctgattaaaatgtaagtatgggttaaagtgctgctggtaacaaact aaatacaactgtatgatgttgttgacaacaagacataactcaaaatggga gcaccaacaaagtgactggcaccggtgatgcaagcataacctaaacacaa ctaatggaaaacgcgaattggaaactatgaaagtgtcccatatatggtat accttgttcacaaaagggagaggtcccagcagattattcagtaataaagt
```

-continued

```
gaacctgaaagtgaagtctagcaagtcagtgtatgagcgtccatgtatat actgaagataatacacaaattgatgcaatgatacct tgccaccaatcacc tctggtagcagagccatccgggttgtcccccttgtactggatttaaaatt caaaataaacattagacttaagcgctccaaatgatctgtactacgtatat ataaaaaggttctacgtacatccgtatggggttcattggctggttgcttc cgtaaaacgctgctgtagaactcccgaccaccgtaatgcacggatgagcc aaagtaaggagattctgatggctcatttggatgagcatgtttgccatcct tgtaagtagggcggctgtgggatttgccatctgagcacgaatttaaactt ccatagttaaaatcagtgctccagattaattctaagctaagatggtgaga aaaggttttaagtatcgttgtgcttatgaacgcgacctaaatcgaagaga aacgtcaaattgacaagagtacccagaactacctctgccattctgccctc tggagctctgcttgttcagcatcgtgtacaagtccgcatgctttgcgtca cttgcgcttccct tgaatgcaaaacaaagtcaaatgtcaacgtcatatc caaatagattttgcataatcctataggtcctctattatcaaaatcacccc tcatcagaattaaattgggaaaccgttgaagtccctccacaaatcgcaac atagtaacggactctttcatcaaatcgcaccagctcactaatcatgcaaa aaaattactaagacccaggaatctgagagcaaaatatcagaacgatggc gtgaagagacggcccgtaccgcagtcggcgcggagaagacggtgctgaag tacccgttaccggcggcggcggcgcggctccgacggcggcggggccga cggcttcttcttcgcctccatatgcagagccgttttctgcgtctgcggct tcgggagaagggcctagactctcgagaggatggaccgtgaacacttgact tgaggcggaaaggatgggggcacgtgaagtgttagttgtaggcggcggc ggccggcggggaaggaagcagttggttgttcgcctcgtggcgtcctgctt cggccaacatctgtgccggcatttaaaggcctcgacggagcgactcggtt tcgctatttcggagatcttaagggcctgaatggagaaaattgtgtttagc tttcatccacatccatccaacctgcagtgagacttgcagagtgcagactc ccgtattacagggacggtcctgaataagttagtagttttatttcagagat tcaacgatgttagtatacgaattatttagacacgtttggaatcatccagt ttttttagcaatctgatttataaaaagtcaagtgcttccaaacatatcaga ttatgcttcggttcttaaaaatcggactgcctcttccataactaaaatta gtttttaacttggtagaaattagtgattgtaaccgctcttaggtctatgc atgtgattccctcgatgtctttatcccatttgaatatttaattattattt aaaaattttagattaaaaatattaattcaatctatatttaaaattggcaa caaagaaaaacaaagagaataatagaatcaattactttt ggaatagagta aggattgaatttgtctttgtgtataacaaagctagaagttggtttccaag aactagcctctaacacgcacacctattttt
```

(>MAGI4_139395 MAGI4.contigs_w_singleton.fas 2631 bp)

The present invention relates to a nucleic acid construct having a nucleic acid molecule that is modulated by nitrogen in corn. The construct also includes a 5' DNA promoter sequence and a 3' terminator sequence. The nucleic acid molecule, the DNA promoter sequence, and the terminator sequence are operatively coupled to permit transcription of the nucleic acid molecule.

The nucleic acid molecules of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pG-Cha, p35S-Cha, pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor, N.Y.:Cold Spring Harbor Press (1989), and Ausubel et al., *Current Protocols in Molecular Biology*, New York, N.Y:John Wiley & Sons (1989), which are hereby incorporated by reference in their entirety.

In preparing a nucleic acid vector for expression, the various nucleic acid molecule sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase ("NOS") gene promoter from *Agrobacterium tumefaciens* (U.S. Pat. No. 5,034,322 to Rogers et al., which is hereby incorporated by reference in its entirety), the cauliflower mosaic virus ("CaMV") 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a nutrient (e.g., nitrogen, including nitrogen in the form of nitrate), a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (see Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death, *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the *Chrysanthemum* UEP1 Promoter and Comparative Expression in Florets and Leaves of *Dendranthema grandiflora*," *Transgenic Res.* 11:437-445(2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimaeric Granule-Bound Starch Synthase-GUS gene in transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

A suitable promoter can also be one that is gene-specific, in that it regulates transcription of a nucleic acid molecule of the present invention. A suitable gene-specific promoter gene-specific promoter (derived from MAGI93503) has a nucleotide sequence of SEQ ID NO:41 as follows:

```
CGTTGTCGGAACGTCCCGTCGATGTTCGGAAACGAGCACGACCCGTCGAC

TCCTGCTTCTTGGCGGAGAAGAAAGGGGACGACGAGCGAGCGTTTTGACT

TTGATTTCCTCGCTAAAACCGGCCGCTGTTTTTGCTTTCCGCGCGAGCCG

CCCACGTTATTGACTGACGCTGGTGCGAGAGCGCTGCTGCCTCTGCGGTT

GCCGTCTGCGCTCCAGTGGTAGCCGAGAATATTGTTAGGTCCGTAGGATC
```

```
-continued
AGATTTGCTACGTACTAAAAAAATTCCTTAAACTTTAATTGTGTATTTTT

TTTAAAAAAAATTATAGCATTTATCAGCAACAAAACTCTAAAAACATGTT

TAGTTCGCTGCTTAATTTATCACATATTGTCTAAATTTTATATATAAATT

ATTTAATTCGAACGACTAACCAGAACCCAGACCTACAATAAATTTGCCCC

CGCTGCTGCGCTCCCCAGCTCCCCAAGTCCCTAACCCGCCCTCGCTTTGT

CGCCGCGGCACACGGTTTTGGCCGTGGACAGGACAGTTGCACCCTAGCCC

CATTGGCCGATTCCGAGCTAGGAAGGAGTATATGCGTATCGGTAGTAACC

GAGGAGCAACGCAACATGTCCACAGCCCGCGCGCTGGTAACGGGTCCATG

CGTCTTGGCTCATCAGGTGCCCCAAGGGACGCCCTCGCCCGGTCTGACCC

ACCTATATAAACTTAAAACTTGTGCCCCAACATCATCAGTTCGTATCACA

CCCAACCTCCCACTGTAAAAAAGAGCAGCGGAACGTGCGTGCATCCATCC

ATCCATCCATTTCCAATCCCAATCCCAATCCCACCAGTGTCCAGTGCTCG

GGGAACCGACACAGCTCCTCAGCAGAGTAGCCAGCACGACAAGCCCGATC

AGCAGACAGCAGGCATG
```

This gene-specific promoter is a fragment of genomic DNA of maize that is likely to include promoter elements that allow the gene of SEQ ID NO:39 to exhibit nitrogen-regulated expression. Other suitable promoters include those having a nucleotide sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and/or SEQ ID NO:46.

The nucleic acid construct of the present invention also includes an operable 3' regulatory region, selected from among those which are capable of providing correct transcription termination and polyadenylation of mRNA for expression in the host cell of choice, operably linked to a modified trait nucleic acid molecule of the present invention. A number of 3' regulatory regions are known to be operable in plants. Exemplary 3' regulatory regions include, without limitation, the nopaline synthase (NOS) 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus (CaMV) 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would be suitable for use in conjunction with the present invention.

The different components described above can be ligated together to produce expression systems which contain the nucleic acid constructs of the present invention, using well known molecular cloning techniques as described in Sambrook et al., *Molecular Cloning: A Laboratory Manual*, Second Edition Cold Spring Harbor, N.Y.:Cold Spring Harbor Press (1989), and Ausubel et al. *Current Protocols in Molecular Biology*, New York, N.Y:John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs of the present invention. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, New York (1989), which is hereby incorporated by reference in its entirety. Suitable hosts include, but are not limited to, bacterial cells, viruses, yeast cells, mammalian cells, insect cells, plant cells, and the like. Preferably the host is either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose, particularly when the plant under investigation is slow-growing.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used. Further, particle bombardment transformation can be used to stably introduce the nucleic acid construct into plant cells.

Another appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., *Proc. Natl. Acad. Sci. USA* 79:1859-63 (1982), which is hereby incorporated by reference in its entirety). The nucleic acid molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention. Transformation can also be achieved using the "whisker" method, as is well known in the art.

After transformation, the transformed plant cells must be regenerated. Plant regeneration from cultured protoplasts is described in Evans et al., *Handbook of Plant Cell Cultures*, Vol. 1, New York, N.Y.:MacMillan Publishing Co. (1983); Vasil, ed., *Cell Culture and Somatic Cell Genetics of Plants*, Vol. I (1984) and Vol. III (1986), Orlando:Acad. Press, which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y.: Cold Spring Harbor Press (1989), which is hereby incorporated by reference in its entirety).

After the fusion gene containing a nucleic acid construct of the present invention is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants. The component parts and fruit of such plants are encompassed by the present invention.

The present invention can be utilized in conjunction with a wide variety of plants or their seeds. Suitable plants can include dicots and monocots. More particular, suitable plants can include the following: rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, petunia, pelargonium,* poinsettia, *chrysanthemum*, carnation, *crocus*, marigold, daffodil, pine, *Medicago truncatula, Sandersonia aurantiaca,* and *zinnia*.

Another aspect of the present invention is a method of expressing a nucleic acid molecule that is modulated by nitrogen in a plant. This method involves providing a transgenic plant or plant seed transformed with a nucleic acid construct having a nucleic acid molecule that is modulated by nitrogen in corn, a 5' DNA promoter sequence, and a 3' terminator sequence. The nucleic acid molecule, the DNA promoter sequence, and the terminator sequence are operatively coupled to permit transcription of the nucleic acid molecule. The method also involves growing the transgenic plant or a transgenic plant grown from the transgenic plant seed under conditions effective to express the nucleic acid molecule in the transgenic plant or the plant grown from the transgenic plant seed. In one embodiment, the transgenic plant or plant seed is provided by transforming a non-transgenic plant or a non-transgenic plant seed with the nucleic acid construct of the present invention to yield said transgenic plant or plant seed. In one aspect, the growing step is effective in reducing nitrogen uptake of the transgenic plant or the plant grown from the transgenic plant seed. In another aspect, the growing step is effective in increasing nitrogen uptake of the transgenic plant or the plant grown from the transgenic plant seed. In yet another aspect, the growing step is effective in increasing efficiency of nitrogen utilization of the transgenic plant or the plant grown from the transgenic plant seed. Transformation of the transgenic plant or plant seed can be achieved using *Agrobacterium*-mediated transformation, the whisker method, vacuum infiltration, biolistic transformation, electroporation, micro-injection, polyethylene-mediated transformation, or laser-beam transformation.

The present invention also relates to an isolated DNA promoter from corn suitable for inducing nitrogen-regulated expression of a protein encoded by an isolated DNA molecule operably associated with the DNA promoter. A suitable DNA promoter for use in this method can be any one of the promoters described herein, including, for example, the promoters having a nucleotide sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and/or SEQ ID NO:46. The isolated DNA promoter can be used to prepare nucleic acid constructs as previously described. In a particular nucleic acid construct, the isolated DNA promoter can be operably linked to an isolated nucleic acid that either has a nucleotide sequence (or encoding portion thereof) of SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:24, SEQ ID NO:27, SEQ ID NO:30, SEQ ID NO:34, SEQ ID NO:36, SEQ ID NO:39, SEQ ID NO:42, and/or SEQ ID NO:44, or encodes a polypeptide having an amino acid sequence of SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:25, SEQ ID NO:28, SEQ ID NO:31, SEQ ID NO:32, SEQ ID NO:35, SEQ ID NO:37, SEQ ID NO:40, SEQ ID NO:43, and/or SEQ ID NO:45. Other suitable genes from corn that can be regulated by the DNA promoter of the present invention include, for example, nitrate reductase, nitrite reductase, Uroporphyrin-III methyl transferase. Expression vectors can be prepared by inserting the nucleic acid construct in an appropriate vector (as described in more detail supra), and transgenic host cells and plants (including their component parts such as fruits and seeds) can be produced by transforming them with the nucleic acid construct containing the DNA promoter.

The present invention also relates to a method of directing nitrogen-regulated expression of an isolated nucleic acid in plants. This methods involves transforming a plant cell with the nucleic acid construct that includes an isolated DNA promoter suitable for inducing nitrogen-regulated expression of a protein encoded by an isolated DNA molecule operably associated with the DNA promoter. This method also involves regenerating a plant from the transformed plant cell. By this method, expression of the nucleic acid molecule, under control of the DNA promoter, occurs in the plant and is upregulated by nitrogen. A suitable DNA promoter for use in this method can be any one of the promoters described herein, including, for example, the promoters having a nucleotide sequence of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, SEQ ID NO:41, and/or SEQ ID NO:46.

Although preferred embodiments have been depicted and described in detail herein, it will be apparent to those skilled in the relevant art that various modifications, additions, substitutions, and the like can be made without departing from the spirit of the invention and these are, therefore, considered to be within the scope of the invention as defined in the claims which follow.

What is claimed:

1. An expression vector comprising a nucleic acid construct comprising:
a nucleic acid molecule that is up-regulated by nitrogen in corn;
a 5' DNA promoter sequence, wherein the DNA promoter sequence is a nitrogen inducible plant promoter; and
and a 3' terminator sequence, wherein the nucleic acid molecule, the DNA promoter sequence, and the terminator sequence are operatively coupled to permit transcription of the nucleic acid molecule, wherein the DNA promoter sequence is heterologous to the nucleic acid molecule, and wherein the nucleic acid molecule either:
(a) encodes a polypeptide having the amino acid sequence of SEQ ID NO:45; or
(b) comprises the nucleotide sequence of SEQ ID NO:44; or
(c) comprises the coding portion of the nucleotide sequence of SEQ ID NO:44.

2. The expression vector according to claim 1, wherein the nitrogen inducible plant promoter comprises a nucleotide sequence selected from the group consisting of SEQ ID NO:3, SEQ ID NO:6, SEQ ID NO:9, SEQ ID NO:12, SEQ ID NO:15, SEQ ID NO:18, SEQ ID NO:21, SEQ ID NO:26, SEQ ID NO:29, SEQ ID NO:33, SEQ ID NO:38, and SEQ ID NO:41.

3. A host cell transformed with the expression vector according to claim 1.

4. The host cell according to claim 3, wherein the host cell is a bacterial cell or a plant cell.

5. The host cell according to claim 4, wherein the host cell is a plant cell.

6. A plant transformed with the expression vector according to claim 1.

7. The plant according to claim 6, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana*, *Saintpaulia*, petunia, *pelargonium*, poinsettia, *chrysanthemum*, carnation, *crocus*, marigold, daffodil, pine, *Medicago truncatula*, *Sandersonia aurantiaca*, and *zinnia*.

8. A component part of the plant according to claim 6, wherein the component part comprises a plant cell of the plant, and wherein the component part comprises the expression vector.

9. A fruit of the plant according to claim 6, wherein the fruit comprises the expression vector.

10. A plant seed produced from the plant according to claim 6, wherein the fruit comprises the expression vector.

11. A plant seed transformed with the expression vector according to claim 1.

12. A method of expressing a nucleic acid molecule that is up-regulated by nitrogen in a plant, said method comprising:
providing a transgenic plant or plant seed transformed with the expression vector according to claim 1 and
growing the transgenic plant or a plant grown from the transgenic plant seed under conditions effective to express the nucleic acid molecule in said transgenic plant or said plant grown from the transgenic plant seed.

13. The method according to claim 12, wherein said growing is effective in increasing nitrogen uptake of said transgenic plant or said plant grown from the transgenic plant seed compared to an untransformed plant.

14. The method according to claim 12, wherein said growing is effective in increasing efficiency of nitrogen utilization of said transgenic plant or said plant grown from the transgenic plant seed compared to an untransformed plant.

15. The method according to claim 12, wherein a transgenic plant is provided.

16. The method according to claim 12, wherein a transgenic plant seed is provided.

17. The method according to claim 12, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca*, and *zinnia*.

18. The method according to claim 12, wherein said providing comprises transforming a non-transgenic plant or a non-transgenic plant seed with the expression vector to yield said transgenic plant or plant seed.

19. The method according to claim 18, wherein said transforming comprises *Agrobacterium*-mediated transformation, whisker method transformation, vacuum infiltration, biolistic transformation, electroporation, micro-injection, polyethylene-mediated transformation, or laser-beam transformation.

20. A recombinant nucleic acid construct comprising:
a nucleic acid molecule whose expression is up-regulated in corn by nitrogen;
a 5' DNA promoter sequence; and
a 3' terminator sequence, wherein the nucleic acid molecule, the DNA promoter sequence, and the terminator sequence are operatively coupled to permit transcription of the nucleic acid molecule, wherein the DNA promoter sequence is heterologous to the nucleic acid molecule, wherein the DNA promoter sequence is a nitrogen inducible plant promoter, and wherein the nucleic acid molecule consists of:
the nucleotide sequence of SEQ ID NO:44; or
the coding portion of the nucleotide sequence of SEQ ID NO:44.

21. An expression vector comprising the nucleic acid construct according to claim 20.

22. A host cell transformed with the nucleic acid construct according to claim 20.

23. The host cell according to claim 22, wherein the host cell is a bacterial cell or a plant cell.

24. The host cell according to claim 23, wherein the host cell is a plant cell.

25. A plant transformed with the nucleic acid construct according to claim 20.

26. The plant according to claim 25, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca*, and *zinnia*.

27. A transgenic fruit of the plant according to claim 25, wherein the transgenic fruit comprises the nucleic acid construct.

28. A transgenic plant seed produced from the plant according to claim 25, wherein the transgenic plant seed comprises the nucleic acid construct.

29. A plant seed transformed with the nucleic acid construct according to claim 20.

* * * * *

UNITED STATES PATENT AND TRADEMARK OFFICE
CERTIFICATE OF CORRECTION

| | | |
|---|---|---|
| PATENT NO. | : 9,523,099 B2 | Page 1 of 1 |
| APPLICATION NO. | : 14/462017 | |
| DATED | : December 20, 2016 | |
| INVENTOR(S) | : Patrick S. Schnable et al. | |

It is certified that error appears in the above-identified patent and that said Letters Patent is hereby corrected as shown below:

In the Claims

Claim 1, at Column 111, Line 29, delete "and".

Claim 10, at Column 112, Line 32, delete "fruit" and insert -- seed --.

Signed and Sealed this
Twenty-third Day of May, 2017

Michelle K. Lee
*Director of the United States Patent and Trademark Office*

SEQUENCE LISTING

```
<160> NUMBER OF SEQ ID NOS: 46

<210> SEQ ID NO 1
<211> LENGTH: 758
<212> TYPE: DNA
<213> ORGANISM: maize

<400> SEQUENCE: 1
cgactggagc acgaggacac tgacatggac ggaaggagta gaaaatattg cctgctccga      60
cgaccttgaa tattcactgg ccatttaatt tctacttaca agcctgaatg agctagagat     120
ccatctgctt ctgtacgtgc tcgtcaggta cgctcgtaaa aagaaaagaa aaaaaagaa     180 gagatcgaga tcgatctgtt gacgacgccc ccgtcgccga tatgggcgac ctctctgtcg     240
gccacagccg ccgctggtgc ggccgtttcg cggccgtcct ttgcctgtgc gcggccttct     300
gcaagccaga tgaactcccg atggatccac tgccgaactt gccgccgacg aggtcgctgc     360
agtgcttcga ggacgaacag gtgtacagct gctgcgaggg cgcgtacagg ctaaacccat     420
cgggaatcat cgccgttccc gtcggcgcgg tggactacta ctgcggcggc gcgtgcgtgg     480
tggagacgga ggacgtgctc aactgcgtgg ccagcgccct ggacggcttc gccttctaca     540
acggggcctc cgtggaggac gtgcgctacg cactcaggcg gggctgcagc cacaccgcca     600
gaagaggcga cttcaacgat ttggagccgc atctgggcga ctaccctgac atctatggcg     660
acgatgatga gcacagcttt ggcagcaagg ttgttgcagc tcctctgagg ttgctcgcgt     720
ttcttggcgg tgcggggctg ttcttcctgg gcccttga                             758

<210> SEQ ID NO 2
```

<211> LENGTH: 178
<212> TYPE: PRT
<213> ORGANISM: maize

<400> SEQUENCE: 2

```
Met Gly Asp Leu Ser Val Gly His Ser Arg Arg Trp Cys Gly Arg Phe
1               5                   10                  15

Ala Ala Val Leu Cys Leu Cys Ala Ala Phe Cys Lys Pro Asp Glu Leu
            20                  25                  30

Pro Met Asp Pro Leu Pro Asn Leu Pro Thr Arg Ser Leu Gln Cys
        35                  40                  45

Phe Glu Asp Glu Gln Val Tyr Ser Cys Cys Gly Ala Tyr Arg Leu
    50                  55                  60

Asn Pro Ser Gly Ile Ile Ala Val Pro Val Gly Ala Val Asp Tyr Tyr
65                  70                  75                  80

Cys Gly Gly Ala Cys Val Val Glu Thr Glu Asp Val Leu Asn Cys Val
                85                  90                  95

Ala Ser Ala Leu Asp Gly Phe Ala Phe Tyr Asn Gly Ala Ser Val Glu
                100                 105                 110

Asp Val Arg Tyr Ala Leu Arg Arg Gly Cys Ser His Thr Ala Arg Arg
            115                 120                 125

Gly Asp Phe Asn Asp Leu Glu Pro His Leu Gly Asp Tyr Pro Asp Ile
    130                 135                 140

Tyr Gly Asp Asp Asp Glu His Ser Phe Gly Ser Lys Val Val Ala Ala
145                 150                 155                 160

Pro Leu Arg Leu Leu Ala Phe Leu Gly Gly Ala Gly Leu Phe Phe Leu
                165                 170                 175

Gly Pro
```

<210> SEQ ID NO 3
<211> LENGTH: 4037
<212> TYPE: DNA
<213> ORGANISM: maize

<400> SEQUENCE: 3

```
ccgcaagagg gagtctttac cgagtgtcac ctaatacgct tggcgaagga cctggtaaaa      60
gggcccacag ggagctttt gctaagtgtc tgtacagtgg acactcggca aagagtgagc       120 cttttgccgag tgtcactccg tcaccgttac ctggtgtcgt gacgacggct tttctttgtc    180
gagtaccgag tgacactcga caaaaccttt gccgagcgtc cgataaaaag tattcggcaa     240
agaagccgtt gccgtctttg ccgagtgttt tccagacttt gccgagtgtt tcagacactc     300
ggcaaagaac ctgattccga tagtgaaggt cttacacccc gatccacccc aattcgtgcg    360
tattggagca agtacccaaa caaaaccgta ctgggaataa ttacctccgt tcgctgcagt    420
ttgcagaaca gcagttcaat gctacaggac gacgcagctg cagcgaacat gcatgcattt   480
gaactcactc cgttcactga tggacaagag gcatctgggt gactaataaa agaacgacac   540
acacggacag cttctagaag tattggtagc gcatgaacaa caatgccgct gttagcttgt  600
actgaggcac gaaacatgaa tctgacctac tactgacttc tactataata atagtatata  660
gtatggccag gccaggccaa ctccggcgaa acgggagta cgcatgcaga tggagcggca   720
cattagtagg ctgtttggtt tgaagaatgg gctagtctat catcttctca ctctccactt  780
ttttgtttgg tttgtggaat gaaatgagtt gattcatcat cacctcattc cttatagtta  840
gttagttagt actaatatga ggaatatggt catcccacca aatttgagga atggatccac  900
```

```
gatgtaccac cacattttgc atgaagtgat tcctcaaacc aaacaccccc aaatgtaaac    960
cgagtcatgc ctccgatccc aaccttcgtg tttcccacca acacacgcg tacagaggcc   1020
aagcacacgc acaaaagcaa gcctcgatcg tagcccgtgc ctaaccctgc cgatgccgta   1080
ataaacttgt gtgctccacg caaccatgaa atgaacctag aaatcgcagg ggcgggatgc   1140
gagtgaaaag gagcgggcag gtcaggtagg tttgaactct ctcctataat aatcctagct   1200
agcacacttg cccagattat attgcctgct ccgacgacct tgaatattca ctggccattt   1260
aatttctact tacaagcctg aatgagctag agatccatct gcttctgtac gtgctcgtca   1320
ggtacgctcg taaaaagaaa agaaaaaaaa agaagagatc gagatcgatc tgttgacgac   1380
gcccccgtcg ccgatatggg cgacctctct gtcggccaca gccgccgctg gtgcggccgt   1440
ttcgcggccg tcctttgcct gtgcgcggcc ttctgcaagc caggtgcgtg ctcaccgtca   1500
acacacgcac cattattcca ccctcccaag gagcacagta caacgcacgt acatataccct  1560
ctcctcaatc gatatatagt tacgtcttac gtactatcta gttaatctat cacgttgatg   1620
tctaatatag actccgcatg gcatatgcat gcagatgaac tcccgatgga tccactgccg   1680
aacttgccgc cgacgaggtc gctgcagtgc ttcgaggacg aacaggtaag ctaacaagca   1740
agagcgtgtt tggtttcatg ctaggacaga gttgcatacc acgtagctat cataagccta   1800
ccacacgtag ctatcacagc ctgtcgattt cgttcggtcg cctgacggta acatcgctg   1860
cccgagaggc gagctctttt tgacaagcct cgacgaacca aataagccaa gtcctactgt   1920
acgagggcga tcgaggcgcc gaggcctgtg tgatgtgatg ccgtgtgtcg tggtcaccca   1980
ccagctgctg tgtacattgg tccccgtgcc gcgcgtcgta accgcatgcg gcatgccgct   2040
gcatgcaggt gtacagctgc tgcgagggcg cgtacaggct aaacccatcg ggaatcatcg   2100
ccgttcccgt cggcgcggtg gactactact gcggcggcgc gtgcgtggtg gagacggagg   2160
acgtgctcaa ctgcgtggcc agcgccctgg acggcttcgc cttctacaac ggggcctccg   2220
tggaggacgt gcgctacgca ctcaggcggg gctgcagcca caccgccaga agaggtcccc   2280
aagtttctcg cctactagct catctctctc tacgtaccag ccaagctaga tcgactacca   2340
gtctccgcag cagtgcattc ggaacgaccg ctgacaaact gacaggctcg tgttcctgtc   2400
agcgcaggcg acttcaacga tttggagccg catctgggcg actaccctga catctatggc   2460
gacgatgatg aacacagctt tggcagcaag gttgttgcag ctcctctgag gttgctcgcg   2520
tttcttggcg gtgcggggct gttcttcctg ggcccttgaa cgaagatata aaagaactag   2580
cgatgtgatc cgcgtaaata tatactccgt atatagcatg acatgagtat ctagtttgtc   2640
ttatatggta aaccatacta aattttcttg tatggcatta aaaaaaatta agactttatt   2700
tagttatttg actagttgtt ctctctggat cctctaatca gttcgaactc tataagcttt   2760
tttattccac tcctatctag aggtcgcata atatgctaag gtgagatctt gatgtctttc   2820
gttttttaa ctcgataaag ttgttgtgag tctctcttat aaaattattt ttaatgctaa   2880
tattagattt tagtcagaga tatgcagttg accgttttgc actaaaatat tttgaattt   2940
actatagtat tagttgtcta ctaatcacag ctaaaccgt ttttattttt agttttttta   3000
taacagaaaa aatatctctg gaaacgaaaa cggcaacaca gtagttcaaa aatatcgaag   3060
acaataattt aacatgaaaa atatatatgt aatgatcgga atctaaaaaa caatcactaa   3120
atataaacat atagtaacat gtactctcaa ttgacctgaa aaaagcacat aacctataga   3180
tccacaaagt aacgaagatt gaagcatgaa aaatagacca tcatacatta aagggttgtg   3240
cttatttagc tctagaataa cctccttaag agcaacttca tttgcaacaa cattgtctag   3300
```

```
agttaaagag aatattttct tctctgtaaa ccatttcaat aagcatgaac tgggtctaag    3360
agacaaattc ttaccgttgt gccgacccag aacatgatcg aaatttgtaa ttcgcttctg    3420
tatttgtgaa tcatcatcta cccaatgtac catgatacac atgtaccttt tattctgatt    3480
tgatatccac atctccatgg tagcactgaa gtgacaatta agggttttaa aaatttata     3540 caacacatca tttttatgca aaagagatcc attacttctt ttctaacaat gacatgtgac    3600
tttatagaaa ataggcttt taaaggttta atgaaatcca taaagtattc atgttcaaga     3660
atgttaaatg ggtactcatg aatgataata gtagtataaa acttcctcaa actaattgac    3720
tcgtcatatt tatatggttg acaatatat agatatacct accttatgat cttttctga     3780 tttgagctcc tgctatctta gtaaaacctt atgataacgc ttctaatgca accaaaacta    3840
agttgttcct ctatggcttt tagcactacc tttgtaagtc ctattttgt agctcagaaa     3900 ctttcatttg gcccaaattt gctccagaga tttgcaattc ccctccacta caacaacata    3960
caaatcaaaa tactgccaaa catctaaagt atacttattt gctactttat ggggtgctca    4020
tcaacattag attcact                                                   4037

<210> SEQ ID NO 4
<211> LENGTH: 932
<212> TYPE: DNA
<213> ORGANISM: maize

<400> SEQUENCE: 4
ggacactgac atggactgaa ggagtagaaa atacagaacc ctgcaactgc aagctaagga      60
gagtgtgatc accaacagct agtgctagtc ccccttcctt ccatccatcc atggcatgcg     120
tcagcacctt ccagagctgc cccattgcca gaagagcaaa gatcaacacc aggtccaggg     180
gcagcagcag tagcgtggcg aaggggtcac caccaccagc cttccagttc cagtgcaggg     240
cgtcgacttt cgcggcggac accagcctcc ggctcgagct ggacgagaac cccgaggcga     300
tcatctcggg ggcgtggccc gggaactgct ccctcctcag ctacgacgac ctccgcgcct     360
acctcgagtc gcaggagacg gcggcccagg cagacgatca gcgcggcgtg gcgctcctga     420
gcgagaccat gtccacaccc gtgctggtgg ccacagcaga ccagaccctg gaggacgtcg     480
agtgccactt cgaggccgtg tcggggcttc cggtcgtcga cagcggcctc agatgcgtcg     540
gggtgatcgt caagaacgac cgggcaagag cctctcatgg gtccaagacg aagatatcgg     600
aagtgatgac atctccagct atcacactat cgtctgacaa accgtgatg gatgctgctg      660 ttctcatgct caagaagaag atccacagat taccagttgt aaaccaggac gaaaagtaa      720 taggtatagt tacccgcgct gatgttcttc gcgtgttgga aggcatgttg aagatttagg     780
agcgcagata cccatgctcg gaagccacag cctcttgtaa atatgtagat gtgcccgggc     840
atggtgtttc tgagtagcag caaagagatc taccatgtat aggagtttct ccttgtaaat     900
aatagtagca cgccaggaga ctccatccca gg                                   932

<210> SEQ ID NO 5
<211> LENGTH: 222
<212> TYPE: PRT
<213> ORGANISM: maize

<400> SEQUENCE: 5

Met Ala Cys Val Ser Thr Phe Gln Ser Cys Pro Ile Ala Arg Arg Ala
1               5                   10                  15

Lys Ile Asn Thr Arg Ser Arg Gly Ser Ser Ser Ser Val Ala Lys Gly
```

```
            20                  25                  30
Ser Pro Pro Ala Phe Gln Phe Gln Cys Arg Ala Ser Thr Phe Ala
        35                  40                  45

Ala Asp Thr Ser Leu Arg Leu Glu Leu Asp Glu Asn Pro Glu Ala Ile
    50                  55                  60

Ile Ser Gly Ala Trp Pro Gly Asn Cys Ser Leu Ser Tyr Asp Asp
65                  70                  75                  80

Leu Arg Ala Tyr Leu Glu Ser Gln Glu Thr Ala Gln Ala Asp Asp
                85                  90                  95

Gln Arg Gly Val Ala Leu Leu Ser Glu Thr Met Ser Thr Pro Val Leu
            100                 105                 110

Val Ala Thr Ala Asp Gln Thr Leu Glu Asp Val Glu Cys His Phe Glu
        115                 120                 125

Ala Val Ser Gly Leu Pro Val Val Asp Ser Gly Leu Arg Cys Val Gly
    130                 135                 140

Val Ile Val Lys Asn Asp Arg Ala Arg Ala Ser His Gly Ser Lys Thr
145                 150                 155                 160

Lys Ile Ser Glu Val Met Thr Ser Pro Ala Ile Thr Leu Ser Ser Asp
                165                 170                 175

Lys Thr Val Met Asp Ala Ala Val Leu Met Leu Lys Lys Lys Ile His
            180                 185                 190

Arg Leu Pro Val Val Asn Gln Asp Glu Lys Val Ile Gly Ile Val Thr
        195                 200                 205

Arg Ala Asp Val Leu Arg Val Leu Glu Gly Met Leu Lys Ile
    210                 215                 220
```

<210> SEQ ID NO 6
<211> LENGTH: 3987
<212> TYPE: DNA
<213> ORGANISM: maize

<400> SEQUENCE: 6

```
caacgtggag taggcaagcg ttggtcttgg ccgaaccacg ggataaacca ctgtgtcaac    60
tctgtgattg atctcttgtg gtattgtgtt ttgttgagac tcttttctag ccacttggca   120
tttagtgtgc taacacttaa caagttttg tggctataag tttaagtttt acaggatcac    180
ctattcaccc cccccccctc taggtgctct caagttgaca ggtgtctcca tggtgcctaa   240
ttgagccgtt cttttacgct atccattcga ttggtttggt gggtatgtgt ggtctggctc   300
ttgcgatgtt tgcccgctgg aaacgaaaca atcgtgcata cgtgcgcatg caattaacgg   360
tggtgttttt ggcctgtctt gcagcagcgg gtgcagcatt ggcttggcat aagcacgcaa   420
ccaaacaaag actaccttt ggtcaatgca tgcgaagaat ctgtacgagc gggcgtagac    480
aaccaatgat gcgatataaa atttaaggat tgaatcatat tagaatcgag ctttatttct   540
attcattttc gaactaattt tttaagtatc ctaacttatt gtgaagaaac gtaaatattt   600
agatcccgat ccattaccac ctctactcat acgtgaaacc aaacacgcgg aatatccttc   660
tggttcaaat atgcagaagt caatgagcag gacttctgct tgtttgttca gtctctcagg   720
cagggttaca ggaggcaata caagatgttc ccaacgatt ccctgaatcg ttcacccct     780
ctctcagtcc tatgattcac tcactcaccc ctccccctct tctccgtatg acaggaaatc   840
cccctagagg gggagagctc taagctcccc ctccactaat taatcatatt tactgtgaaa   900
ttacctattt gtagtgtaat taatagttag caatgtgtat tacgtattat aaatattgta   960
ccaatattta aaactcaaaa aactaatgta taaaaatcaa atagtgcact taagtatta   1020
```

```
agggcagagc tgaatagggg gattgttgga gaagtgaaga aataggggga agaatagttg      1080
agaaggggta tttaaatatg aatagaaagt atgaatggag ggaatgtttg agagagagctc     1140 aagaacaagg gacactgagc tgcctacaac acgtggccct ttttgtccct cttctttttt     1200
ttctttcgca tctgctggct acaagaggac acgcccttct attcgccgta tagagcagtg     1260
tctgtgaagt aaaagagaac tatcctccaa ggcttatttt gagtgtatta ctcctggatt     1320
cttgaatctt agctggtatg gtatggtaag gagttacgtt gtccaggaga ttccaactta     1380
cggatccaca ctgaaaagtt tgtattaccc atttgttagg ccccgtttca atctcacggg     1440
ataaacttta gcttcctgct aaactttagc tatgtgaatt gaagtgctaa agtttagttt     1500
taattaccac cattagcttt cctgtttaga ttacaaatgg ctaaaagtag ctaaaaaaag     1560
ctgctaaagt ttatctcgca agattggaac agggcctata tggtcacttt agagaggcat     1620
ggaggtttaa tagactatga cattcgtacg tggtcacctc aacaaacttt attgtttgac     1680
cgaaccatag attgaattgt gtgacattgt tctttgctcg tattattatt aatagaaagt     1740
aaccttcttg ggtgcggccc atacggtcct gagcgcacta aatgaggcct cattggccgc     1800
ggcccattcg atcctcaacg cactggataa agccagcgtg gcgtggctaa accacttcgt     1860
ttggcatggg cctgtcggtg cacttgccca aaccatgagc ttgtaccaaa actcgctagt     1920
ggtagtggta ttagtagtga agaacttctg caacttcaaa ctcaccgatt ctctcgcgt      1980 cagtttggaa gctaaaatat cggtggaaat tagagagaat ttgataagct aaaatctctt     2040
tattatttaa aattgaataa taaataaatt ttaactcctc caatcttctc cgttttatg      2100 tctcccaaac tcagtgtacc agatcatatt cctttcatta aaaaaaaggt gaacaaagac     2160
gccaccttat ccactgccac gtgacagggg gccaggggaa tctcggcggc cagtggcggc     2220
acgccacgcc ggccggtcgc ccccgtcgct gtacaagata cccatgattg gagcggggca     2280
ggtgcagagc agcaacgcca cggctgcatg agatcaagaa gctgccttca cttcgcccac     2340
tgcagcatgc cgtgtcgccg tcagagttgg gcgcatatcc agataaaaaa aacttgcctg     2400
cttgcactgc agatgcgttg ttttttgctaa cagcaagcag gcaagtcagc agcctaacct     2460
tctttgatat ttacagagaa gatgaaaagg agaactggag agcagtagtg gcagtcactt     2520
cactggtcaa gcattcctat ccacctcggc ccacctccac ctccctgaca gtcattttgt     2580
tatataaaac ccatcaagct cccctgcaag gagatacaga accctgcaac tgcaagctaa     2640
ggagagtgtg atcaccaaca gctagtgcta gtcccccttc cttccatcca tccatggcat     2700
gcgtcagcac cttccagagc tgccccattg ccagaagagc aaagatcaac accaggtcca     2760
ggggcagcag cagtagcgtg gcgaaggggt caccaccacc agccttccag ttccagtgca     2820
gggcgtcgac tttcgcggcg gacaccagcc tccggctcga gctggacgag aaccccgagg     2880
cgatcatctc gggggcgtgg cccgggaact gctccctcct cagctacgac gacctccgcg     2940
cctacctcga gtcgcaggag acggcggccc aggcagacga tcaggtacac ttcgatctcg     3000
cggcttcttc agttcttgtt accattgttt acatctcctc cagctcttgc taacccggcc     3060
tggacgggtc tcctcctctg tggatatata cagcgcggcg tggcgctcct gagcgagacc     3120
atgtccacac ccgtgctggt ggccacagca gaccagaccc tggaggacgt cgagtgccac     3180
ttcgaggccg tgtcggggct tccggtcgtc gacagcggcc tcagatgcgt cggggtgatc     3240
gtcaagaacg accgggcaag agcctctcat ggggtcagca cctcgctcct ctccctccac     3300
ctctttcttt ctcatggggc cagggccatg catgcgcatc aagctgctag tttctcatag     3360
```

| | |
|---|---|
| acaggcaaat aagaacgacg tacgtccgtt cagtttaccg gtctgtttct acttgtgaca | 3420 |
| gtccaagacg aagatatcgg aagtgatgac atctccagct atcacactat cgtctgacaa | 3480 |
| aaccgtgatg ggtaatcttt tttgcatcgc ttttcttttc ttttcttttc ttttctgttc | 3540 |
| atgtgtgatt tttaacaagt tgaatctaac agtgcatgcc taacgtctac agatgctgct | 3600 |
| gttctcatgc tcaagaagaa gatccacaga ttaccagttg taaaccagga cgaaaaagta | 3660 |
| ataggtacgg tgagtgagtg tcagaatgct cacaagccag cagagattaa aaaaaaaaac | 3720 |
| tgcatgccat acacttaatt agtattatcc ttaattatca ttgacaacac agagattata | 3780 |
| tgttgcaagg gctaatgggg ttctaaacac tgtcaacagg tatagttacc cgcgctgatg | 3840 |
| ttcttcgcgt gttggaaggc atgttgaaga tttaggagcg cagatacccca tgctcggaag | 3900 |
| ccacagcctc ttgtaaatat gtagatgtgc ccgggcatgg tgtttctgag tagcagcaaa | 3960 |
| gagatctacc atgtatagga gttctcc | 3987 |

<210> SEQ ID NO 7
<211> LENGTH: 1178
<212> TYPE: DNA
<213> ORGANISM: maize

<400> SEQUENCE: 7

| | |
|---|---|
| cgactggagc acgaggacac tgacatggac tgaaggagta gaaacccttc tcgctcggtt | 60 |
| gctcgggagc tttcccctttc ctgttcctga agcttccgac atccgaccgc ctcctcctcc | 120 |
| tcgttctact cgccgcccct tctagaatca tccagaggcg tgccggtgaa gcgcgagagc | 180 |
| ggtgaggcat ggcgatgcag acgggggtcg cgacctccaa ggtcctcatc ctcgtcggtg | 240 |
| cagggatgac gggctcgatc ctgctgcgga atggccgctt atctgatgtg ttgggagaac | 300 |
| tccaggagat tatgaagggt gtaaatcaag gaacttcttc gggtccctat gacattgcac | 360 |
| ttattcaagc tcagattcgg aatttagcgc aagaagtcag agatttgaca ttgtcaaagc | 420 |
| ccattaccat actgaatggc aaatctgact cgggaggcag tttatcatcc tacatactgc | 480 |
| cagcagcagc agttggagca atgggttatt gctacatgtg gtggaagggg ttgtctctct | 540 |
| cagatgtcat gtttgtcaca aaacacaaca tggcaaatgc tgttcagagc atgtcaaagc | 600 |
| agttggagca agtttcatca gcactagctg caacaaaaag acatctaact caacggcttg | 660 |
| agaatttgga tggcaaaatg gatgaacaag tagaggtctc caaagctatt agaaatgagg | 720 |
| tcaatgatgt taaagatgac ctgtctcaaa ttggatttga tgtcgaatca attcagaaaa | 780 |
| tggttgctgg attggaggga agatcgagt tacttgagaa caaacaggac gtggctaata | 840 |
| ctggtatctg gtatctctgc caagtagcag gcggtttaaa agatggaata aacaccaggt | 900 |
| ttttccagga aaccagtgag aagctgaagc tctcacattc agctcaacct gaaaacaagc | 960 |
| cagtgaaggg gcttgaattt ttttcggaaa gcaccatgga acagaaagta gctgactcca | 1020 |
| aaccaattgc ggtgacagtc gacgctgaga agcctgagaa aaccgctgct gtaatgggca | 1080 |
| ccacagtgca caggtctatc aggttctcat atcggaaggc aggccttgct ttgtgatcaa | 1140 |
| atcctctccg cttgagatgc acgtggcctt cctggttg | 1178 |

<210> SEQ ID NO 8
<211> LENGTH: 315
<212> TYPE: PRT
<213> ORGANISM: maize

<400> SEQUENCE: 8

Met Ala Met Gln Thr Gly Val Ala Thr Ser Lys Val Leu Ile Leu Val

```
                1               5                   10                  15
            Gly Ala Gly Met Thr Gly Ser Ile Leu Leu Arg Asn Gly Arg Leu Ser
                            20                  25                  30

Asp Val Leu Gly Glu Leu Gln Glu Ile Met Lys Gly Val Asn Gln Gly
                        35                  40                  45

Thr Ser Ser Gly Pro Tyr Asp Ile Ala Leu Ile Gln Ala Gln Ile Arg
                    50                  55                  60

Asn Leu Ala Gln Glu Val Arg Asp Leu Thr Leu Ser Lys Pro Ile Thr
            65                  70                  75                  80

Ile Leu Asn Gly Lys Ser Asp Ser Gly Gly Ser Leu Ser Ser Tyr Ile
                            85                  90                  95

Leu Pro Ala Ala Ala Val Gly Ala Met Gly Tyr Cys Tyr Met Trp Trp
                        100                 105                 110

Lys Gly Leu Ser Leu Ser Asp Val Met Phe Val Thr Lys His Asn Met
                    115                 120                 125

Ala Asn Ala Val Gln Ser Met Ser Lys Gln Leu Glu Gln Val Ser Ser
                130                 135                 140

Ala Leu Ala Ala Thr Lys Arg His Leu Thr Gln Arg Leu Glu Asn Leu
            145                 150                 155                 160

Asp Gly Lys Met Asp Glu Gln Val Glu Val Ser Lys Ala Ile Arg Asn
                            165                 170                 175

Glu Val Asn Asp Val Lys Asp Leu Ser Gln Ile Gly Phe Asp Val
                        180                 185                 190

Glu Ser Ile Gln Lys Met Val Ala Gly Leu Glu Gly Lys Ile Glu Leu
                    195                 200                 205

Leu Glu Asn Lys Gln Asp Val Ala Asn Thr Gly Ile Trp Tyr Leu Cys
                210                 215                 220

Gln Val Ala Gly Gly Leu Lys Asp Gly Ile Asn Thr Arg Phe Phe Gln
            225                 230                 235                 240

Glu Thr Ser Glu Lys Leu Lys Leu Ser His Ser Ala Gln Pro Glu Asn
                            245                 250                 255

Lys Pro Val Lys Gly Leu Glu Phe Phe Ser Glu Ser Thr Met Glu Gln
                        260                 265                 270

Lys Val Ala Asp Ser Lys Pro Ile Ala Val Thr Val Asp Ala Glu Lys
                    275                 280                 285

Pro Glu Lys Thr Ala Ala Val Met Gly Thr Thr Val His Arg Ser Ile
                290                 295                 300

Arg Phe Ser Tyr Arg Lys Ala Gly Leu Ala Leu
            305                 310                 315

<210> SEQ ID NO 9
<211> LENGTH: 3385
<212> TYPE: DNA
<213> ORGANISM: maize

<400> SEQUENCE: 9
taactctaca agctaagaat caacatgtat gcaattccat aataatcggg catcatctat      60
cactcattgc taacttcagc actgaacatg atttcaagag ttttttagcag aactactatg    120 cgggtgatct cctttcagat gtagatggtt tagaagtgta cataagcttg caggggctta    180
aggaactgtt tatttaatct tctgtgagca cgaacatcca tagaagaact atctgaactg    240
aagctaaaga tttgcatgaa atggtaattt gtacacatta agtgcatcat gcaaacagaa    300
cgagtacaca gtgaaacgat acagacctcc cgagtcagat ttgccattca gtatggtaat    360
```

-continued

| | |
|---|---|
| gggctttgac aatgtcaaat ctctgacttc ttgcgctaaa ttccgaatct aatatcaagc | 420 |
| acgagcatgc aaagttaagt agaaatgaat aattttaccg agatggaaag aagcaagaga | 480 |
| aacttctaag cagatgctga cactgagata gtgagatgta agatgtattc catatgagga | 540 |
| agagcatacc tgagcttgaa taagtgcaat gtcataggga cccgaagaag ttccttgatt | 600 |
| tacacccttc ataatctcct agaaacacaa aaggtacatc attgccttaa ataaacattt | 660 |
| actaggaagt ttcagagcat accatcaaaa tctgtatgat atgtatcagg aatcactaac | 720 |
| tagtgaagca taagttatgg tacgcaaaac ttccgagtgc caattgggcg ttgatgtaat | 780 |
| tttatcacat ggtgttaatc acatccacat atagacagaa tcaacgcttc tagtacccca | 840 |
| tcgccaagtc attcaaaaaa tatcaggtat cagctatctg acaacgctca actatccaaa | 900 |
| ccgtatgaaa gtgcgtgtaa tcaaaatgaa catattttt tcggggttgg gtgtgggggg | 960 |
| tataccgacc tggagttctc ccaacacatc agataagcgg ccattccgca gcaggatcga | 1020 |
| gcccgtcatc cctgcgagga caccatttca ccacgtaagg tgtcgaaaca acagccgatt | 1080 |
| ggggaaaata gcatcaaatc cgagagagat ttgatggggg cgagaggtcg atggcggtga | 1140 |
| tgagaagagg acctgcaccg acgaggatga ggaccttgga ggtcgcgacc cccgtctgca | 1200 |
| tcgccatgcc tcaccgctct cgcgcttcac cggcacgcct ctggatgatt ctagaagggg | 1260 |
| cggcgagtag aacgaggagg aggaggcggt cggatgtcgg aagcttcagg aacaggaagg | 1320 |
| ggaaagctcc cgagcaaccg agcgagaagg gtgcctggac ccgggaccgg gacctgagaa | 1380 |
| tttcgtgtgt cacaaacaaa cagggtgaac cagttgtgaa atgggaccac gtgtcagtga | 1440 |
| agaggtgagt agtagtattt gtgagttgtg actcgagaaa tgccgctgcg ggctgcggcc | 1500 |
| tagccacagc cacgtcagca atgtcgaaag tcgaaaccaa ccccactcca cgtctccccc | 1560 |
| aggagaagcg accattcaaa gccgccggga gctcggcgtc accgccgcga gctcgacacc | 1620 |
| tcgacacctc gtgccgccgc agcgcttgct ttcgtccccc ttacgccact cccacttggc | 1680 |
| cacttcagcc accatctccc tgaagctagt ggctaacctc ctcaccgcca tgggcacccc | 1740 |
| tctcctcatc ccccttctcg tcaccctcca gctgttcact acctcctccc ccgcggtcgc | 1800 |
| gtcgtcacac atctccgcca tcatctcgca gtcgggcctc gacttcgcca aggacctgct | 1860 |
| cgtatcccat gccgttgcga ccctcacgcc catgaacgtg ccggacatcg agaggaccat | 1920 |
| gagcataccc ctcgtgggca ccgtccgcat ggccgcatcc gggattgtgc tccacggcct | 1980 |
| cgccgtcacc aactccaccg tcgctgtggg ggacgcgggt gttgtcgtgg ccgcctcgtt | 2040 |
| ggccagcgcg aacctcacca tggagtggaa ctactcgtat gacgcctgga ttgtgaccat | 2100 |
| atccgacagc gggaatgctt cggtccaggt ataaatgagg ggaacatata ctgtgcagtc | 2160 |
| atattagtgc aaccgtgcaa ttaagcaatg atgcatcgat ccaatcaaaa tccaactatg | 2220 |
| attgctattt taggtggaac atggttagat gcaaacagt cctgtttggt tgatattcga | 2280 |
| tattccatca gttatgttcc ccaaggcgtg gcttgctgat tggtggctgt taattgaatc | 2340 |
| ataagatact gcccgttttt ttaatatact gagtaggaga tatacgcatc ttttatgcta | 2400 |
| ttaagtatag actgatcgcg cgacacttga atttggaat atctattttc tgtcagatgt | 2460 |
| cagaagtaga atcaattatc ttagaagtgg gtgctaattc acacctatta ctatatttaa | 2520 |
| aatgggatta atataaacac tctattttc tcgaaagcgc aagagagctg cgcgaaaata | 2580 |
| tattaagaag aagtaaaagg tccaaaagga ccccaagata cagataaggc cgacctacgg | 2640 |
| cggcaaataa caagcataaa tgaaaccatc catgacaaaa acactgctac cagaacagca | 2700 |
| ctacatctat ctagctaaca ggtagacctg ggataggggc agtaagcaag gacagcttct | 2760 |

```
ttgcaccagc cataacccaa agatcaatct ccaaaccaac acttctaata gcaacagcaa    2820
cactaggact cttattgtca aaaacgtagc cattgcgatg tttccaaagg gtccaaacac    2880
caagaatgac aagagaatta agaccatttc ttgcaatccc aggagtcttg gtgatcaagt    2940
cttgccacca atccataaaa acctcttcac aggactgatg ggccaagtgt tgtagattta    3000
caagaagaag cagcttgaac caaaattctc tagcaaaaac gcagcccagc agcatatgat    3060
ttaaggtttc ctgatcctga tcacataatg gacatctctc cggatgatcc atacctcttc    3120
tttgcaacct atcagctgtc cacaccttct tgtgagcgac caaccacatg aaaaatttag    3180
atttcggagg agcccaagtc ttccaaatta tatgaaaagg ctcaaactca attgacccaa    3240
taaagaaacc cctataagct tccttggaag aatattttcc attggcagca aggcgaaaga    3300
aatgcttgtc ttcaacatga ggtcttagct gaaccaaatc taataaatcc cacaagagga    3360
gatactcgtt gatacaccca ctgaa                                         3385

<210> SEQ ID NO 10
<211> LENGTH: 420
<212> TYPE: DNA
<213> ORGANISM: maize

<400> SEQUENCE: 10
cgactggagc acgaggacac tgacatggac tgaaggagta gaaaaactcc caaatccttc     60
gtttcgtcgt ctccacacgc aatagcatcc gagcaaagaa gccaaagagc aactgggagc    120
gaggacggga ggcaacaagc ggcggcggca tggaccggaa cctgagcggg tttctgatcg    180
ggtgcctggg cgccgccgtg acgctgctgg cgtaccagca gacggtggtg accagcacgc    240
agagcgtcgc ggcgggcttc gtcgtcatcc tcttcgccct cttcgtcaag gaaggattca    300
tttccctctg aatctctggt gcgcgtcagc cagccatgca tgaggaggcg tcatcgctcc    360
gctgcctgta tttctgctcg ctagttcagt cccgcagctg ccgctgtgct cgtcaggttc    420

<210> SEQ ID NO 11
<211> LENGTH: 53
<212> TYPE: PRT
<213> ORGANISM: maize

<400> SEQUENCE: 11

Met Asp Arg Asn Leu Ser Gly Phe Leu Ile Gly Cys Leu Gly Ala Ala
1               5                   10                  15

Val Thr Leu Leu Ala Tyr Gln Gln Thr Val Val Thr Ser Thr Gln Ser
            20                  25                  30

Val Ala Ala Gly Phe Val Val Ile Leu Phe Ala Leu Phe Val Lys Glu
        35                  40                  45

Gly Phe Ile Ser Leu
    50

<210> SEQ ID NO 12
<211> LENGTH: 1736
<212> TYPE: DNA
<213> ORGANISM: maize

<400> SEQUENCE: 12
gatacgactc tcgctggtat ataaaatctg tttcgtagat aaacatgaaa ccagaatttt     60
tgatcaccat atacttgttt cagaagcaaa ttggggacac catatacttg ttgccttcaa    120
acgaccgtac aataagttca gactgaccat ctgaatgtca caagagctag tttagagcag    180
```

-continued

```
caagaaattg tcaagtgacc tagacatccc gaaccgacgc ttcccagact tagcccgacc      240
ttccgggtcc ttcataagct gactccgtgg cccctcacca gaccaacgcc gcagccgttg      300
accttgcggc tttttatccc catccggcca tccccaaccc aactcccaaa tccttcgttt      360
cgtcgtctcc acacgcaata gcatccgagc aaagaagcca aagagcaact gggagcgagg      420
acgggaggca acaagcggcg gcggcatgga ccggaacctg agcgggtttc tgatcgggtg      480
cctgggcgcc gccgtgacgc tgctggcgta ccagcagacg gtggtgacca gcacgcagag      540
cgtcgcggcg ggcttcgtcg tcatcctctt cgccctcttc gtcaaggaag gattcatttc      600
cctctgaatc tctggtgcgc gtcagccagc catgcatgag gaggcgtcat cgctccgctg      660
cctgtatttc tgctcgctag ttcagtcccg cagctgccgc tgtgctcgtc aggttcttgg      720
aaaaatactg taatagcgta gtgacttttta tgtacgacac ggatggttgt tgctggctga     780
agggtctact ctgtcgaaat cgatgtatct tagtttatgc tacttgaaga acagcagact      840
gcagatcagc agagttcttg ccttcttacg ctaattaata attattggta cacgaatcct      900
gattgtgttg agccttcttg ccgttgctcc ttccctacta catctcggc ttgccaattc       960 acctatgtat gtttgctttg tatattagtg caggtattaa tggccgcctg taagtgagtt     1020
tgttctccct tgttgaacta ataaaattgg catgaattca ccccaaaaag attgatgctg     1080
tttctcacta gttttcagcc tcagacgact atagatgtcc aaacagtgcg gaccgtccat     1140
ttgaaacttg acccgtcacg attttagtcc ggtccaagca tggccaagca gggttggtaa     1200
cggcacgacc tgtttagcgt gccgggtttg ggcagctaca gaggcccgcg tgttttggtc     1260
cgatccgaca cgagcaatgg gccgacacag cggcggccca ttttcatat ggcatatggt      1320 gccagcggcc acacgccccc ccaaccaggc cacacacccg aaccctatct ctaatcccct     1380 cacccctcg ggccctccgt ccccatctct agcgattcgg cgccgtcgtt ctcgcccgtt      1440 gcatccgtc ggctcttgac ctcgacggcg gacgactctc catcgctgtc gtatgtggtg      1500
ctccgacctg cttggacttg gagttcctcc gtcctccctc gtcactccct ccgtctgcga     1560
ctggggactc cctaacccta acccctccgg tctccggatt cggtggttct agctcctcag     1620
ctgtgcaagg ttcgtttatc tcgtctaatc ccctccagat ttggtgtcta gctgatgtct     1680
ggtgctcgtc tgtggtgtct ggttgccgtt gccggtggtc gtcacctgtt gctcct         1736
```

<210> SEQ ID NO 13
<211> LENGTH: 791
<212> TYPE: DNA
<213> ORGANISM: maize

<400> SEQUENCE: 13

```
cgactggagc acgaggacac tgacatggac tgaaggagta gaaatcttgg atctggtggt       60
gggttcatcc ttggcccact tcttcttgag cttgggtgca taccgcaggt ggcaagtgca      120
acagcaacat tcgtgatgat gttctcctcc tccctctctg tggtggagtt ttacttcctg      180
cacagattcc ccctgccttt tgctggctac ctcatcttca tttccatatt ggctggattc      240
tggggccagt gtttggttag gaagatcgtg catgtgctca agagagcatc gcttattgtc      300
ttcatcctct cctctgttat cttcgtcagt gctcttacga tgggtgtcgt tggaacccag      360
aagagcattt cgatgatcaa caatcacgaa tatatggggt tcctcaactt ctgcgagtaa      420
ctcaaacacc atcagactgt cgatccgtcc gggagaatcc aggccaatgc ctaattgacc      480 tcatctcccct caaaatctag aagaataaag tcgccgagta tgtgcacaag ttagctcctc      540
gccaacatgt gcgcatttag accgacagag tcgctgtagt gaattcagct cgtgttagct      600
```

```
cctggctaac gagctgacca tacggcttta gttttgtgaa gtgggcgcga tttcgtcatg    660
tcatgcatgt gttagctcct ggctaacctg caaatgcgtg tgttggtgca ggttttgtc    720 acgtctgcgt cagctcctgg ctgaccagca gttgtttgtc gttcattctc tgcgtcagct    780
cctggctgac c                                                          791
```

```
<210> SEQ ID NO 14
<211> LENGTH: 94
<212> TYPE: PRT
<213> ORGANISM: maize

<400> SEQUENCE: 14

Met Met Phe Ser Ser Ser Leu Ser Val Val Glu Tyr Phe Leu His
1               5                   10                  15

Arg Phe Pro Leu Pro Phe Ala Gly Tyr Leu Ile Phe Ile Ser Ile Leu
            20                  25                  30

Ala Gly Phe Trp Gly Gln Cys Leu Val Arg Lys Ile Val His Val Leu
        35                  40                  45

Lys Arg Ala Ser Leu Ile Val Phe Ile Leu Ser Ser Val Ile Phe Val
    50                  55                  60

Ser Ala Leu Thr Met Gly Val Val Gly Thr Gln Lys Ser Ile Ser Met
65                  70                  75                  80

Ile Asn Asn His Glu Tyr Met Gly Phe Leu Asn Phe Cys Glu
                85                  90
```

```
<210> SEQ ID NO 15
<211> LENGTH: 2189
<212> TYPE: DNA
<213> ORGANISM: maize

<400> SEQUENCE: 15
cttgggcggt agagcttttt attagctttt caaaaagttc aaggtcatca aggtcagagt     60
ttaaatctaa aagctatgcc taaaatataa aatgggtcat actgagcacc catacatatg    120
atgatcttgt ccagtaccac atctgataca cacagagcat tacggtgacc catgttccat    180
atcttaaggt aacgaaggtt tgtcctaagt taaagttttg aaactttgac aacaatatct    240
acaaaaataa ttatttttta cttaaagaaa ttatatattg tgctagatgt tttaataata    300
aatataatag ttttattttt atttagtcaa tgtttatgaa tattttgtta ttaatgataa    360
aagtttcaaa attttgactt agtataaact ttcgtgatct taagataggg aagagaggga    420
gtgagtaggt atcaattgca cccaggtaat gatcattttc aacggtcaaa ttactaaaaa    480
tagccgttac caaaaactca acagtgtaca tgatgtggag cgatccgggg ggagacaccc    540
acttacgttc aatgaaaatg ctagtccacg aaggagacgg aagcccaccc tggcctctct    600
ttgaggcgaa gccacgttcc ggccaatcgt ctcacagcct ctatgcaggc tggaatgtca    660
cccatgctgc acctcacctc aaccatcgta atcttaagg accattcttc ttaattaact    720
catttgcaag ggtttgtagc gccgctttac cttagtacat gtgttacagt aaacaaacaa    780
ttgccagtgc tttatatgat ttcgatccat catattttag gtccaaaaca gcatcttcac    840
tcaaagagac agattaaagc tgtttggact gctttagcta taataaaaat actgtagaaa    900
aaacagaagt cggtggaagc cgcagcgaac atgttctgat tttcacggaa atacggcttg    960
aaacgcactc ggcttgcaca aacagaatgg gaattgactg atatttacaa tgttccatgc   1020
aacaaatatt tgcagttttg cagcctagcc tggtgctagc gcaagaatga acaacaaata   1080
```

```
actgctggtc agccaggagc tgacgcagag aatgaacgac aaacaactgc tggtcagcca      1140
ggagctgacg cagacgtgac aaaaacctgc accaacacac gcatttgcag gttagccagg      1200
agctaacaca tgcatgacat gacgaaatcg cgcccacttc acaaaactaa agccgtatgg      1260
tcagctcgtt agccaggagc taacacgagc tgaattcact acagcgactc tgtcggtcta      1320
aatgcgcaca tgttggcgag gagctaactt gtgcacatac tcggcgactt tattcttcta      1380
gattttgagg gagatgaggt caattaggca ttggcctgga ttctcccgga cggatcgaca      1440
gtctgatggt gtttgagtta ctcgcagaag ttgaggaacc ccatatattc gtgattgttg      1500
atcatcgaaa tgctcttctg ggttccaacg acacctgaaa ctcaccgaaa caagaggcca      1560
ttaggagaga agttaaaaat caaactagat tgatttagac gaaacaagta aaagagctaa      1620
tataatgcta catccgttct cgaatatttg tcgtccgtta gttcattttt taaaatgaac      1680
taaaacgtga caaataaaaa agaacggaga atggagtgag tattccttaa gattattttt      1740
ctcaaggatg catgctataa ttgcaaaatc aatttaagca acaccggtac gtttagttca      1800
atttaagcaa caccggtacg tttagttcaa ttcaacttgg agcggtatca ggttagcaat      1860
ttgccaagtt taaagctaag tagcaagtca atgagttatc aataggttca tacccatcgt      1920
aagagcactg acgaagataa cagaggagag gatgaagaca ataagcgatg ctctcttgag      1980
cacatgcacg atcttcctaa ccaaacactg gccccagaat ccagccaata tggaaatgaa      2040
gatgaggtag ccagctgcag atagagaaac agtgcaagtt attaactcgt taccatataa      2100
caatcacact tatgaaaacg tctacatttt gaggaattgg aatctaacta atagagtagg      2160
ttatttcttt agaacgtgac atttcataa                                        2189

<210> SEQ ID NO 16
<211> LENGTH: 839
<212> TYPE: DNA
<213> ORGANISM: maize

<400> SEQUENCE: 16
cgactggagc acgaggacac tgacatggac tgaaggagta gaaaaaagtg ctcccggaag       60
actccaagct gcagctaccg gccttcctct cccccattcc aattccgaga acaggggcgg      120
cggagtcaac caggtacgat gtgctcggta gcgaggctgg cgtttgtgct tgcactggcc      180
atagccgcct cgtcaattga ggttgcggag agcagagatt ttaatatctt tgctcagggc      240
agcttgcctg atgcaaccaa gggatcgtct ggtctagctg caaccagtgg aaagttgtgt      300
cagttatgcg agcagtactc atccgaggcg ctcctctatc tcacacaaaa cgagacccag      360
actgagattc ttagcattct acaccatgaa tgtgccagcc ttgcccctct caaacagcag      420
tgcatcacgc tggttgacta ctacgtaccc ctttctcttct tggaggtctc catggttacc      480
cctgagaagt tctgcgagtc gatgcatctc tgcaagaagg ggatgaagat tagcctaccc      540
acccgggagg gtacttgtgg tttgtgccac catgttgttg ttgaaattct tatcatgctt      600
aaagacccca acatgcagct ggaagtaatc gacctactca ccaaaacatg cagcaaggcg      660
cagaactatg aacagtagtg caagcggctg gtcctcaagt atattccact tattctggtg      720
aagggccaga aattccttga cacaacggat gtctgctctg tgatacatgc atgcaaagca      780
ggcacacaag catcaatgga agccatgcct ctgtctgcca tgttgtgaag gtgatgcga       839

<210> SEQ ID NO 17
<211> LENGTH: 179
<212> TYPE: PRT
<213> ORGANISM: maize
```

<400> SEQUENCE: 17

```
Met Cys Ser Val Ala Arg Leu Ala Phe Val Leu Ala Leu Ala Ile Ala
1               5                   10                  15

Ala Ser Ser Ile Glu Val Ala Glu Ser Arg Asp Phe Asn Ile Phe Ala
            20                  25                  30

Gln Gly Ser Leu Pro Asp Ala Thr Lys Gly Ser Ser Gly Leu Ala Ala
        35                  40                  45

Thr Ser Gly Lys Leu Cys Gln Leu Cys Glu Gln Tyr Ser Ser Glu Ala
    50                  55                  60

Leu Leu Tyr Leu Thr Gln Asn Glu Thr Gln Thr Glu Ile Leu Ser Ile
65                  70                  75                  80

Leu His His Glu Cys Ala Ser Leu Ala Pro Leu Lys Gln Gln Cys Ile
                85                  90                  95

Thr Leu Val Asp Tyr Tyr Val Pro Leu Phe Phe Leu Glu Val Ser Met
            100                 105                 110

Val Thr Pro Glu Lys Phe Cys Glu Ser Met His Leu Cys Lys Lys Gly
        115                 120                 125

Met Lys Ile Ser Leu Pro Thr Arg Gly Thr Cys Gly Leu Cys His
    130                 135                 140

His Val Val Val Glu Ile Leu Ile Met Leu Lys Asp Pro Asn Met Gln
145                 150                 155                 160

Leu Glu Val Ile Asp Leu Leu Thr Lys Thr Cys Ser Lys Ala Gln Asn
                165                 170                 175

Tyr Glu Gln
```

<210> SEQ ID NO 18
<211> LENGTH: 1961
<212> TYPE: DNA
<213> ORGANISM: maize

<400> SEQUENCE: 18

```
gcactcatag cacatctgag gttccctttc ttgaacttag ctcacctact gttcatagtt    60
ctgcgccttg ctgcatgttt tggtgagtag gtcgattact tccagctgca agcttgcagc   120
aaacaaagaa aggcattaca gtatgtacag agtacagagc agtacaacac agaagaatgt   180
tggtgacaga tagtgaaaat atggttatta cctgcatgtt ggggtcttta agcatgataa   240
gaatttcaac aacaacatgg tggcacaaac cacaagtacc ctcccgggtg gtaggctaa    300
tcttcatccc cttcttgcag agatgcatcg actcgcagaa cttctcaggg gtaaccatgg   360
agacctccaa gaagaaaagg ggtacgtagt agtcaaccag cgtgatgcac tgcagcaggg   420
tgaatcatca acacaacatt taacacagct gaaaacgtgg taccaatgga aggatcacaa   480
gttacctata cctgctgttt gagaggggca aggctggcac attcatggtg tagaatgcta   540
agaatctcag tctgggtctc gttttgtgtg agatagagga gcgcctcgga tgagtactgc   600
tcgcataact gacacaactt tccactggtt gcagctagac cagacgatcc cttggttgca   660
tcaggcaagc tgccctgagc tgaattgaag acagaagaaa ggattggcca gaaatgcaaa   720
acttcagaaa aacttgagtt cctgtgagga atagcagcta agctgaagct acgccctcta   780
cattgagtag aactgatggc ttagacgtaa ttgctttctt taacatgtca ccggactaaa   840
tgaagatacg aacttgtcaa acaaagaagg aatttagata aactaattga aactatcacg   900
agatctccat cgaaagaaa ctatcactag acctgataat tcactgctat ggatcaacat   960
tcaacaaaga ataaagagag taaggagcaa aaatcagtag attgaaagct taccaaagat  1020
```

```
attaaaatct ctgctctccg caacctcaat tgacgaggcg gctatggcca gtgcaagcac    1080
aaacgccagc ctcgctaccg agcacatcgt acctgcttac cactaccagt tggtcagttg    1140
acaggaacaa aactactgct tgaagaaaac tatcgcagtg aaatcagctg tggctgatgg    1200
acgcagaaaa gctggcttgc tcaaagcttc tccataaagc caaaaggtaa ccaaaaaaaa    1260
aagagaaagg aaatgtatcc tagggccctc tctctacgtc atgtaacgga tcagtagaag    1320
tttcagattc attcagcccg acgtaactga agaattcagt tcgcttcaag atgtagccat    1380
cagattcacg tatttggagt caagccaaga tagtaccaat tggtccgcat ccacattcca    1440
ggcaacagat tcacgagatt cagctcgctc cacgccagca gagctgctac tattctggca    1500
ccactccaaa tacgcctttg cagcagatta gcaaagcatt ttacgctcgc ttttgcgctt    1560
tattttgccc ctcgtttcct ttccaggtag cttccggttc cgaagaatcg gaggtccttg    1620
gattcaggga caaggggtcg aactgggcag caaatcaaga accgagggga gacggtagta    1680
cagagagccc aggagaagct aacatatgaa tggggaatta agacgcatc tcacctggtt     1740 gactccgccg ccctgttct cggaattgga atgggagaga ggaaggccgg tatctgcatc     1800
ttggactctt ccgggagcac tttgttttct taaagcttcg tgttacatta agaagatgca    1860
tgagcatgta gaacagtgtg tgtggccgtg tgtgtgagaa cctgagatat ttttgcttct    1920
ttggtggcca agatgtgtta gaaaggcata atcttttctt a                        1961
```

<210> SEQ ID NO 19
<211> LENGTH: 589
<212> TYPE: DNA
<213> ORGANISM: maize

<400> SEQUENCE: 19

```
cgactggagc acgaggacac tgacatggac tgaaggagta gaaatatagc cagaactctt      60
gcatcctggt gatggtaaac tgccgtgcca gtataaacgc gaaggcaggt cacacatact     120
cacaagtccg tcccatctca ggtcatccat ccatccatcc ctgcagcaat ggcgtctgca    180
gtgaccagca gcgacaagga gcaggccgtc cctaccatcg acgctgacga agcgcacgcg    240
ctgctgagct ccggccatgg ctacgtggat gtcaggatgg ggggggactt ccacaaggcg    300
catgcgcccg gtgctcggaa cgttccctac tacctgtccg tcacgccgca agggaaggag    360
aagaacccac actttgtaga ggaagtggct gccttctgtg ggaaggatga tgtcttcatt    420
gtgggttgca acacggggaa cagatccagg ttcgcgacgg cagaccttct gaacgcgggg    480
ttcaagaacg tgaggaacct gcaaggtggt taccgctcct ttcagcagcg agctcaacag    540
cagtagacat cacgtcctga aggtatgcca gggatgctgc agttgaacg                589
```

<210> SEQ ID NO 20
<211> LENGTH: 125
<212> TYPE: PRT
<213> ORGANISM: maize

<400> SEQUENCE: 20

```
Met Ala Ser Ala Val Thr Ser Ser Asp Lys Glu Gln Ala Val Pro Thr
1               5                   10                  15

Ile Asp Ala Asp Glu Ala His Ala Leu Leu Ser Ser Gly His Gly Tyr
            20                  25                  30

Val Asp Val Arg Met Arg Gly Asp Phe His Lys Ala His Ala Pro Gly
        35                  40                  45

Ala Arg Asn Val Pro Tyr Tyr Leu Ser Val Thr Pro Gln Gly Lys Glu
```

```
            50                  55                  60
Lys Asn Pro His Phe Val Glu Glu Val Ala Ala Phe Cys Gly Lys Asp
 65                  70                  75                  80

Asp Val Phe Ile Val Gly Cys Asn Thr Gly Asn Arg Ser Arg Phe Ala
                 85                  90                  95

Thr Ala Asp Leu Leu Asn Ala Gly Phe Lys Asn Val Arg Asn Leu Gln
            100                 105                 110

Gly Gly Tyr Arg Ser Phe Gln Gln Arg Ala Gln Gln Gln
        115                 120                 125

<210> SEQ ID NO 21
<211> LENGTH: 2277
<212> TYPE: DNA
<213> ORGANISM: maize

<400> SEQUENCE: 21
```

| | | | | | |
|---|---|---|---|---|---|
| cgcactaaga | aggcagggaa | ttgtgtggca | aatataggta | catgctacac | gtgtgatatt | 60 |
| tcccgatttg | tcaatctggg | acatgaagtt | aacatcgcaa | attataatgt | tacaggaacc | 120 |
| aggtatggtg | ctagcttgcg | taagcaaatc | aagaagatgg | aggtatctca | gcattccaag | 180 |
| tactttgcg | agttctgtgg | gaaggtacat | ttctgttagt | taccctgttt | ctgcatccaa | 240 |
| gttttctaat | ctttgatcta | ttgaactgcg | agctgtcttt | atgttgtact | cgttatcatc | 300 |
| accactgctg | ttatgaaatg | taggctgcag | tcagattgat | tttgagcaca | tgaaatcaat | 360 |
| tagttttcga | tatatctgtt | tgtcacaagc | acatgaaatc | aattagtctt | cgatatatct | 420 |
| gtttgtcaca | tttgaatgat | ttataagatg | tctgggcatg | tccatcaatg | tgtttctaag | 480 |
| atacatttga | agacagacag | catttgttcc | gaatccaacc | tttgctgtgc | tgtgtttcca | 540 |
| gtttgctgtg | aagaggaaag | cagttggaat | tggggggtgc | aaggactgtg | ggaaggtgaa | 600 |
| ggctggtggt | gcttacacca | tgaagtaagt | aattcttcgc | ctgtccgaaa | accacaattt | 660 |
| gttagccacg | gctaaattct | gttaatgtgt | ttgcagcact | gctagtgcgg | tcaccgtcag | 720 |
| gagcacgatc | cgccgcctga | gggagcagac | tgaagcatga | tatagctctt | tatattattg | 780 |
| gggtttcctg | tagttgctct | tgtcaggcat | gttgtggggg | ccttatctag | tggaaatgtg | 840 |
| gaatcactgt | actggctgtt | tgccgagac | aatgctcctt | atatttggtt | tatgctctag | 900 |
| gatctcaaag | ttgtgttaag | atttgcccctt | ggttaccgtt | ctgaatctga | caagtgatat | 960 |
| ttcatcctat | gccatcttga | cgtcgaattt | ggttgtggtt | ttctatgcgc | ttggctgtgt | 1020 |
| caatggtttg | ctattctgtt | cttgaaattc | tacagatact | gctgcgtctc | tgctggttga | 1080 |
| gtctggttta | gatagcaacc | agtccttatt | attggtcttt | caagttcaag | tcaactaaaa | 1140 |
| tgcgacaaat | aaaaaaaaga | atggagggag | tatataactg | ttcaagtcaa | ccaatcctta | 1200 |
| ttacgcctgc | acttgtgtcc | aaaaagaaat | gccccggagc | tattattggt | ctgttgccag | 1260 |
| ataagcagtg | acgacgcagc | atcgaaggtc | agagacgact | tttttgcgag | aacgagcatc | 1320 |
| aagctgacgg | aatggagcat | tattccgata | aaaaaaaggt | atagccagaa | ctcttgcatc | 1380 |
| ctggtgatgg | taaactgccg | tgccagtata | aacgcgaagg | caggtcacac | atactcacaa | 1440 |
| gtccgtccca | tctcaggtca | tccatccatc | catccctgca | gcaatggcgt | ctgcagtgac | 1500 |
| cagcaggtaa | acatagcttc | tgagtgcatc | tgatgttgct | tacagtaaca | ttacatgcat | 1560 |
| agagcagaag | atcggatgca | tctggattaa | ccagagtcag | tcttgtcttg | gtgtgcactg | 1620 |
| cagcgacaag | gagcaggccg | tccctaccat | cgacgctgac | gaagcgcacg | cgctgctgag | 1680 |
| ctccggccat | ggctacgtgg | atgtcaggtg | cgtagagctc | agccagtcag | ggacgcgcct | 1740 |

```
atgcgtgtgc tggagcttcc agacgaactg acgctgacgg ggacgaggtg gttctccttc      1800
gtgcaggatg cggggggact tccacaaggc gcatgcgccc ggtgctcgga acgttcccta      1860
ctacctgtcc gtcacgccgc aaggtcagtt tcttgctcgc tggcgttggc gctggcactg      1920
gcattggggt tattgatttg agctgcctct gtccccgtgt agggaaggag aagaacccac      1980
actttgtaga ggaagtggct gccttctgtg ggaaggatga tgtcttcatt gtggtagcta      2040
ttcactcata taaataaata aataaatgta ctagtactct ataaatagat agatacgcct      2100
gtaatcaagg agttgtcgtg tagggttgca acacggggaa cagatccagg ttcgcgacgg      2160
cagaccttct gaacgcggta aacacagccc atccgagctt tagcatcaat ccagttagct      2220
gtatgtgtgt gtgtgtgtgt gtgtgtttaa ctgagggtca cactagtctg ctcgcat        2277
```

<210> SEQ ID NO 22
<211> LENGTH: 897
<212> TYPE: DNA
<213> ORGANISM: maize

<400> SEQUENCE: 22

```
aagatagctg caaaacaagc gagttactta caaccaaaca gaagggtaga aaccacctga       60
agccatgtgc attgctgcat ggatttggca ggctcaccct gtgcaccaac tcctcctgct      120
tctcaacaga gatgagttcc acagcaggcc tacaaaagca gtaggatggt ggggtgaagg      180
ctcaaagaag atccttggtg cagggatgt gcttggtgga ggaacatgga tggggtgcac       240
caaggatgga aggcttgcct tcctgaccaa tgtgcttgaa ccagatgcca tgcccggtgc      300
acggactagg ggagatctgc ctctcaaatt cctgcagagc aacaagagcc cactcgaagt      360
tgcaactgaa gtggcagaag aagctgatga atacaatggc ttcaacctca tactagctga      420
tctaacaaca aatatcatgg tttatgtgtc aaaccggcct aagggtcagc ctgcaacaat      480
tcaactcgtg tcaccaggac tccatgtgct gtccaatgca aggctagata gcccttggca      540
gaaggcaatt ctcctcggta aaaacttcag ggagcttctt agggagcatg gtgctgatga      600
ggttgaagtg aaggatatag ttgagaggct aatgactgac accacaaagg ctgacaaaga      660
tagactgcca aacactggtt gtgatcccaa ctgggagcat ggtctgagct ccatcttcat      720
tgaggtgcaa actgaccaag ggccctatgg gacacggagc acagccgttt tatcagtgaa      780
ctatgatggc gaagctagct tgtacgagaa gtatcttgag agtggtatat ggaaggatca      840
cacagtgagt taccagatag agtagtaggc attgcacagg aaaagttggc gacctca         897
```

<210> SEQ ID NO 23
<211> LENGTH: 266
<212> TYPE: PRT
<213> ORGANISM: maize

<400> SEQUENCE: 23

```
Met Cys Ile Ala Ala Trp Ile Trp Gln Ala His Pro Val His Gln Leu
 1               5                  10                  15

Leu Leu Leu Leu Asn Arg Asp Glu Phe His Ser Arg Pro Thr Lys Ala
            20                  25                  30

Val Gly Trp Trp Gly Glu Gly Ser Lys Lys Ile Leu Gly Gly Arg Asp
        35                  40                  45

Val Leu Gly Gly Gly Thr Trp Met Gly Cys Thr Lys Asp Gly Arg Leu
    50                  55                  60

Ala Phe Leu Thr Asn Val Leu Glu Pro Asp Ala Met Pro Gly Ala Arg
65                  70                  75                  80
```

```
Thr Arg Gly Asp Leu Pro Leu Lys Phe Leu Gln Ser Asn Lys Ser Pro
                85                  90                  95

Leu Glu Val Ala Thr Glu Val Ala Glu Ala Asp Glu Tyr Asn Gly
            100                 105                 110

Phe Asn Leu Ile Leu Ala Asp Leu Thr Thr Asn Ile Met Val Tyr Val
                115                 120                 125

Ser Asn Arg Pro Lys Gly Gln Pro Ala Thr Ile Gln Leu Val Ser Pro
            130                 135                 140

Gly Leu His Val Leu Ser Asn Ala Arg Leu Asp Ser Pro Trp Gln Lys
145                 150                 155                 160

Ala Ile Leu Leu Gly Lys Asn Phe Arg Glu Leu Leu Arg Glu His Gly
                165                 170                 175

Ala Asp Glu Val Glu Val Lys Asp Ile Val Glu Arg Leu Met Thr Asp
            180                 185                 190

Thr Thr Lys Ala Asp Lys Asp Arg Leu Pro Asn Thr Gly Cys Asp Pro
        195                 200                 205

Asn Trp Glu His Gly Leu Ser Ser Ile Phe Ile Glu Val Gln Thr Asp
    210                 215                 220

Gln Gly Pro Tyr Gly Thr Arg Ser Thr Ala Val Leu Ser Val Asn Tyr
225                 230                 235                 240

Asp Gly Glu Ala Ser Leu Tyr Glu Lys Tyr Leu Glu Ser Gly Ile Trp
                245                 250                 255

Lys Asp His Thr Val Ser Tyr Gln Ile Glu
                260                 265

<210> SEQ ID NO 24
<211> LENGTH: 1351
<212> TYPE: DNA
<213> ORGANISM: maize

<400> SEQUENCE: 24
cgactggagc acgaggacac tgacatggac tgaaggagta gaaaatcagc cgcagtcgcg     60
tcgcgtcgcg tcgcgtccag tccaatcctc ggagcctcac acgggcggac gagcgggagc    120
ttctcccaat ctccctgcc ctgccctgcc ctgccgccgc gcttagcttc gcatcttccc    180
ctcctcctcc tcctccttcc tcggccaagc gaggagcgag gcgcgggcgc gagcgcgtcg    240
ttgagatgga ttcggaggcg gtgcagcacg gccttctccc tctgtctgcc tgtcctccta    300
ccgccaacag ctgcgcgcat acagccgtg ggtgcagcgt cgtggcgccc tgctgcggcc    360
aggccttcgg ctgccgccat tgccacaacg acgccaagaa ctcgctggag gtcgaccccg    420 cgaccggca cgagatcccc cgccacgaaa taagaaggt gatctgttct ctctgctcca    480
aggaacagga cgtgcaacag aactgctcca gctgtgggc ctgcatgggc aagtacttct    540
gtaaagtatg caagttcttc gatgatgatg cctcaaaggg ccagtaccac tgtgacggat    600
gtggaatatg tagaaccggc ggcgtggaga acttttttcca ctgtgataaa tgtgggtgtt    660
gctacagcaa tgtcttgaag gattccacc actgcgtcga aagagcaatg catcacaact    720
gccccgtctg ctttgagtat ctgttcgact ccacgaagga catcagcgtg ctgcaatgtg    780
ggcataccat ccatttggag tgcatgaacg agatgagagc acaccatcac ttctcatgcc    840
cagtgtgctc gaggtccgcc tgcgacatgt cggccacatg gcggaagctc gacgaggagg    900
tcgcggccac gccgatgcct gacatctacc agaagcacat ggtgtggatc ctgtgcaacg    960
actgcagcgc gacctcgagc gtgcggttcc acgtgctggg gcacaagtgc cccgcgtgca   1020
```

```
gctcgtacaa cacccgggag acgagggctg cgtgccccag gatctgaggc gaaccagagg    1080
ccatgtcaca aaatgccagg gagatgccgt ccaacgacca tctgtctgca ggacgttgct    1140
gcgcttaagg ttaaaggcta cgcgagacc  aggcctggta gtccagtctt gagtttggtg    1200
ctggagcatt tgtaatgttc cggtaaaatg taatgcgtcc atgagtgctg tccaggcagt    1260
aagcacacct gtggatcggg gccggcgcaa ggtccctagg caagctgcag gattagtggg    1320
gctattcatg tttagggcgc gaatgcaacg a                                    1351
```

<210> SEQ ID NO 25
<211> LENGTH: 273
<212> TYPE: PRT
<213> ORGANISM: maize

<400> SEQUENCE: 25

```
Met Asp Ser Glu Ala Val Gln His Gly Leu Leu Pro Leu Ser Ala Cys
1               5                   10                  15

Pro Pro Thr Ala Asn Ser Cys Ala His Tyr Ser Arg Gly Cys Ser Val
            20                  25                  30

Val Ala Pro Cys Cys Gly Gln Ala Phe Gly Cys Arg His Cys His Asn
        35                  40                  45

Asp Ala Lys Asn Ser Leu Glu Val Asp Pro Arg Asp Arg His Glu Ile
    50                  55                  60

Pro Arg His Glu Ile Lys Lys Val Ile Cys Ser Leu Cys Ser Lys Glu
65                  70                  75                  80

Gln Asp Val Gln Gln Asn Cys Ser Ser Cys Gly Ala Cys Met Gly Lys
                85                  90                  95

Tyr Phe Cys Lys Val Cys Lys Phe Phe Asp Asp Ala Ser Lys Gly
            100                 105                 110

Gln Tyr His Cys Asp Gly Cys Gly Ile Cys Arg Thr Gly Gly Val Glu
        115                 120                 125

Asn Phe Phe His Cys Asp Lys Cys Gly Cys Cys Tyr Ser Asn Val Leu
    130                 135                 140

Lys Asp Ser His His Cys Val Glu Arg Ala Met His His Asn Cys Pro
145                 150                 155                 160

Val Cys Phe Glu Tyr Leu Phe Asp Ser Thr Lys Asp Ile Ser Val Leu
                165                 170                 175

Gln Cys Gly His Thr Ile His Leu Glu Cys Met Asn Glu Met Arg Ala
            180                 185                 190

His His His Phe Ser Cys Pro Val Cys Ser Arg Ser Ala Cys Asp Met
        195                 200                 205

Ser Ala Thr Trp Arg Lys Leu Asp Glu Glu Val Ala Ala Thr Pro Met
    210                 215                 220

Pro Asp Ile Tyr Gln Lys His Met Val Trp Ile Leu Cys Asn Asp Cys
225                 230                 235                 240

Ser Ala Thr Ser Ser Val Arg Phe His Val Leu Gly His Lys Cys Pro
                245                 250                 255

Ala Cys Ser Ser Tyr Asn Thr Arg Glu Thr Arg Ala Ala Cys Pro Arg
            260                 265                 270

Ile
```

<210> SEQ ID NO 26
<211> LENGTH: 7106
<212> TYPE: DNA
<213> ORGANISM: maize

<400> SEQUENCE: 26

```
ccttacaggt tatcacttac cgcctccgtt ttcgaatatt tatcgttcgc tagttaatct      60
taatttaaac ttaaatgagg caaataaacg tttaaactat tctcttgatc gtgtgtctga     120
ttgtcttgtt gtttaaaatg cctcctagat cgatcgtcgt agtgcaggtt gttttagaca     180
aagttgaact gcgatcagac cgagaccgga caaccattga gcagttattt tcctattcat     240
cgtggactaa ctggaagata ttttctgagc tccaaaaaat atccaaagga agggagaacg     300
tgaaggacga ggtcggaccg gacacgcctc ccctcgctaa tcattgaggc ggaggcggcg     360
gaggcgattt tgggaacact cgcaggtaga ttttgcgtga acttggacga gggtcatttt     420
cgctttggat gaatccacga ggtggtgtca ctgcacgcgc acggggccct caaaccgttt     480
gaaaaccaaa ccgaaggcaa caaaacgaga ctctcatctc atctgactct acggccagct     540
caagtgatct gctgctggtg gccgacctgg cggcgtgatc tcgctcccgt gcccgtctcc     600
tccatccgac gcgtacatgg cccgccatcc tcatccatcc gccctccaga ggaccagtcc     660
agaccaataa taaagggaa ggtcgacgac gggctcgctc caatccggcg aaccgcgtcc     720
ccgtcagcct gtcatcccgt gggcgcgcgg ctgtcgacct gcgcatcagc ttctatgatt     780
agccaggagc aataatttat tactcctatt tgccaggcga cgttcgtcca attcgacccg     840
gcaggcagca ggcagcagct gtgctcctgt gggtgggtgg gtcatgggtg accacatgca     900
tcgatggagc cagggccgcc gtgtgcgcag ccaactctac ctatcccgc ccccgggatg     960
ggcgatggca actatcctat cgcaacaata tcctggggtg ggggctataa acggagcgg    1020
cccgcgtggg gcgcgcctcc atcagccgca gtcgcgtcgc gtcgcgtcgc gtccagtcca    1080
atcctcggag cctcacacgg gcggacgagc gggagcttct cccaatctcc cctgccctgc    1140
cctgccctgc cgccgcgctt agcttcgcat cttcccctcc tcctcctcct ccttcctcgg    1200
ccaagcgagg agcgaggcgc gggcgcgagc gcgtcgttga gatggattcg gaggcggtgc    1260
agcacgggta agcaagcaaa gcaatccatg gatcgatcca ggacacaggg aggagctagg    1320
aagaggaaca atctcatgat ctcattcatc tgacacagcc ttctccctct gtctgcctgt    1380
cctcctaccg ccaacagctg cgcgcattac agccgtgggt gcagcgtcgt ggcgccctgc    1440
tgcggccagg ccttcggctg ccgccattgc cacaacgacg ccaaggttcg gtggtttccc    1500
tccttccgtt ttcgcttcgg ctccggttca gcagatgttc tgaaacaacc ctgtcccgtg    1560
ccccggcaga actcgctgga ggtcgacccg cgcgaccggc acgagatccc ccgccacgaa    1620
ataaagaagg tcagcgttcc ctccctctgc tcaaagagca atctcctgcc tgtttcaacc    1680
attgcctatc tcgtgttcgt cttttgttatt accgtgagca aagaaaggaa gaaacaaaca    1740
agagcgccgc cttctctctt ctccttctcc atgtaatgga gcatttgttc cgccgcgtag    1800
tcgagtgcaa gcagcggttt tcctcttttg gaaacccacc cccacgcacg gttccgttcc    1860
aatctcgccc ttccaattga ccaacacaaa cctttcctaa gatttcttgt cctccttacc    1920
cttctacaga caagtacgaa acgcaatcgc acaaggttat actactacta gcttttagtg    1980
ttctagcgac cttagatttt tttttttggt taggcatccc tgattttct cacacttaaa    2040
agcttcttca gataaggcca tatcagctca gctcagtgct ctgggagccg ttctgcactt    2100
cacttgcgtg tcactaaaaa cttgactgct ttccgcgatg tgctccgcac caagtggccg    2160
gcactgcgtg gtccacagga ttttcaaga gaaagccggg gtcacgggtg ccacttgaag    2220
ccaaggacag gcgtctggga ttggagaata tatgagaaag ggataccgtc agaggcacat    2280
ctcaccgtca aactgaacag ggtctaactg cttccagctg atttgattga gtttgagtgc    2340
```

```
tgcatagttg aggacctgga tatagtgacg tgtcctgaca ggtgtctttg gacctattag    2400
cagtgaatct gacgtcgatc ggctaaagca atcatgttcg attcttatcc tttttttttt    2460
gagagtatat gcctgattcg ataaacgttc ctatcctgtt tcctgatgat gcatatatgt    2520
tgtttcgatt catatagaat cataccatcc atctattttg tttaaaaaaa aaatttctgg    2580
gtggccatgg gcacagcatg cctgttctta agataacgat tccagtaact gttcccttct    2640
gtcactgaac tcatatgaat cgagacttaa ctggagctgt tgcgcaggtg atctgttctc    2700
tctgctccaa ggaacaggac gtaagttgtc taccaaaacg tactcctaca acagtttttc    2760
aggagcacgc atcttttggc tgtactacta ctgctaactg catggaaact gctcattccc    2820
atcggcaggt gcaacagaac tgctccagct gtggggcctg catgggcaag tacttctgta    2880
aagtatgcaa gttcttcgat gatgatgtaa gcgtactcga atcccagacg atgaacaaag    2940
aaactgaact cgatgcgttg tttactgcgt ttctttttc cccttcttc ttcacgtaca      3000 tactgtactg ctcttggtcc aggtctcaaa gggccagtac cactgtgacg gatgtggaat    3060
atgtaggtaa gcaccaccac gctgatggct acgtctaaag acttgacgcg cagaagtgta    3120
aaacttctgt cagccgttca aaactgataa attcggttc ctcgtcttct tgttgtttat     3180
gcagaaccgg cggcgtggag aacttttcc actgtgataa atgtggtgag tttctgcgcg     3240
gacttctttc tgctaagatt ctgtaaccat gctatgcagc aaagatttca ctcgcgccct    3300
tattggtgtc cttgttgccg tccgacaggg tgttgctaca gcaatgtctt gaaggattcc    3360
caccactgcg tcgaaagagc aatgcatcac aactgccccg tctgctttga ggtgagagac    3420
ctccgtttca acggaacatt cactctgaat gttccaatct cttgatattg agaaggtttc    3480
cctctgtttt ttttcacagt atctgttcga ctccacgaag gacatcagcg tgctgcaatg    3540
tgggcatacc atccatttgg agtgcatgaa cgagatgaga gcacaccatc agtaagcata    3600
tataccgttc tcttcggagc tgagaaacgg tgccacctca caacatcctc ttttagtcgc    3660 agtgaccta cagtctcagc cctgtttggt ctttggcagc ttctcatgcc cagtgtgctc     3720
gaggtccgcc tgcgacatgt cggccacatg gcggaagctc gacgaggagg tcgcggccac    3780
gccgatgcct gacatctacc agaagcacat ggtaagaagc cgaccgccca ctcgttcgtc    3840
gtcccgttac atcttttcca cagccatggc tcgctgtttg acgagctctg aacctgtccg    3900
gggtgccgat tgctggaact gaacggcaaa tgaacgctgt ggtgtgagtg caggtgtgga    3960
tcctgtgcaa cgactgcagc gcgacctcga gcgtgcggtt ccacgtgctg gggcacaagt    4020
gccccgcgtg cagctcgtac aacacccggg agacgagggc tgcgtgcccc aggatctgag    4080
gcgaaccaga ggccatgtca caaaatgcca gggagatgcc gtccaacgat catctgtctg    4140
caggacgttg ctgcgcttaa ggttaaaggc tagcgcgaga ccaggcctgg tagtccagtc    4200
ttgagtttgg tgctggagca tttgtaatgt tccggtaaaa tgtaatgcgt ccatgagtgc    4260
tgtccaggca gtaagcacac ctgtggatcg gggccggcgc aaggtcccta ggcaagctgc    4320
aggattagtg gggctattca tgtttagggc gcgaatgcaa cgaaattacc cgtgggccgt    4380
gggctcggta tgtaacagaa ccgattattt ctattacaat aataacatgc agttctattg    4440
ggccgagcct aatcaggcac cacgaatgtg aataattgca catggcgcat atatggcggg    4500
cagtagatac atataaaatg gagaaaatcc gtttattgcc atcaaaactt atactgatca    4560
ctacaatacc atctaaaatg atgtgctccc ttcaaaacca ttggtttata ttttctatcc    4620
tttcattgcc attgccgtta cataatggcg catgtggcat atatgggcgg cgtatgtagg    4680
```

```
ttcaggatgg tcacacgaca tatgacgaga ctacagagac atggtcaaga gaagttcagt    4740
ggattgtgac attctgatct aagacttctt aaaattggag ttaataagat cgataatact    4800
cgtaccaata atgcacatct tgcttttag aagcctgttt tgaaataacc ccaggattaa     4860
gcatgtttgg cccaaagaaa tttttgtgat ggtggtcgac cgagaagttt tcttgactgc    4920
atgccagtga ggacaaaaaa acacatatga aagaatcgtg ttggtctgtg agaatagatc    4980
aggaagtttt ctcgactgcg cgaccatgga tggttgggt gtttcatcaa ggatccgctt     5040
taaacacata cctttttgcc ttggtgatgg ataaggacat accggacata aagggataa     5100 cccttggtgt gtgttttttt gcagacaatg taatgctagt tgatgaaagt cgggcatgag    5160
taaatggaaa actagagttg tggcaagaaa ctttataatc aaaaggtttt agacttagta    5220
gaactaaaat agaatatatt ggatgcgatt tcagcactac atgaggaa tgagatctta      5280 gtttagaagg tctaggaagg acacctttag atatttagta tcagcctata gagagaccgg    5340
gatattaatg aagatgctag ccataaaatc aaagtagagt cagtgaagtg gagtcaagca    5400
tctggcattt tatatgacaa agtgggaatt gcaaaagcta aaagaaagt tttaggacaa     5460 cgattagacc ttctatatta tatggaacat aattttagcc tacaaaaaga tgatatgttt    5520
agcagataaa tgttgcggta atacatatgt tacgttggat ttgtgaacat acaaaaaggg    5580
atcgagttta gaatgatgat atacatgata gactaggggt agcaccagtc gatcgatatg    5640
gtttgaatat atccaacgga gacctataga ggtgtcaata tgtcttagga cctgtttgaa    5700
agcatccagt ttttaagaaa ttggtttata gaaattaaag tggttccaaa catacaagtt    5760
tatgccccag tttatataaa ctggattatc aatttcttaa aaaccaagaa gctagtcttt    5820
gctagctaaa accaactttt gcttgtttaa ttacataatg cccttgttgg ttgcatggaa    5880 tttacatctca ttgtcgtcgc ttttaagata gaggaaggt atgttagtaa ttgtgtatca    5940
aaaaatagaa aatttgtttc ttagaactaa gttccaaaca ccctcaccta acttttttat    6000
aaactagttt ctataaactg gagatagaaa ttggttttta ataaaccggt atgctttcaa    6060 acaataccctt aggattctaa gatgtgatac caatgagaaa aggaagagga agactgaagt    6120 tggtatgggga ggtgataata aaatgagtct tgaaaaaatg agatatatct aaagatttag    6180
ccttgaatag aaatgcatga aaataactat ccatatgttt gaaccttgac tttgagtttt    6240
gttgaatttt taactctagc ctacgccaat ttgtttggga ctaaaaggtt atgttgttgt    6300
tattgccgct ataaatggtg ttcaacactt tcttcaagat tatgatattt tgttttctac    6360
accaacaata ttactgttgg ggtctccttc tctgccgaag gtcctcagga tgaagaaact    6420
gtctttggtt catcttggta agatacgtca aaaggaccga atgccgaagc tgtgacagac    6480
atgcagggaa tatagcagag cttcgataag agttaaagct tcggcttaag atgattatga    6540
aggtcataca agaaaccaag ccaccaatga aaagacctgt ttatccttaa aatttgtatt    6600
agaacaatgt atagatatca gggtcataaa tgtacttttg cttgggcggc gtcccgtgcc    6660
tataaataga tgaactgtac ccccgtactg ttgacacttt cattgaaagt cattctcgca    6720
ctctctcctt caagcaagac gaaggtacta atgtaatata atgtttgtaa tggttcatta    6780
gaatgttatc caaactatgt cattactttg atatagaaaa taagtgaat tcataagata    6840 ataccacatt gtgatattat ctccatgaga aatgaagatc cgctcttctt cacttcgcc    6900 caaaaaccat tatctttgag agaagataat tgaaggaaa ttgggttaac catttcctat    6960
aactaatttt ggtgggtgat gatcaacaca aacccatgga ctaactagtt tgtctagaat    7020
tcatggatta caggtgcata aggttcaaca caaaccaaga aagaaatccg gttagggaca    7080
```

```
caattaaaaa tggagcaaag acttga                                          7106
```

<210> SEQ ID NO 27
<211> LENGTH: 645
<212> TYPE: DNA
<213> ORGANISM: maize

<400> SEQUENCE: 27

```
cgactggagc acgaggacac tgacatggac tgaaggagta gaaagctgct attttcttct     60
tacattgtcc actgcgctag ctagctcgca tctacctgga aagctgaaag ctagccagag    120
cgctagctag cttcgttcct cgtcgccgcg cgccggccag atgactgctc accagacttg    180
ctgcgatgat gccgttgccg ccggcactgc accggctgcc aggaggaggc gcctcaaatt    240
gacgaggccg tcggcctcgc tcttgatggc gaggaagcta aggaagaagg ctgccggcag    300
caaacgccca agggcggcag cgtcgaggaa gcgcgcgatg gcgatcagga ggaagatgga    360
agcgctgagg ctgctcgtgc cactctgcgg ccgagacaac ggctcggtga ccggtggggc    420
ggtcgaacga ctggacgagc tcctcatgca cgccgccggg tacatcctgc gcctccagat    480
gcaggtcaga gtgatgcagc ttatggtcca tgcactaaat gaccggcccg aggattaatc    540
ttcttcccaa gaccatgtga tcttccttct ttaatttctt cttcatcttc ttcgcgtgcc    600
tgtgttgcac gaggcagctg tgcgtcggtg tctgggtgca aatca                    645
```

<210> SEQ ID NO 28
<211> LENGTH: 125
<212> TYPE: PRT
<213> ORGANISM: maize

<400> SEQUENCE: 28

```
Met Thr Ala His Gln Thr Cys Cys Asp Asp Ala Val Ala Ala Gly Thr
 1               5                  10                  15

Ala Pro Ala Ala Arg Arg Arg Arg Leu Lys Leu Thr Arg Pro Ser Ala
            20                  25                  30

Ser Leu Leu Met Ala Arg Lys Leu Arg Lys Lys Ala Ala Gly Ser Lys
        35                  40                  45

Arg Pro Arg Ala Ala Ala Ser Arg Lys Arg Ala Met Ala Ile Arg Arg
    50                  55                  60

Lys Met Glu Ala Leu Arg Leu Leu Val Pro Leu Cys Gly Arg Asp Asn
65                  70                  75                  80

Gly Ser Val Thr Gly Gly Ala Val Glu Arg Leu Asp Glu Leu Leu Met
                85                  90                  95

His Ala Ala Gly Tyr Ile Leu Arg Leu Gln Met Gln Val Arg Val Met
            100                 105                 110

Gln Leu Met Val His Ala Leu Asn Asp Arg Pro Glu Asp
        115                 120                 125
```

<210> SEQ ID NO 29
<211> LENGTH: 2433
<212> TYPE: DNA
<213> ORGANISM: maize

<400> SEQUENCE: 29

```
taaatctgac ctccaaaatg tctctaatga agtgtctgc gagaaacagt attgctcgac      60
cgaggaagaa aggtatttat aacacaccca tcacaaatgg ttggcttaat taaccgcaag    120
tgcagaatag atttgcactg ttggttcact taataaaact gcaagtgaaa atatactttt    180
```

```
tctactatcg gttttgttaa gtgaacctac cgattttgca ctggtgatta tttaagccaa      240
cctcatgtga taatatgaat gatttgcacg tggttttatt aagcgaacta acaatgtaaa      300
tgtgttttcca atggtggttt ttaagtcggg accgtcattt tactttaact ggcgcgcacc     360
gtgctgtttt atacttgact gatgaacctt cgtggtgagt ggaagcggtg tggagcgagg      420
gctagctcat gcggccagcc ggcgacattt ctcttgttcc gatccccggg ccggccaacc      480
actcaattaa gtaggtgatc gattggcatg catgcatgga tgcatatcag caaatgcata     540
tcatatgcct cgctagctgg ctagtatata tagtggatgt ggatcggatc atgtgacggc      600
cgggcggtgg ctgcattgca ttggccctgc atatatgcac ggtgacacaa caacggggcc     660
caaataaagg acacgtcgaa ggtgcgcgcc ccagtggcgt ccgacagcgc gttttgacga     720
ggaaaagagg gtgcgggcac gcgcgcacgc atatgctcgc ggcatgcagc ctcagtggcc      780
gatgacgagt ggcgtgtggt gtggccggcg gccggccggc cgggtgcctg cgtggtgcat     840
gttgcttgcc atgcctgcgt gaaatgagcc gtcagcgagc gagctgaggg cgggcatgtg     900
gctgcatgtg gccactagtt tggagaacat gcggcatatg ccccgaccct tcctgggcgc     960
tcaagcaaac accgctctcg tgctcgctct cttgggaaat cgcagatgca tgctacccaa     1020
cgtgacctga atctctttta cgtacgcaca ccctagcgtg ctgctctcct gtgtccccgc     1080
ctcctgctag ctgttcacaa tatccacgcg atttaacaaa cagatatgtg tgcatgctac    1140
tgcttgtttt cctattcaat atagtaatct gctttattta gagtaccgta cctgtgccgt    1200
cagtgccccc aaccccaacg taactacgca cgcacatggc atctaatcta tataagcatc   1260
agaccttgct cccttaatct cgcgctgcta ttttcttctt acattgtcca ctgcgctagc    1320
tagctcgcat ctacctggaa agctgaaagc tagccagagc gctagctagc ttcgttcctc   1380
gtcgccgcgc gccggccaga tgactgctca ccagacttgc tgcgatgatg ccgttgccgc   1440
cggcactgca ccggctgcca ggaggaggcg cctcaaattg acgaggccgt cggcctcgct   1500
cttgatggca aggaagctaa ggaagaaggc tgccggcagc aaacgcccaa gggcggcagc   1560
gtcgaggaag cgcgcgatgg cgatcaggag gaagatggaa gcgctgaggc tgctcgtgcc   1620
actctgcggc cgagacaacg gctcggtgac cggtggggcg gtcgaacgac tggacgagct   1680
cctcatgcac gccgccgggt acatcctgcg cctccagatg caggtcagag tgatgcagct   1740
tatggtccat gcactaaatg accggcccga ggattaatct tcttcccaag accatgtgat   1800
cttccttctt taatttcttc ttcatcttct tcgcgtgcct gtgttgcacg aggcagctgt    1860
gcgtcggtgt ctgggtgcaa atcattggct gagtgtgtta ttggtgatat tatttgttcg     1920
tatatacaga atatatactc atgcatgcat actgtatgag atgatagagt aaatctagac    1980
atatatagtt caaggaaacc tacagccaac agttgtatgc atgtgagggg ggttccttgt    2040
ctgtatgtac gcaattgtct attgtgtgac ggttgaaatt gaaatttcgt caatcatcat    2100
ttcttcgtct agataacgtg tgtacaaacg gcgagtgttt aaatgaacta gagctaataa   2160
ttagtggcta aaattagctg gagacatcca aacaccctaa ctaataattt aactattagt   2220
tatttttagt aaattagtca atacttagct agctatttgt tagctagcta attctactag   2280
cattttttag ctaactagct attagctcta gtacattcaa acacccttt agggactaat    2340
ttttagtctc tccattttat ttcattttag tcactaaatt accaaatacg aaaattaaag   2400
ctctatttta gtttccggta tttgacaatt tag                                 2433
```

<210> SEQ ID NO 30
<211> LENGTH: 1146

<212> TYPE: DNA
<213> ORGANISM: maize

<400> SEQUENCE: 30

```
ggacactgac atggactgaa ggagtagaaa atccatccat tccctcgcc aagccgccac     60
ggcctgactt tccctcccgc acaccgcga ccatacaggc aagtcaggca tacaccaaca    120
acgctcgtcg tgcacctcgc gcctcaggtc accccaccaa attcctcttg atacgccgaa   180
tttcttttgc taattctgct acctcctgtc gctaagccac catattcagt ctaacccctg   240
ctctgagctc acctgattgg cggctccgtt cggcctctgg gcctgggtgt accgactacc   300
gagggctctt tcgaaatgtc aattgggtcg agtttggtgg gctacgtgaa gcatggatga   360
atttcccggc tggaagcggg aggcggcagc agcatccggg gccggagcac ctgtcgccga   420
tgacgccgct cccgctggcg cggtagggt cggtctactc gctcacgttc gacgagttcc    480
agagctcgct cggtggggcc accaaggact tcggatccat gaacatggac gagctcctcc   540
gcaacatctg gtcggcggag gagacacaca gcgtcacagc tgcggaccat gccgcgcggg   600
cgccgtacgt ccagtgccag ggctcgctca ccctcccctg cacgctcagc cagaagaccg   660
tcgacgaggt ctagcgtgac ctcgtgtgca acggtggagg accctccgac gaggctgtgg   720
cgccgcccca ccggcccaac ggcagccgac gctcggggag atcatgctgg aggagttcct   780
cgtccgcgcc ggcgtggtga gggaggacat gatggcggcg gcgcccgtac caccagcgcc   840
gggttgccca ccacctcatc tgcaaccgcc aatgctgttt ccacatggca atgtgtttgc   900
tcccttagtg cctccgctcc aattcgggaa tgggtttgtg tcgggggctc tcagtcagca   960
gcagggaggt gttcttgagg ccccggcggt atcgccgcgg ccggtgacgg caagcgggtt  1020
cgggaagatg gaaggagacg acttgtcgca tctgtcgcca tcaccggtgt cgtacgtttt  1080
tttgtgctgg tttgagggga aggaagccac cagctgtgga caaggtggtt gagaggaggc  1140
aacgcc                                                             1146
```

<210> SEQ ID NO 31
<211> LENGTH: 108
<212> TYPE: PRT
<213> ORGANISM: maize

<400> SEQUENCE: 31

```
Met Asp Glu Phe Pro Gly Trp Lys Arg Glu Ala Ala Ala Ser Gly
1               5                   10                  15

Ala Gly Ala Pro Val Ala Asp Asp Ala Ala Pro Ala Gly Ala Val Gly
            20                  25                  30

Val Gly Leu Leu Ala His Val Arg Arg Val Pro Glu Leu Ala Arg Trp
        35                  40                  45

Gly His Gln Gly Leu Arg Ile His Glu His Gly Arg Ala Pro Pro Gln
    50                  55                  60

His Leu Val Gly Gly Gly Asp Thr Gln Arg His Ser Cys Gly Pro Cys
65                  70                  75                  80

Arg Ala Gly Ala Val Arg Pro Val Pro Gly Leu Ala His Pro Leu
                85                  90                  95

His Ala Gln Pro Glu Asp Arg Arg Gly Leu Ala
            100                 105
```

<210> SEQ ID NO 32
<211> LENGTH: 122
<212> TYPE: PRT
<213> ORGANISM: maize

<400> SEQUENCE: 32

| Met | Leu | Glu | Glu | Phe | Leu | Val | Arg | Ala | Gly | Val | Val | Arg | Glu | Asp | Met |
| 1 | | | | 5 | | | | | 10 | | | | | 15 | |

| Met | Ala | Ala | Ala | Pro | Val | Pro | Pro | Ala | Pro | Gly | Cys | Pro | Pro | Pro | His |
| | | | 20 | | | | | 25 | | | | | 30 | | |

| Leu | Gln | Pro | Pro | Met | Leu | Phe | Pro | His | Gly | Asn | Val | Phe | Ala | Pro | Leu |
| | | | 35 | | | | | 40 | | | | | 45 | | |

| Val | Pro | Pro | Leu | Gln | Phe | Gly | Asn | Gly | Phe | Val | Ser | Gly | Ala | Leu | Ser |
| | | | 50 | | | | | 55 | | | | | 60 | | |

| Gln | Gln | Gln | Gly | Gly | Val | Leu | Glu | Ala | Pro | Ala | Val | Ser | Pro | Arg | Pro |
| 65 | | | | | 70 | | | | | 75 | | | | | 80 |

| Val | Thr | Ala | Ser | Gly | Phe | Gly | Lys | Met | Glu | Gly | Asp | Asp | Leu | Ser | His |
| | | | | 85 | | | | | 90 | | | | | 95 | |

| Leu | Ser | Pro | Ser | Pro | Val | Ser | Tyr | Val | Phe | Leu | Cys | Trp | Phe | Glu | Gly |
| | | | | 100 | | | | | 105 | | | | | 110 | |

| Lys | Glu | Ala | Thr | Ser | Cys | Gly | Gln | Gly | Gly |
| | | | | 115 | | | | | 120 |

<210> SEQ ID NO 33
<211> LENGTH: 1376
<212> TYPE: DNA
<213> ORGANISM: maize

<400> SEQUENCE: 33

```
tagaatagcc agcatcgaca aattacttac aaatagaaac attacctgtt tcctcccacg      60
cgacctcgcg gccaactccc ggttcttgat catccggcgt tgcctcctct caaccacctt     120
ctccacagct ggtggcttcc ttcccctcaa accagcacaa aaaacgtac gacaccggtg      180
atggcgacag atgcgacaag tcgtctcctt ccatcttccc gaacccgctt gccgtcaccg     240
gccgcggcga taccgccggg gcctcaagaa caccctcctg ctgctgactg agagcccccg     300
acacaaaccc attcccgaat ggagcggag gcactaaggg agcaaacaca ttgccatgtg      360
gaaacagcat tggcggttgc agatgaggtg gtgggcaacc cggcgctggt ggtacgggcg     420
ccgccgccat catgtcctcc ctcaccacgc cggcgcggac gaggaactcc tccagcatga     480
tctcccccgag cgtcggctgc cgttgggccg gtgggcggc gccacagcct cgtcggaggg     540
tcctccaccg ttgcacacga ggtcacgcta gacctcgtcg acggtcttct ggctgagcgt     600
gcagggagg gtgagcgagc cctggcactg gacgtacggc gccgcgcgg catggtccgc      660
agctgtgacg ctgtgtgtct cctccgccga ccagatgttg cggaggagct cgtccatgtt     720
catggatccg aagtccttgg tggccccacc gagcgagctc tggaactcgt cgaacgtgag     780
cgagtagacc gaccgctacc gcgccagcgg gagcggcgtc atcggcgaca ggtgctccgg     840
ccccggatgc tgctgccgcc tccgcttcc agccgggaaa ttcatccatg cttcacgtag     900
cccaccaaac tcgacccaat tgacatttcg aaagagccct cggtagtcgg tacacccagg     960
cccagaggcc gaacggagcc gccaatcagg tgagctcaga gcaggggtta gactgaatat    1020
ggtggcttag cgacaggagg tagcagaatt agcaaaagaa attcggcgta tcaagaggaa    1080
tttggtgggg tgacctgagg cgcgaggtgc acgacgagcg ttgttggtgt atgcctgact    1140
tgcctgtatg gtcgcgggtg tgcgggaggg aaagtcaggc cgtggcggct tggcgagggg    1200
aatggatgga tatgtgtcgc caccaaggag tcgtgtgggg gagtttaaaa cgtcgccagg    1260
ctcgaggtcg cacatggtgt tgggtttggg tgcgtgctgg gtcataaaag ctgaaaggga    1320
```
attaggctta cacctatttc ctaaatgatt ttggtggttg aattgtccaa cacaaa      1376

<210> SEQ ID NO 34
<211> LENGTH: 686
<212> TYPE: DNA
<213> ORGANISM: maize

<400> SEQUENCE: 34
attcccgtct tacctagcgc tagggttagt acgcgtccac ggcgacgacc tctgcgcgga     60
gtgtgctccg attggctggc ctcctcgatc ctccttcccg cgaacgcacg cgcgcgcgag    120
ggagaggttg agacttgaga gatagacgaa agacgaaaca agggaaggag acgccgtgct    180
cgcctattgg ccgccgcctc cgctccttcg cgcccaatgg cttctgcagc atatcaatat    240
catgcagcat agcagtactc agacccttac tacgcaggcg ttgttgctcc ctatggaagt    300
caagatgtgt gtccgaggag cctgtctatg tgaacgccaa gcagtaccgc ggcattctaa    360
gacggcggca gtcacgtgcc aaggccgagc ttgagagaaa gcgctggtca agcaagaaag    420
ccgtatcttc acgagtcccc gtcatcagca cgcgatgacg aggagggcga gagggaacgg    480
tggacgcttc ctaaacacga agaagagtga ccgtgtccct cctgatgact tgatacagct    540
acgacgcaca aacgaggctt gaagaggtag cggtctggct ggcatcctag agcagcggtt    600
tctgtccaca ggcacgtgca tctgagaccg gatccgtagc tccactccac agcatatgcg    660
cagcccatcc atctcgtgca cacttg                                          686

<210> SEQ ID NO 35
<211> LENGTH: 50
<212> TYPE: PRT
<213> ORGANISM: maize

<400> SEQUENCE: 35

Met Gln His Ser Ser Thr Gln Thr Leu Thr Thr Gln Ala Leu Leu Leu
1               5                   10                  15
Pro Met Glu Val Lys Met Cys Val Arg Gly Ala Cys Leu Cys Glu Arg
            20                  25                  30
Gln Ala Val Pro Arg His Ser Lys Thr Ala Ala Val Thr Cys Gln Gly
        35                  40                  45
Arg Ala
    50

<210> SEQ ID NO 36
<211> LENGTH: 922
<212> TYPE: DNA
<213> ORGANISM: maize

<400> SEQUENCE: 36
cgactggagc acgaggacac tgacatggac tgaaggagta gaaaaaaaac ccaaatcaaa     60
tttcgccttc gtcgtcgtct tatcgtctca gatttgactc catgtcggcg gcgctcgcgg    120
tgacggacga ggtggccctg ccgatccggg cggtggggga tctagcggcc gccgccgagg    180
tctcgcggga ggaggtcgcc gtcatcaccc agtgcgcggc gctcggtggg aagttgcctt    240
ttgaagatgc atcagttggt gcggttcttg cagtcattaa aaacgtggaa agcttgaggg    300
agcaattggt tgctgaaatc aggcgggtgc tgaaagctgg tggaagagta ttggtgcaga    360
gccctgcacc ctcatccagt cagaagccga acactgatat tgagcgcaag ttactgatgg    420
gtggatttgc tgaagtgcaa tcttctgctg caagctcgca ggatagcgtg caatctgtta    480
cagttaaggc aaagaaggct agctggagca tgggctcttc ttttccccctt aagaaaacaa    540

```
caaaagccct tcccaagatt caaattgacg acgactctga tctgattgat gaagacagtc    600
tcttgactga ggaggacctg aagaaaccac aacttccagt tgttggggac tgtgaggtgg    660

gggcagcaaa gaaagcatgc aagaactgta cttgtggcag ggctgaggcc gaggagaagg    720
ttgggaagct ggagctcact gcggagcaga tcaataaccc tcagtcagct tgtggcagtt    780
gtgggttggg tgatgccttc cgctgtggaa cctgtcccta cagaggtctt ccaccattca    840
agcctggcga gaaggtttcc ttgtctggca acttccttgc tgctgacata tgatggcatc    900
gccaacatcg gcaaaacaag ga                                              922
```

<210> SEQ ID NO 37
<211> LENGTH: 263
<212> TYPE: PRT
<213> ORGANISM: maize

<400> SEQUENCE: 37

```
Met Ser Ala Ala Leu Ala Val Thr Asp Glu Val Ala Leu Pro Ile Arg
1               5                   10                  15

Ala Val Gly Asp Leu Ala Ala Ala Ala Glu Val Ser Arg Glu Glu Val
            20                  25                  30

Ala Val Ile Thr Gln Cys Ala Ala Leu Gly Gly Lys Leu Pro Phe Glu
        35                  40                  45

Asp Ala Ser Val Gly Ala Val Leu Ala Val Ile Lys Asn Val Glu Ser
    50                  55                  60

Leu Arg Glu Gln Leu Val Ala Glu Ile Arg Arg Val Leu Lys Ala Gly
65                  70                  75                  80

Gly Arg Val Leu Val Gln Ser Pro Ala Pro Ser Ser Ser Gln Lys Pro
                85                  90                  95

Asn Thr Asp Ile Glu Arg Lys Leu Leu Met Gly Gly Phe Ala Glu Val
            100                 105                 110

Gln Ser Ser Ala Ala Ser Ser Gln Asp Ser Val Gln Ser Val Thr Val
        115                 120                 125

Lys Ala Lys Lys Ala Ser Trp Ser Met Gly Ser Ser Phe Pro Leu Lys
    130                 135                 140

Lys Thr Thr Lys Ala Leu Pro Lys Ile Gln Ile Asp Asp Asp Ser Asp
145                 150                 155                 160

Leu Ile Asp Glu Asp Ser Leu Leu Thr Glu Glu Asp Leu Lys Lys Pro
                165                 170                 175

Gln Leu Pro Val Val Gly Asp Cys Glu Val Gly Ala Ala Lys Lys Ala
            180                 185                 190

Cys Lys Asn Cys Thr Cys Gly Arg Ala Glu Ala Glu Glu Lys Val Gly
        195                 200                 205

Lys Leu Glu Leu Thr Ala Glu Gln Ile Asn Asn Pro Gln Ser Ala Cys
    210                 215                 220

Gly Ser Cys Gly Leu Gly Asp Ala Phe Arg Cys Gly Thr Cys Pro Tyr
225                 230                 235                 240

Arg Gly Leu Pro Pro Phe Lys Pro Gly Glu Lys Val Ser Leu Ser Gly
                245                 250                 255

Asn Phe Leu Ala Ala Asp Ile
            260
```

<210> SEQ ID NO 38
<211> LENGTH: 5083
<212> TYPE: DNA
<213> ORGANISM: maize

<400> SEQUENCE: 38

```
gctgtaccag ttgaggtact ccttgacgtc ctcgtacatg gtgggcgcca gcgggtgcca      60
gatgccggag tcgaggtaga gcacggggtc gtcgtacttg atgccggcgc ccctaagcac     120
cggcaagtag gatccggcga tcatcttgag gaagttctgg aggttgtccg ccgagccgcc     180
gagccagaac tggaggctga ggatgtacag ccaggcgtcc tgcgccttgt cggagggcag     240
gtacttgagc accttgggca gcgtgcgcac gagcttgagc atgctgtcgg cgaagttgct     300
ggagttggac ttgctgcgct tgaagagctg gaagaagggg ctcttggact gccccagctg     360
cgacatgctg aaggagccga gcttgttgag gcgcatgacc tcgggcatgg aggggaagac     420
aaggacggcg tccatgcggt cgcgctcctt ctcggccgcg gccttgacct tgagcgccag     480
ctcctcgacg aagatgaggg agccgatgaa gacgttgacg tcggcgaggt cggcgcggaa     540
ggtagcccac gacctcgaac gacgcggcgc ggcgcgggtc agcgttgagc tgctgcacgg     600
cggccgtgac ggacgactgg tactgcgcct ccagcacgac gtagacgacc ttgacccgag     660
gcaggccccg cgggtcggcc ggcaccacgc gccgcacctc gggcttggtc tgcgtgaaca     720
agccgttgcc gccggcgacc gcgcaccgga tggcgccggc gcgccgcggc tgctggcgac     780
ggctgctcag gaggaacgag tgcagcggca cgggcgccgc caggagctgc ttctgcgccg     840
cggcggcgaa tggggtggac actagcgacg acgacatggc gcctgctcac aggacggagc     900
cggcgggcgg agaaacgcgc gcctggacac tgacgcgacg ctcgagcgca gtaagtaaaa     960
aaaaatctac actagactac tagagtaagg cgcctgttct tggctcgtgg ctggacaatt    1020
gttcttggcg gccgccgtcc ctcggaaaca gagcagggaa aggagaagaa gcgagcaggg    1080
gagcgcggga ggcgggaaaa tgtataggtt gtccgtgtcc acgtccttcg tctcaattaa    1140
gaagaggcat ccaggctcac aaaatcaatc tgaaaacaca tgcactgatg cacacttgtg    1200
tttgtgtaga ggcgcttata tatcatccaa aagacaagtc actcacacgc aaattcgcat    1260
tggctaacag aagctatttg gaatgcagtt cagtcgacta acaacgtagg tacccccgtc    1320
tccttgtttt gccgatgttg gcgatgccat catatgtcag cagcaaggaa gttgccagac    1380
aaggaaacct gccaatcgga gaagcagcag cagtgaacgt tcaagatcca gagtacaatc    1440
gacagacata tttttgatctc ctcgagaatt ctatcagggg aggagacgag tagaactgtt    1500
ttaccttctc gccaggcttg aatggtgaaa gacctctgta gggacaggtt ccacagcgga    1560
aggcatcacc caacccacac tgcaaagaaa aatcaaggat catttacaga tatcaccaga    1620
cgtgataggt aacctagtcc gagtgaacgt atgaaatttc acgagggggc acaagtgcca    1680
cctgtaagca atacttacac tgccacaagc tgactgaggg ttattgatct gctccgcagt    1740
gagctccagc ttcccaacct tctcctcggc ctcagccctg ccacaagtac agttcttgca    1800
tgctttcttt gctgccccca cctcacagtc cccaactggt gaaaacatca gtgaaaacat    1860
cacttaactg tttaggatcc aaacctaaac tggctattgc ttacggagtt gaactaagtt    1920
gacgggtttt gttgctctac caactggaag ttgtggtttc ttcaggtcct cctcagtcaa    1980
gagactgtct tcatcaatca gatcagagtc gtcgtcaatt tgaatcttgg gaagggcttt    2040
tgttgttttc ttaagggaa aagaagagcc catgctccag ctagccttct ttgccttaac     2100
ctacaagtgg ttcaaattag cacaaaaact aaagcctgca cagcaaaact aacatactat    2160
aacacatgat cttagaccac tcactgtaac agattgcacg ctatcctgcg agcttgcagc    2220
agaagattgc acttcagcaa atccacccat cagtaacttg cgctcaatat cagtgttcgg    2280
```

```
ctaacggaga caatcataaa aaaattaaga actttaaatc gacattgcaa gagaaacgag    2340
acaacaaaga cagattctga taagttaata ccttctgact ggatgagggt gcagggctct    2400
gcaccaatac tcttccacca gctttcagca cccgcctgat ttcagcaacc aattgctccc    2460
tcaagctttc cacgttttta atgactgcaa gaaccgcacc aactgatgca tcttcaaaag    2520
gcaacttccc acctgatgca tggcagaaca atagtttggt cacggttttg tgataacaca    2580
cacacacaca cacacacaca cacacacaca cacacacaca cacacacggc atagcactag    2640
caaagcataa cacaaattaa aaatcgaaca ttattgttta atagaggctc ccaaaatcag    2700
gaatgctagc acttggctta ttcataaaca cacacatcca taatcaggaa gcatacatta    2760
ctgaaccatt aaatttaata ataaaaattc agatgttgaa tccatggctg aaattttctg    2820
ttccttttga agtataatc ctaactttca tctccggctg acctggtaat atcttctagc    2880 tcctttacc ttatatttt ttcagttgct tgagaaatag cggtaggaaa attgacacat    2940
gtcattcgta aatccatggg acttagagca actccaagag cttcctaaga aattgttccc    3000
caaaacatca tagggggc tgctgaaaaa aatccactaa gagcaactcc aaatgagtgc    3060
tagaaaattt ccccaaaaaa tgattattgg ggatatgtta aaaaatttta ggggtgaatt    3120
atcatgtata ctccaacgat tccgttaaac aaatgcgact caatctcagc cacagtctga    3180
gtcttacaga cacacacaaa acctaacatg ccggtggcag ccacattatc acacaccgga    3240
acaaataact ttgaggcaaa aacacattat gcaagcagag aaacaccaga acagactccc    3300
agctgttgaa gtgcaaatgt gttttctata tttgagttac ttgctggtaa atcccgatcg    3360
ggaatgtaat aatcggggag ttgcattagc acttttgcag caagctaagc caactggttg    3420
ggaatgtcaa gcattcttga gcaggagtac tagtcaagtt aacaggcttc agatcccatc    3480
caatcattgt cacatttgaa tataacttga gcgggtagaa aaaatatcat aacaaaggca    3540
tcatggactg aatcctaaac atcataacga aggcatcatg gactgaatag cgatcatcat    3600
aacaacggca ggaaacagac tcccaactga atcatggtta acatgactg aattgtggtg    3660 gcactgcatg cagtgcgaga tgcatcatat ccaggtcaat tcaggttagc aaatgcaagg    3720
ccacaggagt tgccgccagg gaggaggctc taggcgaggt cacggagtt gcggtggaag    3780 ttgctgcgga ttggggaaga cctttgctcg ccaatatttg agggagagtg gagctcggat    3840
gcgggacgct gataatttgg gggaaggaaa gggaactat tgggtggaga atttttttgtt    3900 tttcacccca aaacatgttt ttgggttggt tttagcgttc ttctggagat gctcttaagc    3960
aactagcaca tgagacatgg catagatatc aagaactgca aggagaggtt caagttcaaa    4020
tctgaagaag tctgcaaggg catgtccaca gattcagcgg ttttggagtt gggaaataac    4080
ttcagctttc ttttctttt gttgttgaga cgttcttttc ttttctttt ttttttgttg    4140 ttgttgaggc gtcagctcga cgttttcatt ctacacatta gaaagtggca gtagcgcaag    4200
agataccaca gggccaaaac tactagtggt actgaaagtt ttcattcgaa gaatcagtaa    4260
gtggcactat cacaggaaga aacattgcaa ggccaaactt ggcgtccact gactgcgctt    4320
caatattact tgagcaactt gctagcctcc cgatcccgga aggatggttt gataaactaa    4380
ttctctaatt gaagtgggaa cccttaagaa ccaaacgtcc actactccaa atttgattgc    4440
aaaagaaaaa agaatctagc ccattccgcg gaatcacgcc agaaggctcg ctaattgaag    4500
catgcaagca aggcagcaaa gagaacagca cgcatcgacg ggttcctgca tccacaagca    4560
cgaacttggc aacttgccat ggtcgcctcg agggaaagaa atagaagaaa aaatggaaag    4620
agggcaagac gggggcgaaa ccagctaagc tcaccgagcg ccgcgcactg ggtgatgacg    4680
```

```
gcgacctcct cccgcgagac ctcggcggcg gccgctagat cccccaccgc ccggatcggc    4740
agggccacct cgtccgtcac cgcgagcgcc gccgacatgg agtcaaatct gcacacgagc    4800
acacgccgag aaccagaaga gactcggtga aggagtatc cccgaagaga aaaggaatta    4860
gggttaatcg agggagggtt ttatctgcac gcccccggat tcatcacgcg actgctacct    4920
gagacgataa gacgacgacg aaggcgaaat ttgatttggg ttttgcctgg cctcctctcc    4980
tctcgaagct tcacaacacg ccgagttatt tgatattgta acaatctcgt cgcgcggctt    5040
caccagttat tactccgtag ttatacttcg ctagtttagt att                     5083
```

<210> SEQ ID NO 39
<211> LENGTH: 819
<212> TYPE: DNA
<213> ORGANISM: maize

<400> SEQUENCE: 39

```
catccatcca tccatccatt tccaatccca atcccaatcc caccagtgtc cagtgctcgg     60
ggaaccgaca cagctcctca gcagagtagc cagcacgaca agcccgatca gcagacagca    120
ggcatggcac tcgcggaggc cgacgacggc gcggtggtct tcggcgagga gcaggaggcg    180
ctggtgctca agtcgtgggc cgtcatgaag aaggacgccg ccaacctggg cctccgcttc    240
tttctcaagg tcttcgagat cgcgccgtcg gcgaagcaga tgttctcgtt cctgcgcgac    300
tccgacgtgc cgctggagaa gaaccccaag ctcaagacgc acgccatgtc cgtcttcgtc    360
atgacctgcg aggcggcggc gcagcttcgc aaggccggga aggtcaccgt gagggagacc    420
acgctcaaga ggctgggcgc cacgcacttg aggtacggcg tcgcagatgg acacttcgag    480 gtgacgggt tcgcgctgct tgagacgatc aaggaggcgc tccccgctga catgtggagc    540
ctcgagatga agaaagcctg gccgaggcc tacagccagc tggtggcggc catcaagcgg    600
gagatgaagc ccgatgccta gtagtggcga ttgcgaccag tgtttaaccc atgacgcagc    660
gccgtcacag atgtcccgtg tggtcttgcg ctttagcaat ttctctctgg agggagcgtg    720
tattgttatc ttgtgatcga gagcctgtgt gctgcctttg cttcttgtga ttatatagct    780
actgaataaa gatgtagcgt tcttcaaaaa aaaaaaaaa                           819
```

<210> SEQ ID NO 40
<211> LENGTH: 165
<212> TYPE: PRT
<213> ORGANISM: maize

<400> SEQUENCE: 40

```
Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110
```

```
Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165

<210> SEQ ID NO 41
<211> LENGTH: 917
<212> TYPE: DNA
<213> ORGANISM: maize

<400> SEQUENCE: 41
cgttgtcgga acgtcccgtc gatgttcgga aacgagcacg acccgtcgac tcctgcttct    60
tggcggagaa gaaaggggac gacgagcgag cgttttgact ttgatttcct cgctaaaacc   120
ggccgctgtt tttgctttcc gcgcgagccg cccacgttat tgactgacgc tggtgcgaga   180
gcgctgctgc ctctgcggtt gccgtctgcg ctccagtggt agccgagaat attgttaggt   240
ccgtaggatc agatttgcta cgtactaaaa aaattcctta aactttaatt gtgtattttt   300
tttaaaaaaa attatagcat ttatcagcaa caaaactcta aaaacatgtt tagttcgctg   360
cttaatttat cacatattgt ctaaattta tatataaatt atttaattcg aacgactaac    420
cagaacccag acctacaata aatttgcccc cgctgctgcg ctccccagct ccccaagtcc   480
ctaacccgcc ctcgctttgt cgccgcggca cacggttttg gccgtggaca ggacagttgc   540
accctagccc cattggccga ttccgagcta ggaaggagta tatgcgtatc ggtagtaacc   600
gaggagcaac gcaacatgtc cacagcccgc gcgctggtaa cgggtccatg cgtcttggct   660
catcaggtgc cccaagggac gccctcgccc ggtctgaccc acctatataa acttaaaact   720
tgtgccccaa catcatcagt tcgtatcaca cccaacctcc cactgtaaaa aagagcagcg   780
gaacgtgcgt gcatccatcc atccatccat ttccaatccc aatcccaatc ccaccagtgt   840
ccagtgctcg gggaaccgac acagctcctc agcagagtag ccagcacgac aagcccgatc   900
agcagacagc aggcatg                                                  917

<210> SEQ ID NO 42
<211> LENGTH: 384
<212> TYPE: DNA
<213> ORGANISM: maize

<400> SEQUENCE: 42
tcgactggag cacgaggaca ctgacatgga ctgaaggagt agaaaatcac ctagctagaa    60
aggagagcac cgagcgctgc accactactg ctgatatgag cacctgaacc ttctgggcaa   120
ccacatccgg tccctgcccc tgatcatccg cagcagccat ggcgcagcag caggagaaga   180
agcagcagca gagggggaag ctgcagaggg tgctaaggga gcagaaggct cggctctaca   240
tcatccgccg atgcgtcgtc atgctcctct gctggagtga ctgatccatc tcaagcatgc   300
atgataaacc tgtgctcttt tttttccctt ctgttttttc ccctcttttt cccatccttt   360
tcaccttgcc actttggtgg gcga                                          384

<210> SEQ ID NO 43
<211> LENGTH: 41
<212> TYPE: PRT
```

```
<213> ORGANISM: maize

<400> SEQUENCE: 43

Met Ala Gln Gln Gln Glu Lys Lys Gln Gln Arg Gly Lys Leu Gln
1               5                   10                  15

Arg Val Leu Arg Glu Gln Lys Ala Arg Leu Tyr Ile Ile Arg Arg Cys
            20                  25                  30

Val Val Met Leu Leu Cys Trp Ser Asp
        35                  40

<210> SEQ ID NO 44
<211> LENGTH: 788
<212> TYPE: DNA
<213> ORGANISM: maize

<400> SEQUENCE: 44
cgactggagc acgaggacac tgacatggac tgaaggagta gaaaaactaa cacttcacgt    60
gcccccatcc ttttccgcct caagtcaagt gttcacggtc catcctctcg agagtctagg   120
cccttctccc gaagccgcag acgcagaaaa cggctctgca tatggaggcg aagaagaagc   180
cgtcggcccc cgccgccgtc ggagccgcgc cgccgccgcc gggtaacggg tacttcagca   240
ccgtcttctc cgcgccgact gcgggaagcg caagtgacgc aaagcatgcg gacttgtaca   300
cgatgctgaa caagcagagc tccagagggc agaatggcag agatggcaaa tcccacagcc   360
gccctactta caaggatggc aaacatgctc atccaaatga gccatcagaa tctccttact   420
ttggctcatc cgtgcattac ggtggtcggg agttctacag cagcgtttta cggaagcaac   480
cagccaatga accccatacg gattacaagg gggacaaccc ggatggctct gctaccagag   540
gtgattggtg gcaaggttca ctttattact gaataatctg ctgggacctc ccctttttgt   600
gaacaaggaa taaaggggt agagctgaga atggtttgtt gtagtgttgg aagtgttgac   660
gcgagccgtc aagcatcgat caatagtaat agttgtaata gttgaaagct gcgtcgtgac   720
tacaagcatc ctgttggtgg aggcagtatt ttagatccat catcacgcct ggacagatgt   780
gggtgtcc                                                             788

<210> SEQ ID NO 45
<211> LENGTH: 136
<212> TYPE: PRT
<213> ORGANISM: maize

<400> SEQUENCE: 45

Met Glu Ala Lys Lys Lys Pro Ser Ala Pro Ala Val Gly Ala Ala
1               5                   10                  15

Pro Pro Pro Pro Gly Asn Gly Tyr Phe Ser Thr Val Phe Ser Ala Pro
            20                  25                  30

Thr Ala Gly Ser Ala Ser Asp Ala Lys His Ala Asp Leu Tyr Thr Met
        35                  40                  45

Leu Asn Lys Gln Ser Ser Arg Gly Gln Asn Gly Arg Asp Gly Lys Ser
    50                  55                  60

His Ser Arg Pro Thr Tyr Lys Asp Gly Lys His Ala His Pro Asn Glu
65                  70                  75                  80

Pro Ser Glu Ser Pro Tyr Phe Gly Ser Ser Val His Tyr Gly Gly Arg
                85                  90                  95

Glu Phe Tyr Ser Ser Val Leu Arg Lys Gln Pro Ala Asn Glu Pro His
            100                 105                 110

Thr Asp Tyr Lys Gly Asp Asn Pro Asp Gly Ser Ala Thr Arg Gly Asp
```

```
            115                 120                 125
Trp Trp Gln Gly Ser Leu Tyr Tyr
    130                 135

<210> SEQ ID NO 46
<211> LENGTH: 2631
<212> TYPE: DNA
<213> ORGANISM: maize

<400> SEQUENCE: 46
aaagcttaca cttcataaga gattcatagt tttatcttac agccatcgtt gtcaacctca      60
actaccatgc aatccgtttg ggattcaact agcaagtaag gggatgtttg tttgggttta     120
taatctgtct ggattatata atctaacaac ttttgaacta acacttagtt caagaattgt     180
tggattatat aatctaggca gattataatc ccaaacaaac acttcctaag tcttgtacag     240
gctatagaga ttattttttcc agaatggagg agggataatg acaagaccta aagaaagtt     300 atgtttatgg aaaacaaaaa aatggagcca ggataatgac acaaagaaa ggtatgtttt      360 ctggaataaa aaaattaaa tatatatttt gaacttccta agactggaac atgataccta      420
agctggacag atgatcaagg acagttttac ccctggagac agaaaaactt ataagactta     480
gctttctaca tcatatcctg ttttgtatgt ctcataatta ggttccttgt attaagacga     540
ccaacctatc atttgttata caaaattcga acgactgctg aagtctcgaa gtatatagtc     600
taggctgatt aaaatgtaag tatgggttaa agtgctgctg gtaacaaact aaatacaact     660
gtatgatgtt gttgacaaca agacataact caaaatggga gcaccaacaa agtgactggc     720
accggtgatg caagcataac ctaaacacaa ctaatggaaa acgcgaattg gaaactatga     780
aagtgtccca tatatggtat accttgttca caaagggag aggtcccagc agattattca      840
gtaataaagt gaacctgaaa gtgaagtcta gcaagtcagt gtatgagcgt ccatgtatat     900
actgaagata atacacaaat tgatgcaatg ataccttgcc accaatcacc tctggtagca     960
gagccatccg ggttgtcccc cttgtactgg atttaaaatt caaataaaac attagactta    1020
agcgctccaa atgatctgta ctacgtatat ataaaaaggt tctacgtaca tccgtatggg    1080
gttcattggc tggttgcttc cgtaaaacgc tgctgtagaa ctcccgacca ccgtaatgca    1140
cggatgagcc aaagtaagga gattctgatg gctcatttgg atgagcatgt ttgccatcct    1200
tgtaagtagg gcggctgtgg gatttgccat ctgagcacga atttaaactt ccatagttaa    1260
aatcagtgct ccagattaat tctaagctaa gatggtgaga aaggtttta agtatcgttg     1320 tgcttatgaa cgcgacctaa atcgaagaga acgtcaaat tgacaagagt acccagaact     1380
acctctgcca ttctgccctc tggagctctg cttgttcagc atcgtgtaca agtccgcatg    1440
ctttgcgtca cttgcgcttc ccttgaatgc aaaacaaagt caaatgtca acgtcatatc     1500 caaatagatt ttgcataatc ctataggtcc tctattatca aaatcacccc tcatcagaat    1560
taaattggga aaccgttgaa gtccctccac aaatcgcaac atagtaacgg actctttcat    1620
caaatcgcac cagctcacta atcatgcaaa aaaattacta gaccccagg aatctgagag     1680 caaaatatca gaacgatggc gtgaagagac ggcccgtacc gcagtcggcg cggagaagac    1740
ggtgctgaag tacccgttac ccggcggcgg cggcgcggct ccgacggcgg cggggccga    1800 cggcttcttc ttcgcctcca tatgcagagc cgttttctgc gtctgcggct tcgggagaag    1860
ggcctagact ctcgagagga tggaccgtga acacttgact tgaggcggaa aaggatgggg    1920
gcacgtgaag tgttagttgt aggcggcggc ggccggcggg gaaggaagca gttggttgtt    1980
```

-continued

```
cgcctcgtgg cgtcctgctt cggccaacat ctgtgccggc atttaaaggc ctcgacggag    2040
cgactcggtt tcgctatttc ggagatctta aggggctgaa tggagaaaat tgtgtttagc    2100
tttcatccac atccatccaa cctgcagtga gacttgcaga gtgcagactc ccgtattaca    2160
gggacggtcc tgaataagtt agtagtttta tttcagagat tcaacgatgt tagtatacga    2220
attatttaga cacgtttgga atcatccagt tttttagcaa tctgatttat aaaaagtcaa    2280
gtgcttccaa acatatcaga ttatgcttcg gttcttaaaa atcggactgc ctcttccata    2340
actaaaatta gtttttaact tggtagaaat tagtgattgt aaccgctctt aggtctatgc    2400
atgtgattcc ctcgatgtct ttatcccatt tgaatattta attattattt aaaaatttta    2460
gattaaaaat attaattcaa tctatattta aaattggcaa caaagaaaaa caaagagaat    2520
aatagaatca attacttttg gaatagagta aggattgaat ttgtctttgt gtataacaaa    2580
gctagaagtt ggtttccaag aactagcctc taacacgcac acctattttt t             2631
```